United States Patent
Winther et al.

(10) Patent No.: US 7,297,523 B2
(45) Date of Patent: Nov. 20, 2007

(54) HUMAN ELONGASE GENES AND USES THEREOF

(75) Inventors: Michael David Winther, Vancouver (CA); Leah Christine Knickle, Kentville (CA); Martin Haardt, Coldbrook (CA); Stephen John Allen, New Minas (CA); Andre Ponton, St. Hubert (CA); Roberto Justo De Antueno, Coldbrook (CA); D. Kenneth Jenkins, Coldbrook (CA); Solomon O. Nwaka, Coldbrook (CA); Y. Paul Goldberg, Vancouver (CA)

(73) Assignee: Xenon Pharmaceuticals Inc., Vancouver, British Colombia (CA)

( * ) Notice: Subject to any disclaimer, the term of this patent is extended or adjusted under 35 U.S.C. 154(b) by 306 days.

(21) Appl. No.: 10/433,238

(22) PCT Filed: Nov. 29, 2001

(86) PCT No.: PCT/CA01/01705

§ 371 (c)(1),
(2), (4) Date: Nov. 20, 2003

(87) PCT Pub. No.: WO02/44320

PCT Pub. Date: Jun. 6, 2002

(65) Prior Publication Data

US 2004/0086899 A1    May 6, 2004

Related U.S. Application Data

(60) Provisional application No. 60/253,728, filed on Nov. 29, 2000, now abandoned.

(51) Int. Cl.
*C12N 9/00* (2006.01)
*C12N 1/20* (2006.01)
*C12N 15/00* (2006.01)

(52) U.S. Cl. ............... 435/183; 435/252.3; 435/320.1; 536/23.2

(58) Field of Classification Search .............. 435/183, 435/252.3, 320.1, 426; 536/23.2
See application file for complete search history.

(56) References Cited

FOREIGN PATENT DOCUMENTS

| WO | WO 00/12720 | 3/2000 |
|---|---|---|
| WO | WO 00/55333 | 9/2000 |
| WO | WO 00/70945 | 11/2000 |
| WO | WO 01/04636 | 1/2001 |
| WO | WO 01/87921 | 11/2001 |

OTHER PUBLICATIONS

Sequence search alignment between Accession No. AW812215 and Applicants' SEQ ID No. 4 (the elected sequence).*

Beaudoin, F., et al., "Heterologous Reconstitution in Yeast of the Polyunsaturated Fatty Acid Biosynthetic Pathway," Proc. Natl. Acad. Sci. U.S.A., vol. 97, No. 12, pp. 6421-6426 (2000).
Cinti, D., et al., "The Fatty Acid Chain Elongation System of Mammalian Endoplasmic Reticulum," Prog. Lipid Res., vol. 31, No. 1, pp. 1-51 (1992).
Evenson, et al., "Fatty Acid-Elongating Activity in Rapidly Expanding Leek Epidermis," Plant Physiology, vol. 109, pp. 707-716 (1995).
Leonard, A., et al., "Cloning of a Human cDNA Encoding a Novel Enzyme Involved in the Elongation of Long-Chain Polyunsaturated Fatty Acids," Biochem. J., vol. 350, pp. 765-770 (2000).
Marcelo, C., et al., "Fatty Acid Metabolism Studies of Human Epidermal Cell Cultures," J. Lipid Res., vol. 34, pp. 2077-2090 (1993).
Oh, C., et al., "ELO2 and ELO3, Homologues of the Saccharomyces cerevisiae ELO1 Gene, Function in Fatty Acid Elongation and Are Required for Sphingolipid Formation," J. Biol. Chem., vol. 272, No. 28, pp. 17376-17384 (1997).
Tvrdik, P., et al., "Role of a New Mammalian Gene Family in the Biosynthesis of Very Long Chain Fatty Acids and Sphingolipids," J. Cell Biol., vol. 149, No. 3, pp. 707-717 (2000).
Parker-Barnes, J., et al., "Identification and Characterization of an Enzyme Involved in the Elongation of n-6 and n-3 Polyunsaturated Fatty Acids," Proc. Natl. Acad. Sci. U.S.A., vol. 97, No. 15, pp. 8284-8289 (2000).
Toke, D., et al., "Isolation and Characterization of a Gene Affecting Fatty Acid Elongation in Saccharomyces cerevisiae," J. Biol. Chem., vol. 271, No. 31, pp. 18413-18422 (1996).
P. Barrett, et al., "Effects of Pebulate and Pebulate Sulphoxide On Very Long Chain Fatty Acid Biosynthesis," Phytochemicstry, vol. 48, No. 3, pp. 441-446 (1998).
R. Chapkin, et al., "Utilization of Gammalinolenic Acid By Mouse Peritoneal Macrophages, " Biochimica et Biophysica Acta, 1085:365-370 (1991).
L. Chuang, et al., "Inhibitory Effect of Conjugated Linoleic Acid on Linoleic Acid Elongation in Transformed Yeast with Human Elongase," 36:1099-1103 (2001).
D. Cinti, et al., "The Fatty Acid Chain Elongation System of Mammalian Endoplasmic Reticulum," Prog. Lipid Res., vol. 31:1-51 (1992).
M. Cotter, et al., "The Aetiopathogenesis of Diabetic Neuropathy: Metabolic Theories," Diabetic Neuropathy, pp. 97-119.
K. Dines, et al., "Contrasting Effects of Treatment with ω-3 and ω-6 Essential Fatty Acids On Peripheral Nerve Function and Capillarization in Streptozotocin-Diabetic Ratsn," Diabetologia, 36:1132-1138 (1993).
A. Goszcz, et al. "Treatment of Peripheral Vascular Disease With Misoprostol (Cytotec®): A Pilot Study," Methods Find Esp. Clin. Pharmacol., 20(5): 439-445 (1998).

(Continued)

*Primary Examiner*—Tekchand Saidha
(74) *Attorney, Agent, or Firm*—Howrey LLP

(57) ABSTRACT

The present invention relates to elongase genes, their polypeptides and their control regions, and the use of such genes, polypeptides and control regions in determining compositions for use in the treatment of disease. The identified compositions regulate the expression of the elongase genes or modulate the activity of their protein products. The nucleotide and amino acid sequences are taught for ELG4, ELG6 and ELG7. The control sequences and function are taught for ELG1, ELG2, ELG3, ELG4, ELG5, ELG6 and ELG7.

5 Claims, 36 Drawing Sheets

OTHER PUBLICATIONS

D. James, et al., "Directed Tagging of the Arabidopsis Fatty Acid Elongatinl (FAEI) Gene with the Maize Transposon Activator," The Plant Cell, vol. 7, 309-319 (Mar. 1995).

A. Kells, et al., "RT-PCR Of Fatty Acid Elongases," 20 S Biochemical Society Transactions, 25 (1997).

A. Leonard, et al., "Cloning of a Human cDNA Encoding a Novel Enzyme Involved in the Elongation of Long-Chain Polyunsaturated Fatty Acids," Biochemical, J., 350:765-770 (2000).

C. Oh, et al., "ELO2 and ELO3, Homologues of the Saccharomyces Cerevisiae EL01 Gene, Function in Fatty Acid Elongation and Are Required for Sphingolipid Formation," The Journal of Biological Chemistrty, vol. 272, No. 28, Jul. 11, 1997, pp. 17376-17384.

R. Riemersma, et al., "Linoleic Acid Content in Adipose Tissue and Coronary Heart Disease," British Medical Journal (Clin. Res. Ed.), vol. 292, May 31, 1986, p. 1423-1427.

P. Singer, et al., "Defective Desaturation and Elongation of N-6 and N-3 Fatty Acids in Hypertensive Patients," Prostaglandins Leukotrienes and Medicine, 15:159-165 (1984).

S. Suneja, et al., "Enzyme Site-Specific Changes in Hepatic Microsomal Fatty Acid Chain Elongation in Streptozotocin-Induced Diabetic Rats," Biochemica et Biophysica Acta, 1042:81-85 (1990).

D. Toke, et al., "Isolation and Characterization of a Gene Affecting Fatty Acid Elongation in Saccharomyces Cerevisiae," The Journal of Biological Chemistry, vol. 271, No. 31, Aug. 2, 1996, pp. 18413-18422.

P. Tvrdik, et al., "Role of a New Mammalian Gene Family in the Biosynthesis of Very Long Chain Fatty Acids and Sphingolipids," The Journal of Cell Biology, vol. 149, No. 3, May 1, 2000, pp. 707-717.

P. Tvrdik, et al., "*Cig*30, a Mouse Member of a Novel Membrane Protein Gene Family, Is Involved in the Recruitment of Brown Adipose Tissue," The Journal of Biological Chemistry, vol. 272, No. 50, Dec. 12, 1997, pp. 31738-31746.

Genbank Accession No. AF170907, May. 30, 2000.
Genbank Accession No. AI343530, Dec. 30, 1998.
Genbank Accession No. AL034374, Mar. 4, 2003.
Genbank Accession No. AF231981, Nov. 10, 2000.
Genbank Accession No. AAF70631, Nov. 10, 2000.
Genbank Accession No. AA282346, Apr. 3, 1997.
Genbank Accession No. BE779576, Sep. 18, 2000.
Genbank Accession No. BAA91096, Sep. 13, 2003.
Genbank Accession No. AK000341, Sep. 13, 2003.
Genbank Accession No. AI815960, Jul. 9, 1999.
Genbank Accession No. BE778035, Sep. 18, 2000.
Genbank Accession No. CAB70777, Feb. 18, 2000.
Genbank Accession No. AK027216, Sep. 29, 2000.
Genbank Accession No. AK027031, Sep. 12, 2003.
Genbank Accession No. BAB15632, Sep. 12, 2003.
Genbank Accession No. AL160091, Mar. 10, 2000.
Genbank Accession No. U97107, Mar. 19, 1998.
Genbank Accession No. AF292387, Nov. 2, 2000.
Genbank Accession No. AL132875, Dec. 21, 2000.
Genbank Accession No. AL137506, Jan. 27, 2000.
Genbank Accession No. AK027216, Sep. 12, 2003.
Genbank Accession No. BE878648, Sep. 26, 2003.
Genbank Accession No. AF151846, Jun. 1, 1999.
Genbank Accession No. AY037298, Jul. 4, 2001.

\* cited by examiner

FIGURE 4

```
ELG1  ------------MEAVVNLKQEVMKHADPRIQGFPNGSPLLMISFLLT          37
ELG2  ------------MEHFDASTSTYEKALLGPRDTRVKGWFLEDN-VIPTFICSV      40
ELG3  ------------MEHIKAFDDEINAFLDNMFGPRDSFVRGNTMIDS-VLPTPLTFV   43
ELG4  ------------MAFSDLTSRTVHLVDNWIKDADPRVEDMLLMSSPLPQAILLGF    43
ELG5  ------------MNMSVITLQEYEFEKQFNENEAIQWMQENWKKSFLFSA         38
ELG6  ------------MVTAMNVSHEVNQLFQPYNFELSKDMRPFFEEYMATSEPIAL     42
ELG7  MGLLDSEPGSVLNVVSTALNDTVEFURWTWSIADKRVENWPENQS-PWPILSIST    54

ELG1  YVYFVLSLGPRIMANRKREQLRGFMLTVYNESHVAISLY--TVYEFTMSGNLSTLIW       91
ELG2  YLLIYVTLGPKYMRNKQFSCRGILVVYNLGLTLISLY--MFCELVTGVMEGKENF         94
ELG3  MYLISFWLGNKYMKNRPALSERGIETIIYNLGITLLSAM--MTAELFHSTMEGGINL       97
ELG4  YVYFVTSLGPRLVENRKPTFIKAMITVANFFLVIFSVI--MCYFFTWSGMGIGYSE        97
ELG5  MAAFIEGCRHLMNKRAKFELRKRPIVLWSLITLAVFSIEGALRTGAYMVIILMTKG        93
ELG6  IYLMLEAVGQNIMTERKGFNLQGPLIIMSFCIALFSILGAVRMWGDMGTVLLTGG         97
ELG7  LXIIFTVWLGPKIMKDREFFQMRLVLILYNEGMVLLNLF--IFRELFMGSHNAGYSI      108

*    **   *            **   **   *    *  ***         **

ELG1  RCDPVDISNSPEALRMVRVAMLFLFSKFIEIMDTVLFLRKKDGQVTFHVFHES         146
ELG2  FCQGTRTAG-ESDMKIIRVLMWVFSKLIEFMDTFFFLLRKNNHQLIVLHHA           148
ELG3  QCQDETSAG-EADERVAKVLMWVAFSKSVEFLDTIFFVEFLDTIIFFVERKKTSQLTFHVYHHA  151
ELG4  RCDIVDISRSPTALRMARTCMLYIESKFIELLDTIIFFVLRKKNSQVLFHVFHHT       152
ELG5  LKQSVCDQGFYNGPVSKFWATARVLSKAPEEGDTIFILRKQ---KLIFLHWIHHI       146
ELG6  LKQTVCFINFIDNSTYKFWSWVFLLSKVIELGDTIAFIIERKR--PLIFIHWFHES      150
ELG7  ICQSVDISNNVHEVREGAALMWIFVSKGVEYLDTVVFFLRKNNQVSFLEVIHHC        163
```

FIGURE 4 (continued)

```
ELG1  VLPWSMNWGVKLAPGGMGSEHAMINSSVMHVDMKLYYGLSAFGPVAQPLNWKKHM    201
ELG2  SMLNINMEVMNMWPCGHSEKGATINSFIHVMFSYYGLSSV-PSMRPYLSWHKKYL   202
ELG3  SMFNINWCVINFLPCGQSERGPIIHSFIHIFMYSYYGLSVE-PSMHKYLNWKKYL   205
ELG4  IMPWIWNFGVKFAAGGLGTEHALINIAVFVVMYSYYGLSALGPAYQKYLWWKKYL   207
ELG5  FVLLYSMYSYFDMVAGGWH---MMMNYGVBAVMYSYYALRMA---GFRVSRKFAME  198
ELG6  TVLVYTSFGYKNKVPAGGWH---VTMNFGVHAIMYYYYTIKQA---NVKPPKMLPMLL 202
ELG7  TMFTLAWIGIKMWVAGGQALRGAOLNSFLHVDMYSYYGITALFGMHQKVLWWKRYL  218

ELG1  HALQLIQFYVSLBISQYFMSSCNKQYPVIHIIWM---YGTIFMESNEWYHS       254
ELG2  HQGLIQFVLTIHQHSCGVIWP--CTEPLGWLIYFQLG--YMISLTADEINFXIOI  253
ELG3  TQAQLVQFVFLTITEHMSAVVKP--CGHPFGCHIFQSS---YMLRLVFEINFVQI  256
ELG4  TSLQLVQFVIVAHHISQFFMEDCKLQFPVFACIIMS---VSFMELLEPLHFWYRA 260
ELG5  ELSQLTQMLMGCVVNYLVFCWMQHDQCHSHFQNIDFWSSLMYLSYLVLFCHEFFEA 253
ELG6  TSLQLLQMFVGALVSILTYIWRQDQGCHTTMEHHFWSFILYMPYFLIFAHFTCQT  257
ELG7  TMLQLIQFEVTIGEHALSLYTD--QPEPKWMHWALEA---EAISFLFLNEYIRL   269

ELG1  LTKG--KRIPRALQQNGAPGIAKVMAN---                            279
ELG2  VNNKGASRRRDHLKDHQNGSMAAVNGHTNSFSPLENNVKPFKLRFD---          299
ELG3  VRKK---PMKKDMQEPP--AGKEVKNGFSKAYFTAANGVMNKKAQ---          296
ELG4  YTKG--QRFPKTVKN----GTCKNFDN---                            281
ELG5  YIG---KMRKTTKAE---                                        265
ELG6  YIRP--KVTAKTKKSQ                                          270
ELG7  LKEP---KKPKAGKTAMNGISANGVSKSEKQLMIENGKKQKNGKARGD          314
```

FIGURE 8

```
  1  TACAGGCTCG TGAGGCTTCC CTCCCGCTAA GACCAGTGCG CCCTCAGCAC
 51  ACGCAGTGTG GTCTCGCCCG CCGCTCTGCG CTCGCCCTGC AGGAGAGGGA
101  GCTCTTTGAA GGCAAGGCCG AACCTCCCCC GAGCCCTGAG CTGGGCCTGC
151  CGCCACAGAT GTGCAGTCCT GCCGGGGAGC AGTCACCCGG GGACAGGGCC
201  GGGCCCCGGG CTGCACGTCG GAAGAGACA GCGTGCTCCT GAGGTGGCCA
251  GGCCGCTGCA ACTGGCCAGG GCGGGCCCGG GCGGCGAGGG AAGGGGTGGG
301  AAGCCCGGGC CGCGGCGCTT CCTGCTGGGA CCCGGCGGCA CGCCCCTGCC
351  CCCGCCCCGG CCGAGCCTGC GCTGCCGGCC TCCGGCCCTG CCGGCCGCCC
401  AATCAGCGGG CGCCCCCGC GCGGCCCGCC CCTCCCCCTC TGGTGACAGA
451  AAGTCGGCCC AGCAGATGAG GAAGTGGCAG GCAGGCAGGC TGGCCCCGGG
501  GACTTCTCTC TGGCCCTGCT CCCTCCGAGC GCTCCGCCGT TGCCCGCCTG
551  GCCCCTACGG GTGAGTCTGG ACCTTCCACG GACTCTCCAC GTGCCGGCGC
601  CCCCTGCCTG GCCAGCCCGG CCCAGCCCGG CCCAGCCCTG CCCTGCCCTG
651  CCCAGGCTGT GGGCGAGGGT GTTCCCGGGG CCAGTGGGTG GGAGGTCCCA
701  GCTCCCTGGG GCCGGGCCTC GCCAGCACCC TCCCTCCCCC ACACCCCCGT
751  CTCTGGCCCC CATTTGCCTA CACCCGGGCC TTCCTCCACC ACCCCTGCAT
801  TTACCTCTCT CCCTCCTCCT CTCCCCTCCC TCCCCCCGCT ACCCTAACTT
851  TGCCAGGCAC CTTTTCCCTT CCATCCATCT TAAAGGAAGG AAGGGACGGG
901  CTGAGTTCCC CGACGAGAGA CACACCCAGA TTTTCCTGCA GCTTGGGGAG
951  AGGTCCTCCC AGGAGCCTTG GTCCCTCCTG GCCTGCCGG
```

FIGURE 9

```
  1  CGAGGGTGGG CTTCTGCCAC CCAAATGCGG CCACAGACTC CTGCCACGCC
 51  TGGCAGTAAA AAAACCAGAG TTCAGGGCAT CGACAACTTC ACCGGGGCTA
101  TTGCGCAGGC TCTGCGTTCC ACGCAGGCTT ATTAGGAAGA AAGGGGAAAA
151  AAATTTCCCA GAGACACGTG GAACCGAGGG GCCAACCCCG GCCTAGGCTC
201  TCCACCGCAT CGGATTCTGG AATTTACGAT CACGAAAGTT CTATTGTCCC
251  GCGATTGGCT CCCGGGCCGC ATGACATCAT AGCGCTTGAT TCATCCTTCG
301  GGTCCCGATT GGCTGGCCGC GCCATTGTGA CGTCACGGTC AGCCCACGTT
351  CTGATTGTAG ATAGCCGGCG CCTTCCTCTT CCCATCGCGC GGGTCCTAGC
401  CACCGGTGTC TCCTTCTACA TCCGCCTCTG CGCCGGCTGC CACCCGCGCT
451  CCCTCCGCCG CCGCCGCCTT GCTGCTGCTC AAAGCTGCTG CCGCCCCTTG
501  GGCTAAAAG
```

FIGURE 10

```
   1  CCGGTACCTA CAGTTACTCA CTCTGCTACT GCACAAAACT CTGCAAGGGC
  51  TCCCACACCG CCCCAGGTGT GGGATGCTAA GTGTATGGTG CAGGTACCTC
 101  CGTGCACAGC CACACGGGCT GCTCTCAACC CCAATAAACA TGTTTACCAC
 151  ATGAGCCTCA CATGTGGTAA ACATTTTTTT TTTTTTTTTT TTTTTTTTGA
 201  GACAGGGTCT CATTCTGTCG CCCAGGCTGG AGTGCAGTGG CGTGATCTCG
 251  GCTCACTGCA GCCTCCACCT CCAGGGCTCA AGCCATCCTT CACCTCAGCC
 301  TCCCGAGTGG CTGGGATCAC AGGCGCAGGC CACCACACCC AGCTAATTTT
 351  TGTATTTTTT ATTTAAGAGG CGGGGTTTCG CCATGTTGCC CAGGCTGGTC
 401  CCGAACTCCT GACCTCAAGT GATTCGCCTG CCTCAGCCTC CAAAGTGCT
 451  GGGATTACAG GAGGGAACCA CCACGCCCGC CAACTTCCCA TGCTTGAGGG
 501  AGAAATGGAA GAAAGTTCAT GTAATACTCA GGCAAGTCCA ATTTTTTCGA
 551  CGTCTTTCAC TTGGGCCACA CACACAACTA AAGTAACTAG AAGCGCAGGC
 601  TCTAGGAGGC CACCGTTCTG TTCACAGTGA AGAGGGTGCG CTCACCGTTG
 651  GTCGTGTCCG CTGGAAGCCC CGCGTCAGGC CGGGAGCGGG ACAGAGACTC
 701  TTGCTCAGGG CCGTTATCCG AACTGATCCG CTTCCCACCG CACCCCAGA
 751  GAAACCCACC CAACCCCCTA AACCTAAGAA ACCCAGACTG CGCAAACCTG
 801  CAGGAACAGA GCCATTTCCC CCTAATGTGT GCTTCAAACC CACCGAAGCC
 851  CAACTGTAAG CAAGACCAGC GTGCCCGCCC TGCACGATAC TGCTTCTCCC
 901  CGCAGCAGCG GCTGCCGATC TGGGCAGCGG GTGGGTATTC CTGGGGCTCC
 951  GTGGACGTTG AGCCGCCGCG CGAAACCGGC GCCGGCTGGA CCTGCAAATC
1001  GCCGCCCGGC CGGCAGGGGA CGCCGCGGAC GCGAGGGCGA GGTCGGTCGC
```

FIGURE 10 (continued)

```
1051  CCAGGAGGGG  GCGCGCGAGG  CCGCAGGGGC  GGGGGGCGCC  GCCTCACTTG

1101  CCCTGCGCCC  CTCCCCCGCG  CGCCCTCCTG  GCGCGGCGGC  CGGCGAGGCC

1151  CCTGTGGGAG  AGGGGGCGGG  GACGAAACGG  CCCCGAGGCT  CGGAGCGCCG

1201  CGCGGCGGCG  GCGCGAGCCC  GAGGGGGCGG  GGAGGCGCGG  GCGGGTGTGC

1251  GCGCGCCGGG  CGTGGGTGTG  GGTGGGGGTA  ACCGGCGCGG  GCGCCGAGAT

1301  AGCGCCGGGC  AGAGGGACCC  GGCTACCCTG  GACAGCGCAT  CGCC
```

FIGURE 11

```
                                          30
5' ATG GCC TTC AGT GAT CTT ACA TCG AGG ACT GTG CAT CTT TAT GAT AAT TGG ATC
   M   A   F   S   D   L   T   S   R   T   V   H   L   Y   D   N   W   I 60                                      90
   AAA GAT GCT GAT CCA AGA GTT GAA GAT TGG CTC CTC ATG TCC TCG CCT CTG CCA
   K   D   A   D   P   R   V   E   D   W   L   L   M   S   S   P   L   P 120                                     150
   CAA ACC ATC CTC CTA GGA TTC TAT GTC TAT TTT GTC ACT TCC TTG GGA CCA AAG
   Q   T   I   L   L   G   F   Y   V   Y   F   V   T   S   L   G   P   K 180                                     210
   CTC ATG GAA AAT CGC AAG CCC TTT GAA CTC AAG AAA GCA ATG ATA ACG TAC AAT
   L   M   E   N   R   K   P   F   E   L   K   K   A   M   I   T   Y   N 240                                     270
   TTT TTC ATA GTA CTC TTT TCT GTG TAT ATG TGT TAT GAG TTT GTG ATG TCT GGC
   F   F   I   V   L   F   S   V   Y   M   C   Y   E   F   V   M   S   G

300
   TGG GGT ATA GGT TAT TCA TTT CGA TGT GAC ATT GTT GAC TAT TCA CGG TCA CCC
   W   G   I   G   Y   S   F   R   C   D   I   V   D   Y   S   R   S   P 330                                     360
   ACA GCT TTG AGG ATG GCA CGT ACC TGC TGG CTT TAT TAC TTC TCC AAA TTT ATT
   T   A   L   R   M   A   R   T   C   W   L   Y   Y   F   S   K   F   I 390                                     420
   GAG CTA TTA GAT ACG ATC TTT TTT GTT CTG CGC AAG AAA AAT AGC CAA GTG ACT
   E   L   L   D   T   I   F   F   V   L   R   K   K   N   S   Q   V   T 450                                     480
   TTC CTT CAT GTA TTC CAT CAT ACC ATC ATG CCG TGG ACC TGG TGG TTT GGA GTC
   F   L   H   V   F   H   H   T   I   M   P   W   T   W   W   F   G   V 510                                     540
   AAA TTT GCT GCA GGT GGT TTG GGA ACA TTC CAT GCC CTT CTA AAT ACA GCT GTA
   K   F   A   A   G   G   L   G   T   F   H   A   L   L   N   T   A   V

570
   CAT GTA GTC ATG TAT TCC TAC TAT GGA CTT TCT GCA TTG GGG CCA GCC TAC CAG
   H   V   V   M   Y   S   Y   Y   G   L   S   A   L   G   P   A   Y   Q
```

FIGURE 11 (continued)

```
        600                                          630
AAG TAT TTG TGG TGG AAA AAA TAT TTG ACA TCA TTA CAG CTT GTC CAG TTT GTT
 K   Y   L   W   W   K   K   Y   L   T   S   L   Q   L   V   Q   F   V 660                                          690
ATT GTC GCC ATC CAC ATA AGC CAG TTC TTT TTC ATG GAG GAT TGC AAG TAT CAG
 I   V   A   I   H   I   S   Q   F   F   F   M   E   D   C   K   Y   Q 720                                          750
TTT CCA GTC TTT GCG TGC ATC ATT ATG AGT TAC AGT TTC ATG TTT CTG CTG CTC
 F   P   V   F   A   C   I   I   M   S   Y   S   F   M   F   L   L   L 780                                          810
TTT CTC CAT TTT TGG TAC CGT GCT TAC ACC AAA GGT CAG AGG TTG CCC AAA ACT
 F   L   H   F   W   Y   R   A   Y   T   K   G   Q   R   L   P   K   T

840
GTG AAA AAT GGA ACT TGC AAA AAC AAA GAT AAT TGA  3'
 V   K   N   G   T   C   K   N   K   D   N   *
```

FIGURE 12

```
   1 TGCGCCTGGC TGAACACTAC ATTTTTTTTA CTTCTTTATT CATGTATTGT
  51 CTGTCATCTC CAACTAGAAT GAACGTATAG TCCCTGAGAA CGGGGAATTT
 101 GTTATCTATT GAAACTTCAG GGCCTGGAAC ATAGCAGCAC TCCAGTATTT
 151 GTTAAATAAA TGAATCCATT TGAGCTTCTG CATATTTGAA ATTTCATAAG
 201 TATATATAAA TGGTAAATTG TGATAGACTC AAAGGCTAGT ATCATTAGGC
 251 AATTGTCTCC CGTTCCCAAA AGACTTCCTA AGTCTACTAA ATGATCTGTT
 301 TTTAATATGA AAGCAAAGTT ATCTAAAAGA AAGGAGAAAT CTTTAGTTTT
 351 TTTGACTTCG AGATTCTTTG CAATTTAAGC TTTTTTTTTT TTTTTTTTTT
 401 TTTTTTTTTG CTTTTCTTTC AATGGACACT TTCGAAGTTT TACATAAAAA
 451 CATTAAAACC TCTTGTTTAA TGTAGTGGGA TTAAGCTGCC GAAGGCAATC
 501 CCTACATGTG AGGAAAATAT GCTTCGACA CCCCAATTTT TTTTTCTCC
 551 CTACCCATCC TCTCTGGTGG TCCTGACGCT CCCAGCCCCT TTTGTGTTT
 601 CTTGATTCCA TGCTGAGAAC TCGCAATACA AACTCAAAGC CCACATTTGT
 651 GAGGTGGTTG GGTCAGGACT GCAACTAAAA ATGATTATTG TTTTTTAGGT
 701 TTCTGGACAG TTCAACACCA GCCTTTGGTT TTGCCTCAGA AGCAGGGAAC
 751 TTCTCTAGGC CCCTATTTTG CCTTTCAGCT ATTGATGATC CAAATCATAC
 801 CAGCGATTAG GAGGATCATT ACCAGACACA AGGCCAGGTA CGTTTAAAAA
 851 ATAAATAAAC CAAGCGCAGG TGCACACTCC GAACGCTCAT CCCCACCCCC
 901 ACTTTCCAAT CCAACAGTAG GTAACGAGAA ATGAATTTTC TAGACTTTTT
 951 TTCCTGCAGC AGTTGCTGTT ACCAGAAACA AAGTTAGATG ATATACAATC
1001 TAATCTTCAT TGCTCTAAAA GTCCTCTCCC CATGCCCCCC AGGCTGCCTC
```

FIGURE 12 (continued)

```
1051  AATTCTCTAG TTTCTTATTC CTTATAAGCA GGGGATGGAG CTGAACCAAG
1101  TCGGCCTTCC CCTCCCAGGG CCTTCTCCTC TTGGTCTGGC TTCCATTTCA
1151  GATGCGAATT AACCCTCCCA ATACCCTTTC AGAAGCAAGG AGTCCCCTTT
1201  TTCTCCGCCT CCAGCCTCAG CTAGGTTTTC CTCATTTCGG ATTTTTCTAC
1251  AGCTCATTCC CAAATGAGTC ACGCATGACG ACAATTTCCA CTCTGCTATG
1301  TCAGCCTGGA GATGTCCCCC AAGTGATGGC ATCTGCTCTC GGAAAGAAAG
1351  GTCATCGGTG CCACGACCAG CCCCGCTAAC CCAGAGCGGC CGGTGGGCCC
1401  CAGTCCCGAG AGTCAGGGCG CGCGGCGGAG GCGAGGCCGG GGCGGCCTCC
1451  GCCCTCCCGG CCGCTCCCCC TCGCGCCGCC CCGGCTCCTC CCTCCGGCCC
1501  TCGGCGGGCA CCTGGCGGCG GCGGGCAGGG GGCGGCGCTG CGCGCGTCAC
1551  GCGGCTGGGT GGGATAGCGG GCAGGTGACA CCCGGCGGCC TCCTCCCCTT
1601  TCCAACCCAG TCGGCGGCCG GGACAGCAGG GGCCGCTGTG AGGAGCTCCG
1651  CGCTCGCGCT GCCAGTCGCC GCCCTCTCTC CCGCGCGCGC CGGCGCTTC
1701  GGCTCCGCTC CCTGTGCGGT GAGTGCGGGG TTCCAGGCCG GCGGGCAGGG
1751  GCCAAACTTT CCCGGCGCGC GGAGGAGAAG AGACTGGGGA GGGAGGCAGA
1801  GCCGAGGGGA ACGGCGTCGG GAGTGGCCGG ATGGAGGAAC TTGGGCGCGG
1851  CGCGCGAGAA GTGGGACCCG GGTGCGGGGG CCCCGGGAGC GGGGCCAGGC
1901  CCTCCCTGGG CTCGGGAGGC GCTTGGGAAG TTCTGTCCCC GCTGCCTGCG
1951  CGTGGGGAGG ACCGAGGCCC TTTTCGCCGG AGCGCGGGGC CGCGGCGCTC
2001  ACCTGCGCCT TCTCGGGAGC CCCCACCCGG CAGCATCCCG AAGGGAAGGT
2051  CGGGCCCGGT GGGCGCGCTG CGGAGCGGAG CCTGGACTGG GGTCCCGCGC
```

FIGURE 12 (continued)

```
2101  GGCGCTGGCC CTGCGGAGCG GAGCGGGAGG GGCAGAGGTG CTCGCCGGCG

2151  GGACTGGGAG GGAGAAGGAC CTGCTCGACC TTGGACGCGG AGGTCATTTT

2201  CCCAGCTCCG GGGTCTGGCC TCGCTAGCCA CCCCCCCAAA TTCCGGAGCC

2251  CCTTTCTTTC TGTTTCCTTC CTTCCCCTTT GGGCGCTTTT TTTGCTCCCG

2301  CGGCCAGATG AACTTGGGGC GCTGTCCCTT CGGCTCCCCG AGCCGCATCC

2351  TGTCTTGGTG GCTGCTGCTG GCCGGGAGGA GGCTGATGAA TACAGAGCCG

2401  TGGAACAGGT CGTGCCGGAG ATGGAAACAG GAAAGCCTGT TGTTTTGTCG

2451  TCCCAG
```

FIGURE 13

```
   1  GTGAGCCACC ACCGCGGCCG GTCCCTTCCT CCTTTAAAAA TTTTTCTCCC
  51  AGTTCCCACT TTTTGTGGGT TAGAGGCATC TAAATTGAAT GAAAGTACCC
 101  TTTTTGGACT ACTGGGGAGG TGGGGGGATG TTCTCAGAAG GGGAATTTTC
 151  TTTCTGGTCC TAATATCCAC CTAATTTTTA AAAGCAGGGC TCCTTATTAT
 201  TTTGTAAAGT TTACAATTAC ATCATTAGAT ACTTCCATGT CTCATATTTC
 251  ATTTTTCCAA ACTCTTGGGG GAAATGAGTG GAGGGATGGA TGGAATAGAA
 301  AATAGTTTTT CCTCTTGGAG GCTGAGGGCC CAGTAGGGGT CAACAGTACA
 351  TTCAGCCCTC TCCTCACATA TTCTGTTCTA CCTACAAGTA CAGCAAGTAA
 401  AGCCAAATTT CTCATGCATG CAAATAAAGT TTTTGCATTT GGCCAGTCGG
 451  TCCAGTTCTC CTGTCAGCTT CCTTCCCCAC TCTGCCTCTG TTCATTAATC
 501  CCCCCCTTCC CGGTACCTAA ACCTCCACC TAACCCAGCC CTTTCTTCCA
 551  CTTCCGGCTA CTAGCCTCTC TCGCCTATCC ACTATCCTCA CACTCAGCAT
 601  CCCCTGTCTG TACGAGATTA AGGAGCTCTG CCGTCCGCAG GGCCTGGGTT
 651  AGCGTGAATC TAAGCCAGAG CTCCCGGGTG GGGGTGGGGG TAGGGGTGGG
 701  GGTGGTCCCA GAGGTAGGGC GAGGAGGTGG GAAGCGTATT CCCTTCACTG
 751  GTGATCTCAA CGTAGATTTG CCCGGAGTTC TCTTGCAAGA GAGCTGGCAG
 801  GTTTTACTAT TTCCCAATCG TTTACTCGCC AAGCTCTCGG GTCCACGCGC
 851  CGCGGGGATG CGCCCTGCAA GCTGAAACTT CATTCAAAGC AAGGCGGCCC
 901  ACGAGGTTGG GCTTAGGGGA TCTGGATGAC CTCCAGGCCA CTTCCTTTCT
 951  CTCTGCGCCC TTCCCCCACT CTTCCAACCA CCTTCGCTGT AAACAAAACT
1001  GTCCCCCCCG GGCGGAGAGA GGTCGCGCTC TTTCGCACAC TCCCTCGCCA
```

FIGURE 13 (continued)

```
1051  AGGGTTAATT TCTCAAATCG CACGAGGGGG AGGAGATTTC CCTGTAGACG

1101  AGTAAAAAGG GTGATGGACA AACGTGCGGG CACTAAGACC GCAAGGCATT

1151  CATTTCCTCC TACGGTGGAT GCGGACGCCG GGAGGAGGAG AGCCCCAGAG

1201  AGAGGAGCTG GGAGCGGAGG CGCAGGCAAT GCTCAGCCCT GGATGTAGCT

1251  GAGAGGCTGG GAGAAGAGAC GACCGCTGGA GACCGAGCGG CGTGGGGAAG

1301  ACCTAGGGGG GTGGGTGGGG GAAGCAGACA GGAGAACACT CGAAATCAAG

1351  CGCTTTACAG ATTATTTTAT TTTGTATAGA GAACACGTAG CGACTCCGAA

1401  GATCAGCCCC A
```

FIGURE 14

```
                                           30
5'  ATG GTC ACA GCC ATG AAT GTC TCA CAT GAA GTA AAT CAG CTG TTC CAG CCC TAT
     M   V   T   A   M   N   V   S   H   E   V   N   Q   L   F   Q   P   Y 60                                      90
    AAC TTC GAG CTG TCC AAG GAC ATG AGG CCC TTT TTC GAG GAG TAT TGG GCA ACC
     N   F   E   L   S   K   D   M   R   P   F   F   E   E   Y   W   A   T 120                                     150
    TCA TTC CCC ATA GCC CTG ATC TAC CTG GTT CTC ATC GCT GTG GGG CAG AAC TAC
     S   F   P   I   A   L   I   Y   L   V   L   I   A   V   G   Q   N   Y 180                                     210
    ATG AAG GAA CGC AAG GGC TTC AAC CTG CAA GGG CCT CTC ATC CTC TGG TCC TTC
     M   K   E   R   K   G   F   N   L   Q   G   P   L   I   L   W   S   F 240                                     270
    TGC CTT GCA ATC TTC AGT ATC CTG GGG GCA GTG AGG ATG TGG GGC ATT ATG GGG
     C   L   A   I   F   S   I   L   G   A   V   R   M   W   G   I   M   G

300
    ACT GTG CTA CTT ACC GGG GGC CTA AAG CAA ACC GTG TGC TTC ATC AAC TTC ATC
     T   V   L   L   T   G   G   L   K   Q   T   V   C   F   I   N   F   I 330                                      360
    GAT AAT TCC ACA GTC AAA TTC TGG TCC TGG GTC TTT CTT CTC AGC AAG GTC ATA
     D   N   S   T   V   K   F   W   S   W   V   F   L   L   S   K   V   I 390                                      420
    GAA CTC GGA GAC ACA GCC TTC ATC ATC CTG CGT AAG CGG CCA CTC ATC TTT ATT
     E   L   G   D   T   A   F   I   I   L   R   K   R   P   L   I   F   I 450                                     480
    CAC TGG TAC CAC CAC AGC ACA GTG CTC GTG TAC ACA AGC TTT GGA TAC AAG AAC
     H   W   Y   H   H   S   T   V   L   V   Y   T   S   F   G   Y   K   N 510                                    540
    AAA GTG CCT GCA GGA GGC TGG TTC GTC ACC ATG AAC TTT GGT GTT CAT GCC ATC
     K   V   P   A   G   G   W   F   V   T   M   N   F   G   V   H   A   I

570
    ATG TAC ACC TAC TAC ACT CTG AAG GCT GCC AAC GTG AAG CCC CCC AAG ATG CTG
     M   Y   T   Y   Y   T   L   K   A   A   N   V   K   P   P   K   M   L
```

FIGURE 14 (continued)

```
     600                              630
CCC ATG CTC ATC ACC AGC CTG CAG ATC TTG CAG ATG TTT GTA GGA GCC ATC GTC
 P   M   L   I   T   S   L   Q   I   L   Q   M   F   V   G   A   I   V 660                              690
AGC ATC CTC ACG TAC ATC TGG AGG CAG GAT CAG GGA TGC CAC ACC ACG ATG GAA
 S   I   L   T   Y   I   W   R   Q   D   Q   G   C   H   T   T   M   E 720                              750
CAC TTA TTC TGG TCC TTC ATC TTG TAT ATG ACC TAT TTC ATC CTC TTT GCC CAC
 H   L   F   W   S   F   I   L   Y   M   T   Y   F   I   L   F   A   H 780                              810
TTC TTC TGC CAG ACC TAC ATC AGG CCC AAG GTC AAA GCC AAG ACC AAG AGC CAG
 F   F   C   Q   T   Y   I   R   P   K   V   K   A   K   T   K   S   Q

TGA  3'
 *
```

FIGURE 15

```
   1  GATTAGCTGT CAGGCTATAT ATGGAGCCAT CAGGAACCAC TGAAGGTTTT
  51  TTTTTTTTTT TTTTTTTTTG AGACGGAGTC TCACTCTGTC AGCCAGGCTG
 101  GAGTGCAGTG GCACGATCTC TGCTCACTGC AAGCTCTGCC TCCCAGGTTC
 151  ACGCCATTCT CCTGCCTCAG CCTCCCGAGT AGCTGGGACT ACAGGCGCCT
 201  GCCACCACGC CCGGCTAATT TTTTGTATTT TTTAGTAGAG ACGGGGTTTG
 251  ACGGTGTTAG CCAGGATGGT CTCGATCTCC TGACCTCATG ATCTGCCCGC
 301  CTCGGCCTCC CAAGGTGCTG GGATTACAGG CGTGAACCAC CGTGCCCGGC
 351  CGAACCACTG AAGGTTTTTA AGCAGGAAAG CAGAGCTGTT TTCTGGATGA
 401  GCAAACAGAA AGTAGTGGTT TTCCAAGTAC AGTCTGAGAC AACCTATAGG
 451  ACCAGAATCT CTGCAGTTGA GGCTCAGGAA TCTGGTAATC AGCCAGGTAT
 501  AGGAACTCTT TTCTGATTGC AATGCAGTGA AGAGCAGAAG CACTGTATTA
 551  GAGAAAGAGG CAGTGCAACC AGGTAACGTG ACCAGGTGAG AAGTGATGAG
 601  GTACAGAGAC AAAGAGATGC ACTTTTGAGT CACTTAGATG GCACTGATAG
 651  GACTTCCACT ACACCCTCGC ATAGACAGTG GCTGAGGTTC AGGAAATAGA
 701  GCTGGGGTTC CTACTTGGAT CCTCTGGCTC TAGAGCTTTA CTGCACATAG
 751  CCATTTATAC CCACATCTTG ATTTTAATTA TTTTATATCT ATGTTTCTTA
 801  GCACTTTTTG CAAATTTCCA CCTTATCTCA AACTGCCCTC AAGCCTTGTA
 851  TTTCTCCTTC GCTTTCATAA AACCTAGGAA AGAAATAAGG GACAGCCAAG
 901  TAAAACTTTT AAAAGTTTTA GAACATTTAT TTCTTTGGGG CTGGTTACAC
 951  AGGCGAGAAA GAAGTAGATT TGGTTAGGGA GAGAAAACAA CAGGCCTTGG
1001  GGAGATACAC TGGCTCTCCC CCTCCCTAAA CCCTAAGAGG CCTCCAGGAA
```

FIGURE 15 (continued)

```
1051  ACCTGAAGAC AATAATTCCA GAAGCCCAGA GGGTGACCCC ATTTCCTCTC
1101  TCCATGGTTA TTACTGTCAG TCTGGAGCAG TTCAGGAATT CAGGAAACTA
1151  TAAAGAAACC ACAACAGCCT CAACAACCCA AACATCAACA TCAACAACCT
1201  CAACAATAAA ACTCCTTAAA ATTCATCTCC TTCCACCCAC TCACAACCGC
1251  AGACTCGAAG CTAGGAGGTG GAAGGGACTA CAGAAGCTCT GCGTTGCCCA
1301  GGTTAGTATT TGCTCATCAC AGGCCTGGGT TTCCCAGGAT CTCAGGGAGC
1351  CTGGAAACTG ACGCCTCCAT TTCTGGGTGG GAGCACCAAA GCCTAAGGAC
1401  ACCTTTCCTC TCTCTTCACT GCTAAGCAGG TCAAGATTAA AGCAAACCGA
1451  GGCAAAGGCC ACGGTTGACA GTTCCAAGGG AACCCGCAAG GCCGCACAGG
1501  ATGGGGTGGA CGTTTTACGG GAGAAAAGGC TGGGGAAGTG GGCGGGCGAT
1551  GGCCTACGAC GGGACTTGGG GCGGGGTGTG CGAAACGCCT GGCAGGCGGG
1601  CCCTTGAGTA TGACCAATCA GAATGCGGAC TGCGTCCCAG GGGCGGAGCA
1651  GAGGCGTATC TTGGTCGAGA TTGGATAGCG GCGGGGCGCA GGAAAGAGGT
1701  CGCGCCAGCC CGGGCAGGCA GCTTTGCAAG TCCGCGTTAT ATATCGCAGT
1751  GGCTGCGCCC GGGATAGCTG GCTGCGCCGC CGCGCACATG CCTAGGTTCG
1801  ACGCCCTCCT CCCTTTGCCC AGGAGTTCCT TCTGTCCCGG CTCTGTTCCG
1851  TCTCGCCCCG AGGTTCACGC CATCCTCGGA GCCCAGCCT TTCACCCAGC
1901  GCCTCCAAGC TTTGGACCTT GACTTCTGCA AAACTAG
```

FIGURE 16

```
                                        30
5'  ATG GGG CTC CTG GAC TCG GAG CCG GGT AGT GTC CTA AAC GTA GTG TCC ACG GCA
    M   G   L   L   D   S   E   P   G   S   V   L   N   V   V   S   T   A 60                                      90
    CTC AAC GAC ACG GTA GAG TTC TAC CGC TGG ACC TGG TCC ATC GCA GAT AAG CGT
    L   N   D   T   V   E   F   Y   R   W   T   W   S   I   A   D   K   R 120                                     150
    GTG GAA AAT TGG CCT CTG ATG CAG TCT CCT TGG CCT ACA CTA AGT ATA AGC ACT
    V   E   N   W   P   L   M   Q   S   P   W   P   T   L   S   I   S   T.

180                                     210
    CTT TAT CTC CTG TTT GTG TGG CTG GGT CCA AAA TGG ATG AAG GAC CGA GAA CCT
    L   Y   L   L   F   V   W   L   G   P   K   W   M   K   D   R   E   P 240                                     270
    TTT CAG ATG CGT CTA GTG CTC ATT ATC TAT AAT TTT GGG ATG GTT TTG CTT AAC
    F   Q   M   R   L   V   L   I   I   Y   N   F   G   M   V   L   L   N

300
    CTC TTT ATC TTC AGA GAG TTA TTC ATG GGA TCA TAT AAT GCG GGA TAT AGC TAT
    L   F   I   F   R   E   L   F   M   G   S   Y   N   A   G   Y   S   Y 330                                     360
    ATT TGC CAG AGT GTG GAT TAT TCT AAT AAT GTT CAT GAA GTC AGG ATA GCT GCT
    I   C   Q   S   V   D   Y   S   N   N   V   H   E   V   R   I   A   A 390                                     420
    GCT CTG TGG TGG TAC TTT GTA TCT AAA GGA GTT GAG TAT TTG GAC ACA GTG TTT
    A   L   W   W   Y   F   V   S   K   G   V   E   Y   L   D   T   V   F 450                                     480
    TTT ATT CTG AGA AAG AAA AAC AAC CAA GTT TCT TTC CTT CAT GTG TAT CAT CAC
    F   I   L   R   K   K   N   N   Q   V   S   F   L   H   V   Y   H   H 510                                     540
    TGT ACG ATG TTT ACC TTG TGG TGG ATT GGA ATT AAG TGG GTT GCA GGA GGA CAA
    C   T   M   F   T   L   W   W   I   G   I   K   W   V   A   G   G   Q

570
    GCA TTT TTT GGA GCC CAG TTG AAT TCC TTT ATC CAT GTG ATT ATG TAC TCA TAC
    A   F   F   G   A   Q   L   N   S   F   I   H   V   I   M   Y   S   Y
```

FIGURE 16 (continued)

```
    600                              630
TAT GGG TTA ACT GCA TTT GGC CCA TGG ATT CAG AAA TAT CTT TGG TGG AAA CGA
 Y   G   L   T   A   F   G   P   W   I   Q   K   Y   L   W   W   K   R 660                              690
TAC CTG ACT ATG TTG CAA CTG ATT CAA TTC CAT GTG ACC ATT GGG CAC ACG GCA
 Y   L   T   M   L   Q   L   I   Q   F   H   V   T   I   G   H   T   A 720                                      750
CTG TCT CTT TAC ACT GAC TGC CCC TTC CCC AAA TGG ATG CAC TGG GCT CTA ATT
 L   S   L   Y   T   D   C   P   F   P   K   W   M   H   W   A   L   I 780                              810
GCC TAT GCA ATC AGC TTC ATA TTT CTC TTT CTT AAC TTC TAC ATT CGG ACA TAC
 A   Y   A   I   S   F   I   F   L   F   L   N   F   Y   I   R   T   Y

840
AAA GAG CCT AAG AAA CCA AAA GCT GGA AAA ACA GCC ATG AAT GGT ATT TCA GCA
 K   E   P   K   K   P   K   A   G   K   T   A   M   N   G   I   S   A 870                              900
AAT GGT GTG AGC AAA TCA GAA AAA CAA CTC ATG ATA GAA AAT GGA AAA AAG CAG
 N   G   V   S   K   S   E   K   Q   L   M   I   E   N   G   K   K   Q

930
AAA AAT GGA AAA GCA AAA GGA GAT TAA  3'
 K   N   G   K   A   K   G   D   *
```

FIGURE 17

```
   1 GGAAATACCT GAAGCTGTTT TAACAATTTC TCCTTGTATT AAGTATTATG
  51 CTGCAGTTTT GCGTGTGTGA ATGGAAGTAT GGGTAGAGAT CTGTTCTCCC
 101 TAAAAACTCC AGGATTCCAC AATATAGAAA TAGTAATCAA ATTTTTAGGT
 151 GAAGCTCGAA CTAATCCGAA CTTTGTTAGA TCATCACTGT AAATGAATGG
 201 GTATTTATCC ACTCCCTAAA TGAAGAGACT TGACTGGATT TCTTTTTTTT
 251 ATATAGCTAC TAGAATCTGT TACACATAAT TTAGGATTGA GACTTGAGAA
 301 ATTGTCATTC CAATCCAGAA AACTTTAGAT TTGCAAATAT ATTTGACAAA
 351 TTAATAAATT AACATTTTAT TTGGTTAATT TCAAGAATAG GGCATTTAAA
 401 GAAGTCTGTG TTTGCTTTAG TTCGGCAATA AAGTTCCTGC CACTCACAAT
 451 AATCCTTATT ATTCTCTGAA AGACATGTTA TATTTTTGTC ATCATAAATA
 501 TTTATTAATT ACTGTTTATA GCACTGGGTT AGGTACTCAT CAAGCAACCA
 551 AAAATAATTC TTACCATCTA GGATGCTTCC AATATAAAAT ATAGACAATA
 601 TATAACCAGG TCAATTGGGA AATAGATCAT TTCAGTATGA TAAAAGATAG
 651 TATTCACATT AACAGTGTGA AAGGGCAGGA ACAATAAGAC ACTTGACTCA
 701 CTGGTCTTTA AAATGTAGCA TCCAAAATGA GCAAGTGGAG AAAAGGTTAA
 751 ACAAGTAGGT GACACATTTA AAAACAAGT AGATGAAAGG ACTATTCTCA
 801 AAAATCTTGT TTTATGTGAG AAACCATCAA ATTATGAATT CCAAGTACTG
 851 TATTTTTTTT ACTTTTCAAG GGTAGGCTCT CCTATACCTT ATCTAAACAA
 901 TTTTTCAAAA TAGCCACAAT TACTTTGTTT TCCTCTCTAC ACTAAATTGC
 951 CCTTTGCCTC TTGAGCGATT ATCTTTTTCA GATTCACCTC AACTTCTTCA
1001 GGTTCAAGCG GACTTCACCT GTAAGCCCCT CTCGGTTCTC CCTCTTCTCT
```

FIGURE 17 (continued)

```
1051  GAACTACTAA TGGCCTAATT TAGCACAATT ATATTGCTTT GTTCATTCCA
1101  TGTATAGTAA AAGAGTCTAC AAAACACATG CAAGCATTCA TGCAATTATA
1151  TGTTGATTTG TTCATGGGTC GACCCCAAAG TCTATTCTCC ATCGCTGAAG
1201  CATGGAAGAC AAATACCCTT CACTTCTTCA GAGGCATAAC ACATGCACTT
1251  CTCTTGTCAT GGTGACAGGC ATGTGCTGGT GGAGGTCAAA GAAACAGGAA
1301  CACAAGTGAA ATCGAGGTGA GTGTCAGGTA AGGACCAAAG CACCACGCCT
1351  ACCTCATCTT TGCCCACAGA ACACCCATTC TTCCCGTGTC CTGTTTCCCA
1401  GGACGTATCC GGGGCGGATA AGAAATCACC CGTGGGGAGG CGGTGAACTC
1451  CTCCGCAGGG GCCGATGCCC GGGACAGGGG CGGGGAAGGC TAATGAGGCG
1501  ACTTGTGCGG GGAGGGGCCA AGGAGGAGCC CAGGTGTCCC GCTCCCGCTC
1551  GACGGCGCGC GCCTGCGCGA GCCCAGTTGG CGTCGCACCC TTGAGCGCAG
1601  CATCCCTACG CCAGCGAGTC CCAATACTAG GGAGGGAGGG AGGGAGGAGG
1651  GGCGGCCGGC CCCCGCCCC CGCGCGCGGC CACGTGACGC CGGCTGAGGA
1701  GATTGGAGGG GCGGCTGCGC GAGGCTGCAG ACTGGTGCAG CGCACTGTGC
1751  TGGCGGCTGG GCCTCCTCCA CCTCCTCGTC TTTCTCCCGG GAACCTTGAC
1801  GACGCCTTCC GCTTGGCCCT GCCTTCTGCC GCATCCCCGC CGCCGCGGCG
1851  CCTTGAGGAG CAGGAGAAGA CGCAGCCGGG CCGCCGCCGT TAGAGGGGTT
1901  CCCGGCCGCC GCTCGCCCCG TCGGCCGCCA CCGCCTCCGG GGTCAGCCCT
1951  CTCTCTGGGT CTCCGCTTTC TCCTGCCGCC AGCGCCCGCT CATCGCCGCG
```

US 7,297,523 B2

HUMAN ELONGASE GENES AND USES THEREOF

CROSS REFERENCE TO RELATED APPLICATIONS

This application is the National Stage of International Application No. PCT/CA01/01705 filed Nov. 29, 2001, which claims priority to U.S. Provisional Application No. 60/253,728 (now expired), filed Nov. 29, 2000, the entire contents of which are incorporated herein by reference.

FIELD OF THE INVENTION

This invention relates to the identification of compounds that modulate the activity of fatty acid elongase enzymes involved in lipid metabolism and/or effectively regulate the level of expression of the elongase genes, and to compounds so identified.

BACKGROUND OF THE INVENTION

Polyunsaturated fatty acids (PUFAs) are major components of lipid compounds and complexes, such as phospholipids and lipoproteins, which provide a number of structural and functional characteristics to a wide range of biological constituents, such as the cell membranes. PUFAs are essential for the proper development, maintenance and repair of tissue. Other biological functions of PUFAs include their involvement in the expression of some genes and their role as precursor molecules for conversion into biologically active metabolites that regulate critical physiological functions. Consequently, a lack of, or imbalance in, PUFA levels has been attributed to certain pathological conditions.

FIGS. 1, 2 and 3 show the required desaturation and elongation steps for the production of long chain fatty acids in the n-3, n-6 and n-9/n-7 PUFA families, respectively. Fatty acid chain elongation systems have been found in liver, brain, kidney, lung, adrenals, retina, testis, small intestine and blood cells, namely leukocytes (Cinti et al., 1992, *Prog. Lipid Res.*, 31: 1-51).

Elongase genes have been identified in *Arabidopsis* (James et al., 1995, *Plant Cell*, 7: 309-319 and in *C. elegans* (WO 00/55330, September, 2000, Napier J. A.). Three separate elongase genes, ELO1, ELO2 and ELO3, have been identified from *S. cerevisiae*. ELO1 elongates myristic acid to palmitic acid (Toke D. A. and Martin C. E., 1996, *J. Biol. Chem.*, 271: 18413-18422) while ELO2 and ELO3 elongate long chain saturated fatty acids (Oh et al., 1997, *J. Biol. Chem.*, 272: 17376-17384).

Deficiencies in polyunsaturated fatty acids (PUFAS) have been associated with a number of diseases such as eczema, cardiovascular disorders, inflammation, psychiatric disorders, cancer, cystic fibrosis, pre-menstrual syndrome and diabetes (Horrobin D. F. [ed.], 1990, *Omega-6 Essential Fatty Acids: Pathophysiology and Roles in Clinical Medicine*, Wiley-Liss, NY and Mazza G. and Domah B. D. [eds.], 2000, *Herbs, Botanicals and Teas*, Technomic Publishers, Lancaster, Pa.). Diets supplemented with PUFAs have been attempted as a treatment for a number of these conditions. The level of success for such applications has varied considerably.

Low levels of linoleic acid (18:2n-6, LA), dihomogamma-linolenic acid (20:3n-6, DGLA) and arachidonic acid (20:4n-6, AA) in adipose tissue of males have been correlated with increased mortality from coronary heart disease (Riemersma et al., 1986, *Br. Med. J. [Clin. Res. Ed.]*, 292: 1423-1427). The supplementation of LA and alpha-linolenic acid (18:3n-3, ALA) to patients suffering from hypertension did not increase the tissue levels of AA or eicosapentaenoic acid (20:5n-3, EPA) which indicates defective desaturation and elongation in the n-6 and n-3 fatty acid systems (Singer et al., 1984, *Prostaglandins Leukot. Med.*, 15: 159-165). Misoprostol, a prostaglandin E1 (PGE1) analogue, has been successfully used to treat peripheral vascular disease (Goszcz et al., 1998, *Methods Find. Exp. Clin. Pharmacol.*, 20: 439-445). PGE1 is a cyclooxygenase product of DGLA.

It has been observed that PUFAs can alleviate and correct some of the symptoms of diabetic neuropathy (Dines et al., 1993, *Diabetologia*, 36: 1132-1138 and Cotter et al., 1995, *Diabetic Neuropathy: New Concepts and Insights*, Elsevier Science B. V., Amsterdam, pp. 115-120). Researchers have speculated that the production or modulation of the cyclooxygenase and lipoxygenase metabolites of the n-3 and n-6 fatty acid families is responsible for some of these beneficial effects.

Most of the lipid metabolism disorders are characterized by a deficiency in essential fatty acids. This deficiency has been attributed to altered rate-limiting steps of delta-6-desaturation (D6D) and/or delta-5-desaturation (D5D) in PUFA biosynthesis.

SUMMARY OF INVENTION

The present invention teaches an isolated polynucleotide sequence, comprising a polynucleotide sequence which is selected from the group consisting of: (a) a sequence comprising SEQ ID NO: 4 (ELG4); (b) a sequence comprising SEQ ID NO: 8 (ELG6); (c) a sequence comprising SEQ ID NO: 11 (ELG7); (d) a sequence which is at least 80% homologous with a sequence of any of (a) to (c); (e) a sequence which is at least 90% homologous with a sequence of any of (a) to (c); (f) a sequence which is at least 95% homologous with a sequence of any of (a) to (c); (g) a sequence which is at least 98% homologous with a sequence of any of (a) to (c); (h) a sequence which is at least 99% homologous with a sequence of any of (a) to (c); and; (i) a sequence which hybridizes to any of (a) to (h) under stringent conditions. The isolated polynucleotide sequence may be cDNA.

The invention also teaches an isolated polypeptide comprising an isolated polypeptide selected from the group consisting of: (a) a sequence comprising SEQ ID NO: 5 (ELG4); (b) a sequence comprising SEQ ID NO: 9 (ELG6); (c) a sequence comprising SEQ ID NO: 12 (ELG7); (d) a sequence which is at least 80% homologous with a sequence of any of (a) to (c); (e) a sequence which is at least 90% homologous with a sequence of any of (a) to (c); (f) a sequence which is at least 95% homologous with a sequence of any of (a) to (c); (g) a sequence which is at least 98% homologous with a sequence of any of (a) to (c); and (h) a sequence which is at least 99% homologous with a sequence of any of (a) to (c).

The invention teaches an isolated polynucleotide sequence, comprising a polynucleotide sequence which is selected from the group consisting of: (a) a sequence comprising SEQ ID NO: 1 (control region for ELG1); (b) a sequence comprising SEQ ID NO: 2 (control region for ELG2); (c) a sequence comprising SEQ ID NO: 3 (control region for ELG3); (d) a sequence comprising SEQ ID NO: 6 (control region for ELG4); (e) a sequence comprising SEQ ID NO: 7 (control region for ELG5); (f) a sequence comprising SEQ ID NO: 10 (control region for ELG6); (g) a sequence comprising SEQ ID NO: 13 (control region for ELG7); (h) a sequence which is at least 80% homologous with a sequence of any of (a) to (g); (i) a sequence which is at least 90% homologous with a sequence of any of (a) to (g); 0) a sequence which is at least 95% homologous with a sequence of any of (a) to (g); (k) a sequence which is at least 98% homologous with a sequence of any of (a) to (g); (1) a sequence which is at least 99% homologous with a sequence of any of (a) to (g); and; (m) a sequence which hybridizes to any of (a) to (1) under stringent conditions.

The invention includes an isolated polynucleotide fragment selected from the group consisting of: (a) a sequence having at least 15 sequential bases of nucleotides of a sequence of the invention; (b) a sequence having at least 30 sequential bases of nucleotides of a sequence of the invention; and (c) a sequence having at least 50 sequential bases of nucleotides of a sequence of the invention. The invention includes a polypeptide sequence which retains substantially the same biological function or activity as or is a functional derivative of a polypeptide sequence of the invention.

The invention includes an isolated polynucleotide sequence, comprising a polynucleotide sequence which retains substantially the same biological function or activity as or is a functional derivative of a polynucleotide sequence of the invention.

The invention also teaches a vector comprising a polynucleotide sequence of the invention in a suitable vector. The vector may be heterologous to the sequence. The vector may contain or encode a tag. The invention also teaches a host cell comprising a polynucleotide sequence of the invention in a host cell which is heterologous to the sequence.

The invention teaches a method for identifying a compound which inhibits or promotes the activity of a polynucleotide sequence of the invention, comprising the steps of: (a) selecting a control animal having the sequence and a test animal having the sequence; (b) treating the test animal using a compound; and, (c) determining the relative quantity of an expression product of the sequence, as between the control animal and the test animal.

The invention also teaches a method for identifying a compound which inhibits or promotes the activity of a polynucleotide sequence of the invention, comprising the steps of: (a) selecting a host cell of the invention; (b) cloning the host cell and separating the clones into a test group and a control group; (c) treating the test group using a compound; and (d) determining the relative quantity of an expression product of the sequence, as between the test group and the control group.

The invention further teaches a method for identifying a compound which inhibits or promotes the activity of a polynucleotide sequence of the invention, comprising the steps of: (a) selecting a test group having a host cell of the invention or a part thereof, and selecting a suitable control group; (b) treating the test group using a compound; and (c) determining the relative quantity or relative activity of a product of the sequence or of the sequence, as between the test group and the control group.

The invention teaches a process for producing a polypeptide sequence of the invention comprising the step of culturing the host cell of the invention under conditions sufficient for the production of the polypeptide.

The invention teaches a method for identifying a compound which inhibits or promotes the activity of a polypeptide sequence of the invention, comprising the steps of: (a) selecting a control animal having the sequence and a test animal having the sequence; (b) treating the test animal using a compound; (c) determining the relative quantity or relative activity of an expression product of the sequence or of the sequence, as between the control animal and the test animal.

The invention also teaches a method for identifying a compound which inhibits or promotes the activity of a polypeptide sequence of the invention, comprising the steps of: (a) selecting a host cell of the invention; (b) cloning the host cell and separating the clones into a test group and a control group; (c) treating the test group using a compound; and (d) determining the relative quantity or relative activity of an expression product of the sequence or of the sequence, as between the test group and the control group.

The invention includes a method for identifying a compound which inhibits or promotes the activity of a polypeptide sequence of the invention, comprising the steps of: (a) selecting a test group having a host cell of the invention or a part thereof, and selecting a suitable control group; (b) treating the test group using a compound; and (c) determining the relative quantity or relative activity of a product of the sequence or of the sequence, as between the test group and the control group.

The invention includes a method for identifying a compound which modulates a biological activity of a polypeptide sequence of the invention, comprising the steps of: (a) providing an assay which measures a biological activity of a polypeptide sequence of the invention; (b) treating the assay with a compound; and (c) identifying a change in the biological activity of the polypeptide, wherein a difference between the treated assay and a control assay identifies the compound as modulator of the polypeptide. The polypeptide in this assay may be provided in a purified, reconstituted, cell extract or whole cell assay format, as required to assay the biological activity in question.

The invention also teaches a method for identifying a compound which inhibits or promotes the activity of a polynucleotide sequence of the invention, comprising the steps of: (a) selecting a host cell of the invention; (b) cloning the host cell and separating the clones into a test group and a control group; (c) treating the test group using a compound; and (d) determining the relative quantity of an expression product of an operably linked polynucleotide to the sequence, as between the test group and the control group.

The invention also teaches a method for identifying a compound which inhibits or promotes the activity of a polynucleotide sequence of the invention, comprising the steps of: (a) selecting a test group having a host cell of the invention or a part thereof, and selecting a suitable control group; (b) treating the test group using a compound; and (c) determining the relative quantity of an expression product of an operably linked polynucleotide to the sequence, as between the test group and the control group.

The invention includes a composition for treating a PUFA disorder comprising a compound which modulates a sequence of the invention and a pharmaceutically acceptable carrier. The invention includes the use of a composition of the invention for treating PUFA disorders.

The invention includes a method for diagnosing the presence of or a predisposition for a PUFA disorder in a subject by detecting a germline alteration in a sequence of the invention in the subject, comprising comparing the germline sequence of a sequence of the invention from a tissue sample from the subject with the germline sequence of a wild-type of the sequence, wherein an alteration in the germline sequence of the subject indicates the presence of or a predisposition to the PUFA disorder. The invention teaches a method for diagnosing the presence of or a predisposition for a PUFA disorder in a subject, comprising comparing the sequence of a polypeptide of the invention from a tissue sample from the subject with the sequence of a wild-type of the polypeptide, wherein an alteration in the sequence of the subject as compared to the wild-type indicates the presence of or a predisposition to the PUFA disorder.

The invention also teaches a method for identifying a compound which modulates a PUFA disorder, comprising identifying a compound which modulates the activity of a polynucleotide, wherein the polynucleotide is a coding sequence selected from the group consisting of ELG1, ELG2, ELG3, ELG4, ELG5, ELG6 and ELG7, comprising the steps of: (a) selecting a control animal having the polynucleotide and a test animal having the polynucleotide; (b) treating the test animal using a compound; and, (c) determining the relative quantity of an expression product of the polynucleotide, as between the control animal and the test animal.

The invention further teaches a method for identifying a compound which modulates a PUFA disorder, comprising identifying a compound which modulates the activity of a polynucleotide, wherein the polynucleotide is a coding sequence selected from the group consisting of ELG1, ELG2, ELG3, ELG4, ELG5, ELG6 and ELG7, comprising the steps of: (a) selecting a host cell having the polynucleotide, wherein the host cell is heterologous to the polynucleotide; (b) cloning the host cell and separating the clones into a test group and a control group; (c) treating the test group using a compound; and (d) determining the relative quantity of an expression product of the polynucleotide, as between the test group and the control group.

The invention further teaches a method for identifying a compound which modulates a PUPA disorder, comprising identifying a compound which modulates the activity of a polynucleotide, wherein the polynucleotide is a coding sequence selected from the group consisting of ELG1, ELG2, ELG3, ELG4, ELG5, ELG6 and ELG7, comprising the steps of: (a) selecting a test group having a host cell with the polynucleotide or a portion of the host cell, and selecting a suitable control group; (b) treating the test group using a compound; and (c) determining the relative quantity or relative activity of a product of the polynucleotide or of the polynucleotide, as between the test group and the control group.

The invention teaches a method for identifying a compound modulates a PUFA disorder, comprising identifying a compound which modulates the activity of a polypeptide selected from the group consisting of ELG1, ELG2, ELG3, ELG4, ELG5, ELG6 and ELG7, comprising the steps of: (a) selecting a control animal having the polypeptide and a test animal having the polypeptide; (b) treating the test animal using a compound; (c) determining the relative quantity or relative activity of an expression product of the polypeptide or of the polypeptide, as between the control animal and the test animal.

The invention further teaches a method for identifying a compound which modulates a PUFA disorder, comprising identifying a compound which modulates the activity of a polypeptide selected from the group consisting of ELG1, ELG2, ELG3, ELG4, ELG5, ELG6 and ELG7, comprising the steps of: (a) selecting a host cell comprising the polypeptide, wherein the host cell is heterologous to the polypeptide; (b) cloning the host cell and separating the clones into a test group and a control group; (c) treating the test group using a compound; and (d) determining the relative quantity or relative activity of an expression product of the polypeptide or of the polypeptide, as between the test group and the control group.

The invention also teaches a method for identifying a compound which modulates a PUFA disorder, comprising identifying a compound which modulates the activity of a polypeptide selected from the group consisting of ELG1, ELG2, ELG3, ELG4, ELG5, ELG6 and ELG7, comprising the steps of (a) selecting a test group having a host cell with the polynucleotide or a portion of the host cell, and selecting a suitable control group; (b) treating the test group using a compound; and (c) determining the relative quantity or relative activity of a product of the polypeptide or of the polypeptide, as between the test group and the control group.

The invention further teaches a method for identifying a compound which modulates the activity of a polynucleotide, wherein the polynucleotide is a control region of a gene selected from the group consisting of ELG1, ELG2, ELG3, ELG4, ELG5, ELG6 and ELG7, comprising the steps of: (a) selecting a control animal having the polynucleotide and a test animal having the polynucleotide; (b) treating the test animal using a compound; and, (c) determining the relative quantity of an expression product of an operably linked polynucleotide to the polynucleotide, as between the control animal and the test animal.

The animals of the invention may be mammals. The mammals may be rats.

The invention also teaches a method for identifying a compound which modulates the activity of a polynucleotide, wherein the polynucleotide is a control region of a gene selected from the group consisting of ELG1, ELG2, ELG3, ELG4, ELG5, ELG6 and ELG7, comprising the steps of: (a) selecting a host cell comprising the polynucleotide, wherein the host cell is heterologous to the polynucleotide; (b) cloning the host cell and separating the clones into a test group and a control group; (c) treating the test group using a compound; and (d) determining the relative quantity of an expression product of an operably linked polynucleotide to the polynucleotide, as between the test group and the control group.

The invention further teaches a method for identifying a compound which modulates the activity of a polynucleotide, wherein the polynucleotide is a control region of a gene selected from the group consisting of ELG1, ELG2, ELG3, ELG4, ELG5, ELG6 and ELG7, comprising the steps of: (a) selecting a test group having a host cell with the polynucleotide or a portion of the host cell, and selecting a suitable control group; (b) treating the test group using a compound; and (c) determining the relative quantity of an expression product of an operably linked polynucleotide to the polynucleotide, as between the test group and the control group.

The invention includes a composition for treating a PUFA disorder comprising a compound which modulates a polynucleotide from the coding sequence selected from the group consisting of ELG1, ELG2, ELG3, ELG4, ELG5, ELG6, and ELG7, and a pharmaceutically acceptable carrier.

The invention further teaches a composition for treating a PUFA disorder comprising a compound which modulates a polypeptide selected from the group consisting of ELG1, ELG2, ELG3, ELG4, ELG5, ELG6, and ELG7, and a pharmaceutically acceptable carrier.

The invention farther teaches a composition for treating a PUFA disorder comprising a compound which modulates a polynucleotide from the control region selected from the group consisting of ELG1, ELG2, ELG3, ELG4, ELG5, ELG6, and ELG7, and a pharmaceutically acceptable carrier.

The compound may be selected from the group consisting of antibodies against ELG1, ELG2, ELG3 and ELG5.

The invention includes method for diagnosing the presence of or a predisposition for a PUFA disorder in a subject by detecting a germline alteration in a polynucleotide representing the coding sequence selected from the group consisting of ELG1, ELG2, ELG3, ELG4, ELG5, ELG6, and ELG7, from the subject, comprising comparing the germline sequence of the polynucleotide from a tissue sample from the subject with the germline sequence of a wild-type of the polynucleotide, wherein an alteration in the germline sequence of the subject indicates the presence of or a predisposition to the PUFA disorder.

The invention also teaches method for diagnosing the presence of or a predisposition for a PUFA disorder in a subject by detecting a gemrline alteration in a polynucleotide representing the control region selected from the group consisting of ELG1, ELG2, ELG3 and ELG5 in the subject, comprising comparing the germline sequence of the polynucleotide from a tissue sample from the subject with the germline sequence of a wild-type of the polynucleotide, wherein an alteration in the germline sequence of the subject indicates the presence of or a predisposition to the PUFA disorder.

The invention also teaches a method for diagnosing the presence of or a predisposition for a PUFA disorder in a subject, comprising comparing the sequence of a polypeptide selected from the group consisting of ELG1, ELG2, ELG3, ELG4, ELG5, ELG6, and ELG7, from the subject with the sequence of a wild-type of the polypeptide, wherein an alteration in the sequence of the subject as compared to the wild-type indicates the presence of or a predisposition to the PUFA disorder.

The invention further teaches a method for identifying a compound which inhibits or promotes the overall activity of two or more polynucleotides, wherein the polynucleotides are control regions of two or more different genes selected from the group consisting of ELG1, ELG2, ELG3, ELG4, ELG5, ELG6 and ELG7, comprising the steps of: (a) selecting a host cell having the polynucleotides, wherein the host cell is heterologous to the polynucleotides;(b) cloning the host cell and separating the clones into a test group and a control group; (c) treating the test group using a compound; and (d) determining the relative quantities of expression products of operably linked polynucleotides to the polynucleotides, as between the test group and the control group.

The invention further teaches a method for identifying a compound which inhibits or promotes the overall activity of two or more polynucleotides, wherein the polynucleotides are from control regions of the polynucleotides, selected from the group consisting of ELG1, ELG2, ELG3, ELG4, ELG5, ELG6 and ELG7, comprising the steps of: (a) selecting a test group having a host cell with the polynucleotide or a portion of the host cell, and selecting a suitable control group; (b) treating the test group using a compound; and (c) determining the relative quantifies of expression products of operably linked polynucleotides to the polynucleotides, as between the test group and the control group.

The invention teaches a method for identifying a compound which inhibits or promotes the activity of two or more polynucleotides, wherein the polynucleotides are coding sequences selected from the group consisting of ELG1, ELG2, ELG3, ELG4, ELG5, ELG6 and ELG7, operably associated with promoter regions, wherein the promoter regions are effective to initiate, terminate or regulate the level of expression of the nucleic acid sequence, comprising the steps of: (a) selecting a host cell having the polynucleotides, wherein the host cell are heterologous to the polynucleotides; (b) cloning the host cell and separating the clones into a test group and a control group; (c) treating the test group using a compound; and (d) determining the relative quantity or relative activity of an expression product of the polynucleotide, as between the test group and the control group.

The invention further teaches a method for identifying a compound which inhibits or promotes the activity of two or more polynucleotides, wherein the polynucleotides are coding sequences selected from the group consisting of ELG1, ELG2, ELG3, ELG4, ELG5, ELG6 and ELG7, operably associated with promoter regions, wherein the promoter regions are effective to initiate, terminate or regulate the level of expression of the nucleic acid sequence, comprising the steps of: (a) selecting a test group having a host cell with the polynucleotide or a portion of the host cell, and selecting a suitable control group; (b) treating the test group using a compound; and (c) determining the relative quantity or relative activity of an expression product of the polynucleotide, as between the test group and the control group.

The invention includes a method for identifying a compound which inhibits or promotes the activity of a mammalian delta-5-desaturase enzyme and one or more enzymes selected from the group consisting of ELG1, ELG2, ELG3, ELG4, ELG5, ELG6 or ELG7, within the same host system, comprising the steps of: (a) providing a host system containing nucleic acid sequences which encode for a mammalian delta-5-desaturase and one or more mammalian elongase enzymes selected from the group consisting of ELG1, ELG2, ELG3, ELG4, ELG5, ELG6 or ELG7, operably associated with promoter regions, wherein the promoter regions are effective to initiate, terminate or regulate the level of expression of the nucleic acid sequence; (b) contacting the host system with a test component; (c) simultaneously evaluating the enzymatic activities of the delta-5-desaturase and the elongase enzymes, wherein a measurable difference in a level of lipid metabolites or associated cofactors in the presence of the test component compared to a control under identical conditions but in the absence of the test component is an indicator of the ability of the test component to modulate delta-5-desaturase and/or elongase enzyme activity; and (d) identifying as the compound a test component which exhibits the ability.

The invention further teaches a method for identifying a compound which inhibits or promotes the activity of a mammalian delta-6-desaturase enzyme and one or more enzymes selected from the group consisting of ELG1, ELG2, ELG3, ELG4, ELG5, ELG6 or ELG7, within the same host system, comprising the steps of: (a) providing a host system containing nucleic acid sequences which encode for a mammalian delta-6-desaturase and one or more mammalian elongase enzymes selected from the group consisting of ELG1, ELG2, ELG3, ELG4, ELG5, ELG6 or ELG7, operably associated with promoter regions, wherein the promoter regions are effective to initiate, terminate or regulate the level of expression of the nucleic acid sequence; (b) contacting the host system with a test component; (c) simultaneously evaluating the enzymatic activities of the delta-6-desaturase and the elongase enzymes, wherein a measurable difference in a level of lipid metabolites or associated cofactors in the presence of the test component compared to a control under identical conditions but in the absence of the test component is an indicator of the ability of the test component to modulate delta-6-desaturase and/or elongase enzyme activity; and (d) identifying as the compound a test component which exhibits the ability.

The invention teaches a method for identifying a compound which inhibits or promotes the activity of a mammalian delta-5- and delta-6-desaturase enzyme and/or one or more enzymes selected from the group consisting of ELG1, ELG2, ELG3, ELG4, ELG5, ELG6 or ELG7, within the same host system, comprising the steps of: (a) providing a host system containing nucleic acid sequences which encode simultaneously for a mammalian delta-5-desaturase, a mammalian delta-6-desaturase and one or more mammalian elongase enzymes selected from the group consisting of ELG1, ELG2, ELG3, ELG4, ELG5, ELG6 or ELG7, operably associated with promoter regions, wherein the promoter regions are effective to initiate, terminate or regulate the level of expression of the nucleic acid sequence; (b) contacting the host system with a test component; (c) simultaneously evaluating the enzymatic activities of the delta-5-desaturase, the delta-6desaturase and the elongase enzymes, wherein a measurable difference in a level of lipid metabolites or associated cofactors in the presence of the test component compared to a control under identical conditions but in the absence of the test component is an indicator of the ability of the test component to modulate delta-5- and/or delta-6-desaturase and/or elongase enzyme activity; and (d) identifying as the compound a test component which exhibits the ability.

The invention includes a composition for treating a PUFA disorder comprising a compound which modulates two or more human polynucleotides from control regions selected from the group consisting of ELG1, ELG2, ELG3, ELG4, ELG5, ELG6, ELG7, delta-5-desaturase, delta-6-desaturase and a pharmaceutically acceptable carrier.

The invention includes a method for detecting the presence of or the predisposition for a PUFA disorder, the method comprising determining the level of expression of two or more expression products of genes selected from the group consisting of ELG1, ELG2, ELG3, ELG4, ELG5, ELG6, ELG7, delta-5-desaturase, delta-6-desaturase, in a subject relative to a predetermined control level of expression, wherein any modified expression of the expression products as compared to the control is indicative of the presence of or the predisposition for a PUFA disorder.

The invention further includes an antibody immunoreactive with a polypeptide of the invention or an immunogenic portion thereof. The invention includes an antibody immunoreactive with an elongase polypeptide selected from the group consisting of ELG1, ELG2, ELG3, ELG4, ELG5, ELG6 and ELG7, or an immunogenic portion thereof.

The invention teaches a method for screening a medium for an elongase polypeptide of the invention or selected from the group consisting of ELG1, ELG2, ELG3, ELG4, ELG5, ELG6 and ELG7, comprising: (a) labelling an antibody of the invention with a marker molecule to form a conjugate; (b) exposing the conjugate to the medium; and (c) determining whether there is binding between the conjugate and a biomolecule in the medium, wherein the binding indicates the presence of the polypeptide.

The invention teaches a method for screening a medium for an elongase polypeptide of the invention or selected from the group consisting of ELG1, ELG2, ELG3, ELG4, ELG5, ELG6 and ELG7, comprising: (a) exposing an antibody of the invention to the medium; (b) exposing the antibody to a marker molecule; and (c) determining whether there is binding between the marker molecule and a biomolecule in the medium, wherein the binding indicates the presence of the polypeptide.

The invention includes compounds identified by the method of the inventions.

The invention further includes a method for diagnosing the presence of or a predisposition for a PUFA disorder in a subject by detecting alterations in the elongation of PUFA in a peripheral blood leukocyte obtained from the subject. The invention includes a method for monitoring the development of a PUFA disorder in a subject by detecting alterations in the elongation of PUFA in a peripheral blood leukocyte obtained from the subjects. The invention further teaches a method for assessing the effect of test compounds on a PUFA disorder in a subject by assessing alterations in the elongation of PUFA in a peripheral blood leukocyte obtained from the subject.

The compounds of the invention may be selected from the group consisting of small organic molecules, peptides, polypeptides, antisense molecules, oligonucleotides, polynucleotides, fatty acids and derivatives thereof.

The invention further teaches the use of pebulate sulphoxide for the treatment of a disorder of the invention.

The disorders of the invention may be selected from the group consisting of peripheral cardiovascular disease, coronary heart disease, hypertension, atopic eczema, rheumatoid arthritis, Sjögren's syndrome, gastrointestinal disorders, viral diseases and postviral fatigue, psychiatric disorders, pre-menstrual syndrome, endometriosis, cystic fibrosis, alcoholism, congenital liver disease, Alzheimer's syndrome, cancer, diabetes and diabetic complications. The disorders of the invention may be selected from the group consisting of eczema, cardiovascular disorders (including but not limited to hypertriglyceridemia, dyslipidemia, atherosclerosis, coronary artery disease, cerebrovascular disease hypertension, and peripheral vascular disease), inflammation (including but not limited to sinusitis, asthma, pancreatitis, osteoarthritis, rheumatoid arthritis and acne), Sjögren's syndrome, gastrointestinal disorders, viral diseases and postviral fatigue, body weight disorders (including but not limited to obesity, cachexia and anorexia), psychiatric disorders, cancer, cystic fibrosis, endometriosis, pre-menstrual syndrome, alcoholism, congenital liver disease, Alzheimer's syndrome, hypercholesterolemia, autoimnnune disorders, atopic disorders, acute respiratory distress syndrome, articular cartilage degradation, diabetes and diabetic complications.

BRIEF DESCRIPTION OF THE DRAWINGS

In the following description, the invention will be explained in detail with the aid of the accompanying figures, which illustrate preferred embodiments of the present invention and in which:

FIG. 4 is a chart showing a multiple alignment among the 7 human elongases (ELG1 (SEQ. ID. NO. 59), ELG2 (SEQ. ID. NO. 60), ELG3 (SEQ. ID. NO. 61). ELG4 (SEQ. ID. NO. 5), ELG5 (SEQ. ID. NO. 62), ELG6 (SEQ. ID. NO. 9), and ELG7 (SEQ. ID. NO. 12)), highlighting the invariant residues (marked by an asterisks), the histidine box (marked by a box) and the ER retention signals (marked by boxes);

FIG. 8 shows the nucleotide sequence of the control region of ELG1 between position −1877 and −2865 from the translation initiation codon, ATG. This figure corresponds to SEQ. ID. NO. 1;

FIG. 9 shows the nucleotide sequence of the control region of ELG2 between position −53118 and −53626 from the translation initiation codon, ATG. This figure corresponds to SEQ. ID. NO. 2;

FIG. 10 shows the nucleotide sequence of the control region of ELG3 between position −37 and −1381 from the translation initiation codon, ATG. This figure corresponds to SEQ. ID. NO. 3;

FIG. 11 shows the nucleotide sequence and amino acid sequence of the ELG4 gene. This figure corresponds to SEQ. ID. NOS. 4 and 5;

FIG. 12 shows a 2456 bp fragment of the nucleotide sequence of the control region of ELG4. This figure corresponds to SEQ. ID. NO. 6;

FIG. 13 shows the nucleotide sequence of the control region of ELG5 between position −1 and −1411 from the translation initiation codon, ATG. This figure corresponds to SEQ. ID. NO. 7;

FIG. 14 shows the nucleotide sequence and amino acid sequence of the ELG6 gene. This figure corresponds to SEQ. ID. NOS. 8 and 9;

FIG. 15 shows the nucleotide sequence of the control region of ELG6 between position −1 and −1937 from the translation initiation codon, ATG. This figure corresponds to SEQ. ID. NO. 10;

FIG. 16 shows the nucleotide sequence and amino acid sequence of the ELG7 gene. This figure corresponds to SEQ. ID. NOS. 11 and 12;

FIG. 17 shows the nucleotide sequence of the control region of ELG7 between position −1 and −2000 from the translation initiation codon, ATG. This figure corresponds to SEQ. ID. NO. 13;

DETAILED DESCRIPTION OF THE INVENTION

Figure 1:
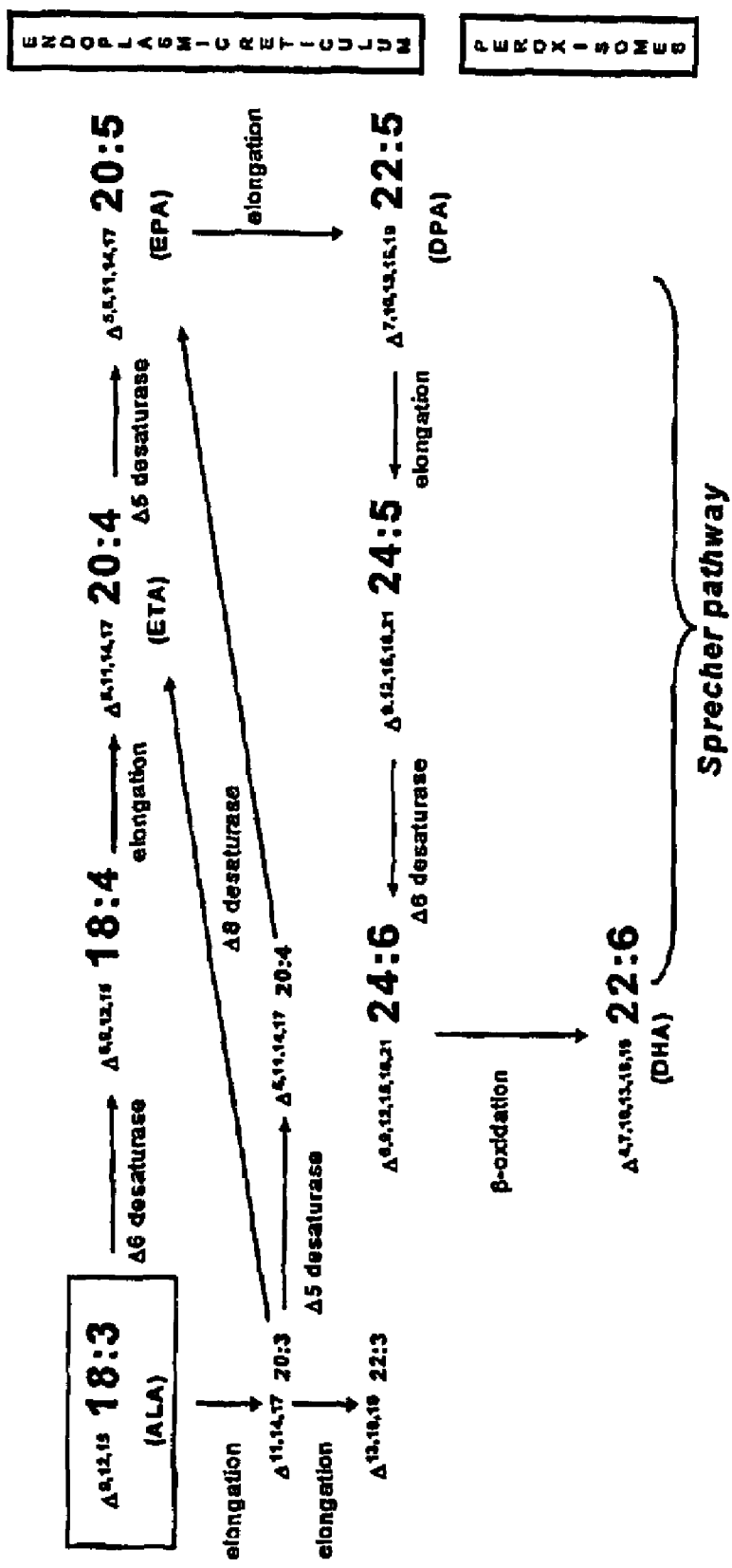
FIG. 1 is a schematic diagram of the n-3 fatty acid metabolic pathways.
Figure 2:
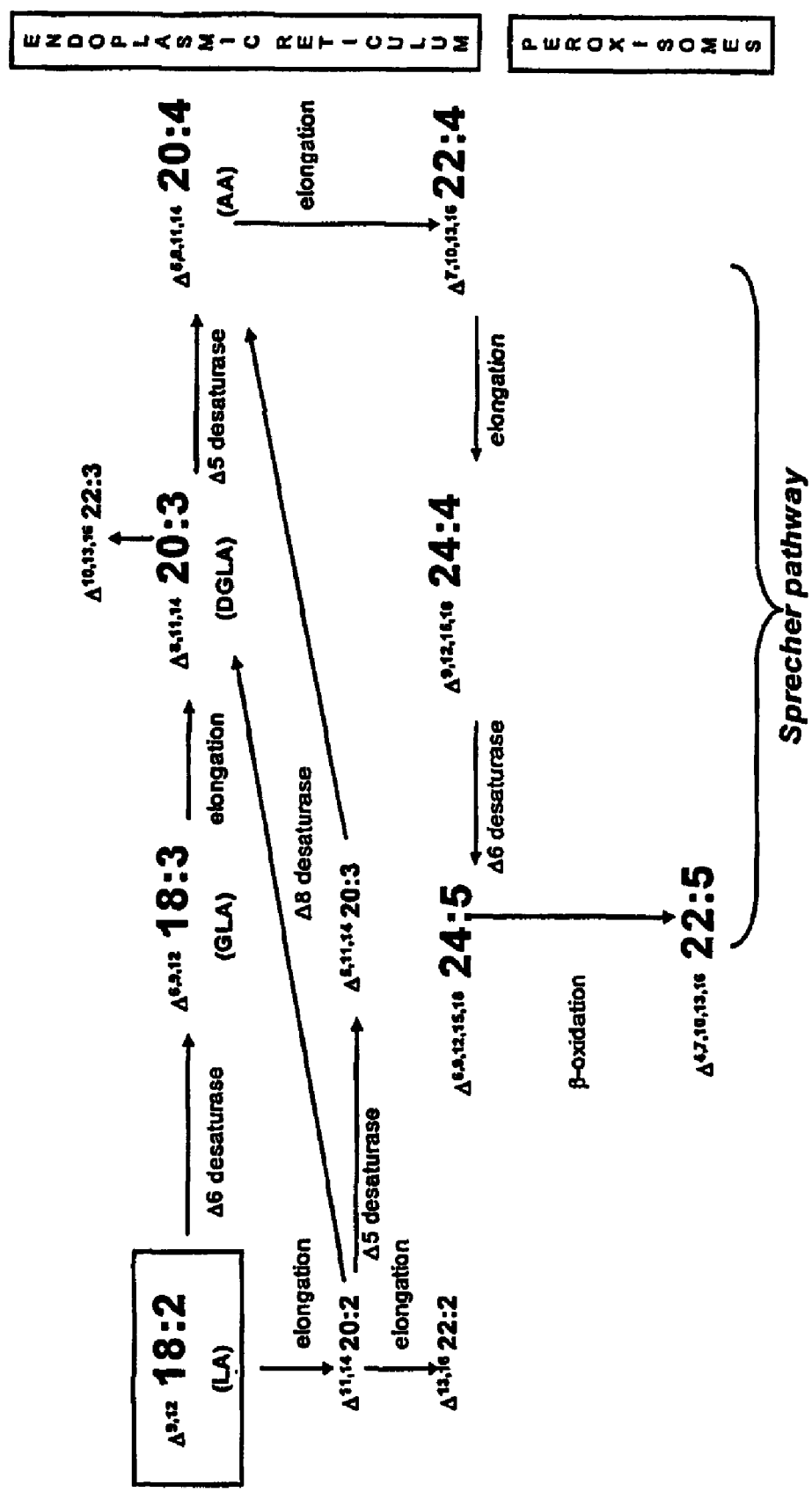
FIG. 2 is a schematic diagram of the n-6 fatty acid metabolic pathways.
Figure 3:
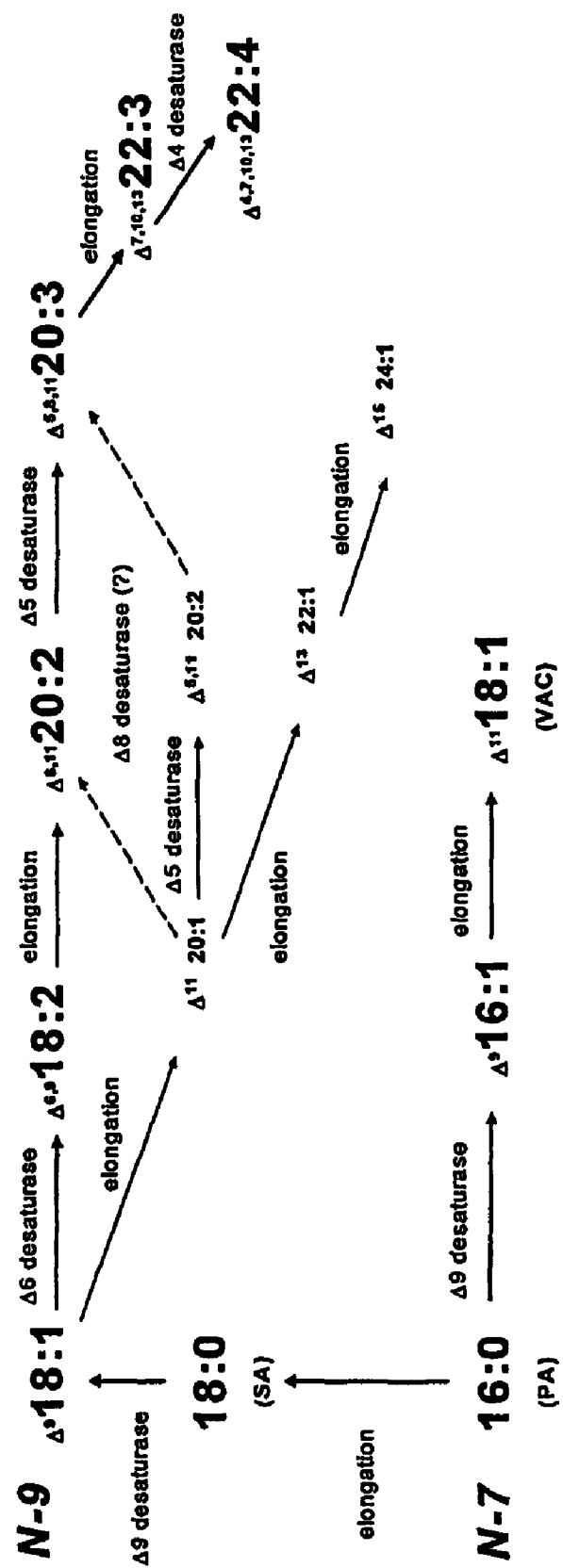
FIG. 3 is a schematic diagram of the n-9 and n-7 fatty acid metabolic pathways.

As mentioned above, research has indicated that increased levels of LA or DGLA are the result of decreased activities of delta-6 and delta-5-desaturase enzymes. The present inventors have found evidence that both the desaturase and elongase activities are affected in a PUFA related disorder.

The desaturase and elongase enzyme activities in liver microsomes from streptozotocin (STZ)-induced diabetic rats was assayed at 2 and 7 weeks post-induction. Table 1 indicates the decrease in activities compared to a control, observed during the course of the experiment. An equivalent decrease in elongation activity in STZ-induced diabetic rats has been previously reported (Suneja et al., 1990, *Biochim. Biophys. Acta*, 1042: 81-85).

TABLE 1

Percent Decrease of the Desaturase and Elongase Activities in Liver Microsomes from STZ-Induced Diabetic Rats

| | % Decrease | |
| --- | --- | --- |
| ENZYME | 2 weeks | 7 weeks |
| D6D (18:2n-6 → 18:3n-6) | 28 | 33 |
| Elongase (18:3n-6 → 20:3n-6) | 46 | 43 |
| D5D (20:3n-6 → 20:4n-6) | 33 | 41 |

This data, when considered in view of what is known regarding the relationship between PUFAs and disease (above), indicates that elongase genes are involved in the development and regulation of lipid associated diseases such as inflammation, hypercholesterolemia, autoimmune disorders, atopic disorders, cystic fibrosis, psychiatric disorders, acute respiratory distress syndrome, articular cartilage degradation, arthritis, diabetes and diabetic complications. Since PUFAs are involved in a number of cell regulatory processes, the elongase genes and gene products represent realistic drug targets for the treatment or prevention of fatty acid associated diseases.

The present inventors used bioinformatic techniques to identify and analyze 7 human elongase genes (ELG1, ELG2, ELG3, ELG4, ELG5, ELG6 and ELG7). The amino acid sequences of the 7 human elongases were compared using a ClustalW algorithm (Thompson et al., 1994, *Nucl. Acids Res.*, 22: 4673-4680). One highly conserved motif, a histidine box containing 3 histidine residues, found also in a number of membrane-bound desaturases, is common to all 7 sequences. Twenty five other invariant residues, suggesting their critical importance in the catalytic activity and structure of the elongases, are identified in the multiple alignment where they are indicated by asterisk (see FIG. 4).

Table 2 shows the percent identity among the 7 human elongases. The percent identities range from a low of 17% (ELG3/ELG5 and ELG3/ELG6) to a high of 55% (ELG1/ELG4).

TABLE 2

Percent Identities Among the 7 Human Elongases

|      | ELG1 | ELG2 | ELG3 | ELG4 | ELG5 | ELG6 | ELG7 |
|------|------|------|------|------|------|------|------|
| ELG1 | 100  |      |      |      |      |      |      |
| ELG2 | 30   | 100  |      |      |      |      |      |
| ELG3 | 29   | 54   | 100  |      |      |      |      |
| ELG4 | 55   | 31   | 34   | 100  |      |      |      |
| ELG5 | 18   | 18   | 17   | 22   | 100  |      |      |
| ELG6 | 21   | 18   | 17   | 22   | 43   | 100  |      |
| ELG7 | 33   | 37   | 37   | 36   | 18   | 19   | 100  |

Figure 5:
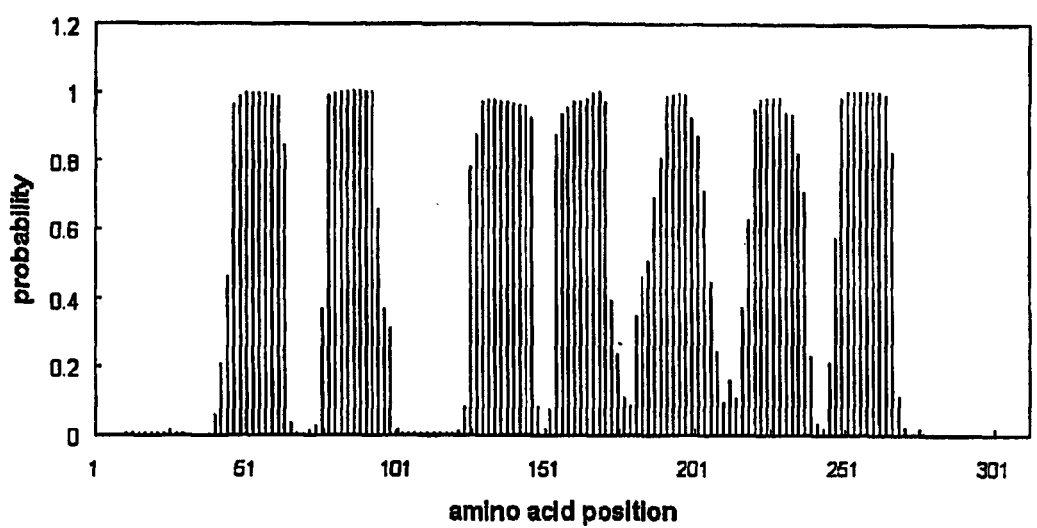
FIG. 5 is a graph illustrating the Transmembrane Hidden Markov Model (TMHMM) prediction for transmembrane regions for ELG7.
Figure 6:
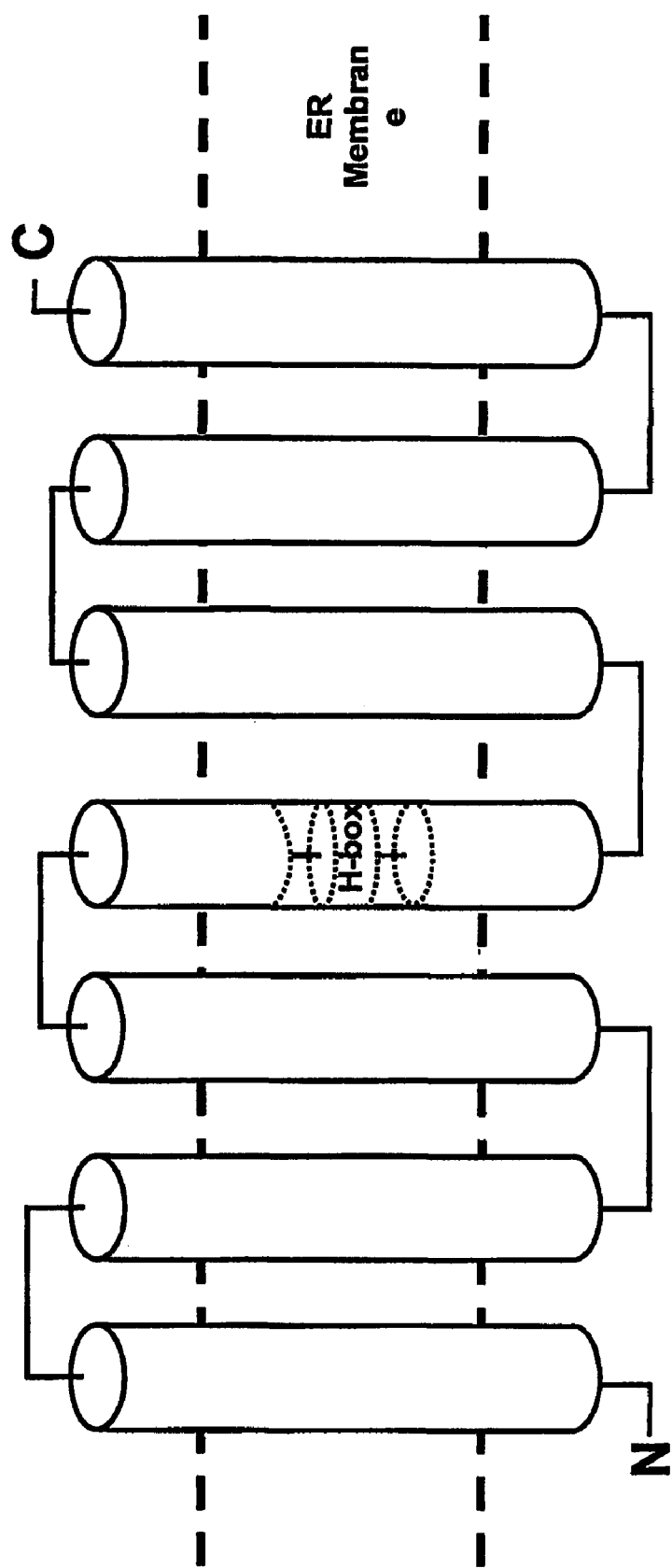
FIG. 6 is a diagram showing a topological model of a human elongase embedded in the endoplasmic reticulum.

Based on a hidden Markov model for predicting transmembrane regions (Sonnhammer et al., 1998, In *Proc. of Sixth Int. Conf. on Intelligent Systems for Molecular Biology*, AAAI Press, CA, pp. 175-182), this family of seven elongases has 7 membrane spanning regions (FIG. 5). These regions are highly conserved with respect to position in the amino acid sequences of the 7 elongases. The invariant histidine box is predicted to be embedded in the fourth transmembrane region. This differs from that of the membrane-bound desaturases wherein the three conserved histidine boxes are predicted to be in cytosolic loops (Shanklin et al., 1994, *Biochemistry*, 33: 12787-12794). The present model for the human elongases encompasses a ring of transmembrane domains enclosing an inner catalytic cavity for insertion of fatty acyl chains. A proposed topological model of the elongases embedded in the endoplasmic reticulum (ER) is shown in FIG. 6.

The present inventors have discovered that each of the proteins has an ER retention signal (Jackson et al., 1990, *EMBO J.*, 9: 3153-3162 and Nilsson T. and Warren G., 1994, *Curr. Opin. Cell Biol.*, 6: 517-521) at the carboxyl terminus. In ER resident proteins with a type I topology (amino terminus in the lumen), the signal has been shown to consist of two critical lysines, which are in a –3 and a –4/–5 position relative to the carboxyl terminus in their cytosolic, exposed tails (K[X]KXX, where X is any amino acid). Each of the elongases has such a retention signal. Both ELG2 and ELG5, however, have modified forms of this signal wherein the two critical lysines are found at positions –2 and –5, and –3 and –6, respectively. (FIG. 4).

ELG1 Gene and Polypeptide

BLASTP of the GenBank NR database with yeast ELO1 identified a protein with unknown function, CGI-88, as a potential elongase (GenBank Accession No. AAD34083). Initial cloning indicated that the cDNA sequence from which this protein was deduced (GenBank Accession No. AF151846) has a one base deletion at position 566 of the CDS. The present inventors' clone has an extra C residue at position 566 in the CDS which results in a protein, termed ELG1 by the present inventors, with a different, and longer, C-terminus than CGI-88. Since then, a gene (GenBank Accession No. AK001653) coding for a protein with no assigned function, which differs from ELG1 by one amino acid, has been submitted to GenBank (Accession No. BAA91813). The deduced amino acid sequence of ELG1 contains a F68S substitution.

Figure 7:
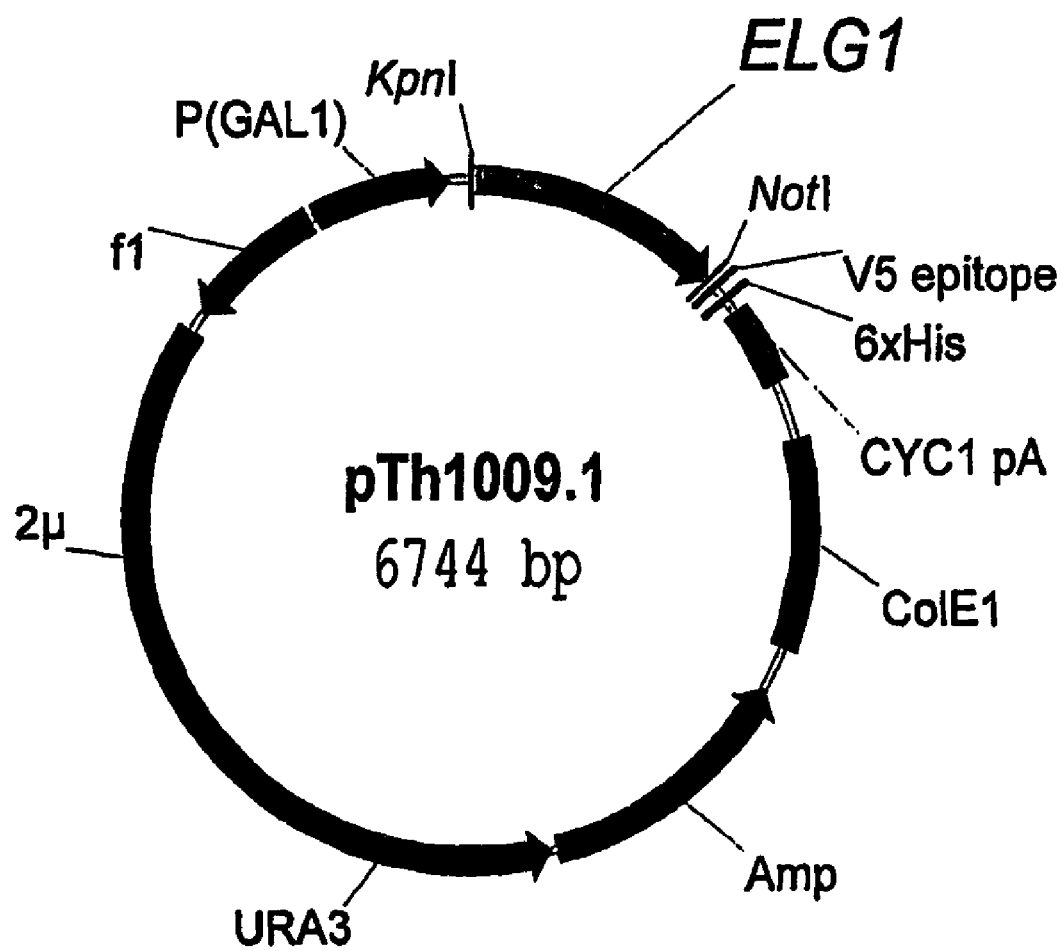
FIG. 7 is a schematic representation of plasmid pTh1009.1 (6744 bp). The human elongase (ELG1) coding sequence is shown between restriction sites for KpnI and NotI.

The cDNA coding for ELG1 was obtained by PCR and cloned into the yeast expression vector pYES2/CT. The nucleotide sequence was verified by DNA sequencing and the resulting plasmid was designated pTh1009.1 (FIG. 7).

Yeast cells transformed with pTh1009.1 and expressing ELG1 were shown to convert 18:3n-6 to 20:3n-6, 20:4n-6 to 22:4n-6 and 24:4n-6, 18:3n-3 to 20:3n-3, and 20:5n-3 to 22:5n-3 (refer to Table 3 in Example 19). Yeast cells transformed with the pYES2/CT vector did not elongate any of these substrates. This proved that the ELG1 gene encodes a PUFA elongase. There is no published data demonstrating that this protein is a PUFA elongase. Mukerji et al. (PCT Application WO 00/12720) indicate that this protein, referred to as HS2, might be a PUFA elongase. They did not clone the coding sequence nor determine function.

The mouse ortholog of human ELG1, Ssc1 (GenBank Accession No. AF170907), has been implicated in fatty acid elongation due to its ability to complement yeast ELO mutants. Furthermore, Ssc1 gene expression correlates with elongase activity in brains of myelin-deficient mouse mutants (Tvrdik et al., 2000, *J. Cell Biol.*, 149: 707-717). Mouse Ssc1 is 92% identical and 97% similar to human ELG1.

Exons for ELG1 were mapped onto genomic DNA from human chromosome 1 (GenBank Accession No. AL139289). The gene was found to comprise 7 coding exons spanning 1.7 kb.

Using bioinformatic techniques, the control region of the ELG1 gene was identified and mapped out. By searching GenBank's EST division using BLASTN with genomic DNA and CDS for the ELG1 gene, a number of different ESTs were identified containing 5' UTR for the gene. There were 2 families of such ESTs each arising from different upstream exons which exclusively contain 5' UTR. The first exon has its 3' position at –2306 while the second exon has its 3' position at –1877 from the translation initiation codon, ATG. A 128 bp fragment of another EST (GenBank Accession No. AM373530) was also identified approximately 2.9 kb upstream of the ATG. The control region between positions –1877 and –2865 from the translation initiation codon, ATG is shown in FIG. 8. A repetitive element is further identified upstream of –3600.

Northern blot studies evaluating tissue distribution showed that the ~1.3 kb ELG1 transcript is expressed in all tissues examined, with highest levels in kidney, brain, heart and placenta.

ELG2 Gene and Polypeptide

BLASTP of the GenBank NR database with yeast ELO1 identified a protein with unknown function (GenBank Accession No. CAB41293, since withdrawn) as a potential elongase. This protein sequence was deduced from genomic DNA (GenBank Accession No. AL034374) and represents only a partial sequence. Using GeneTrapper technology (Gibco BRL) the complete coding sequence of this protein, termed ELG2 by the present inventors, was cloned and the nucleotide sequence determined by DNA sequencing. Since then, the ELG2 coding sequence and deduced protein sequence have been submitted to GenBank (Accession Nos. AF231981 and AAF70631, respectively).

The cDNA coding for ELG2 was obtained by PCR and cloned into the yeast expression vector pYES2/CT. The sequence was verified by DNA sequencing and the resulting plasmid was designated pTh1014.1.

Yeast cells transformed with pTh1014.1 and expressing ELG2 were shown to elongate 18:3n-6 to 20:3n-6 and 22:3n-6, 20:4n6 to 22:4n-6 and 24:4n-6, 18:3n-3 to 20:3n-3, and 20:5n-3 to 22:5n-3 (refer to Table 3 in Example 19). Yeast transformed with the pYES2/CT vector did not elongate any of these substrates. This proved that the ELG2 gene encodes a PUFA elongase. It has been reported that this gene, referred to as HELO or HSELO, encodes a protein that is involved in the elongation of a variety of PUFAs including 18:3n-6, 20:4n-6, 18:4n-3, 20:5n-3 and 18:3n-3 (Leonard et al., 2000, *Biochem. J.*, 350: 765-770 and Mukerji et al., PCT Application WO 00/12720).

Exons for ELG2 were mapped onto genomic DNA from human chromosome 6 (GenBank Accession No. AL034374). The gene was found to comprise 7 coding exons spanning 26.5 kb.

Using bioinformatic techniques, the control region of the ELG2 gene was identified and mapped out. Using sequence data from the present inventors' clones obtained by GeneTrapper technology, 5' UTR was identified in an exon approximately 53 kb upstream of the ATG. This finding was corroborated by searching GenBank's EST division using BLASTN with the ELG2 CDS. Two ESTs were identified (GenBank Accession Nos. AA282396 and BE779576), which mapped to the same upstream exon. The control region between positions -53118 and -53626 from the translation irritation codon, ATG is shown in FIG. 9. Sequence from which an EST is derived (GenBank Accession No. AA557341) lies immediately upstream of this region. A repetitive element is identified approximately 1.4 kb further upstream from the 3' end of this 5' UTR-containing exon.

Northern blot studies evaluating tissue distribution showed that the ~2.8 kb ELG2 transcript is expressed in all tissues examined, with highest levels in brain, heart and kidney, and moderate levels in the liver.

ELG3 Gene and Polypeptide

BLASTP of the GenBank NR database with yeast ELO1 identified a protein with unknown function (GenBank Accession No. BAA91096), as a potential elongase. This protein was deduced from cDNA (GenBank Accession No. AK000341) and is termed ELG3 by the present inventors.

The cDNA coding for ELG3 was obtained by PCR and cloned into the yeast expression vector pYES2/CT. The nucleotide sequence was verified by DNA sequencing and the resulting plasmid was designated pTh1015.1. In comparison to GenBank Accession No. BAA91096, the protein encoded by the ELG3 gene contains two amino acid substitutions, T31M and V179I.

Yeast cells transformed with pTh1015.1 and expressing ELG3 were shown to elongate 18:3n-6 to 20:3n-6, 20:4n-6 to 22:4n-6 and 24:4n-6, 18:3n-3 to 20:3n-3, and 20:5n-3 to 22:5n-3 and 24:5n-3 (refer to Table 3 in Example 19). Yeast transformed with the pYES2/CT vector did not elongate any of these substrates. This proved that ELG3 encodes a PUFA elongase. There is no published data demonstrating that this protein is a PUFA elongase. However, Mukerji et al. (PCT Application WO 00/12720) indicate that an EST (GenBank Accession No. AI815960), found by the present inventors to represent a portion of the CDS of ELG3, may encode a partial PUFA elongase. They did not clone the coding sequence derived from this EST nor determine its function.

The mouse ortholog of human ELG3, Ssc2 (GenBank Accession No. AF170908), has been identified as putatively involved in fatty acid elongation. However, enzymatic function has not been confirmed (Tvrdik et al., 2000, *J. Cell Biol.*, 149: 707-717). Mouse Ssc2 is 88% identical and 94% similar to human ELG3.

Exons for ELG3 were mapped onto genomic DNA from human chromosome 6 (GenBank Accession No. AL121955). The gene was found to comprise 8 coding exons spanning 60.5 kb.

Using bioinformatic techniques, the control region of the ELG3 gene was identified and mapped out. By searching GenBank using BLASTN with genomic DNA and CDS for the ELG3 gene, 2 sequences (GenBank Accession Nos. BE778035 and AK000341) were identified containing 84 bp of 5' UTR immediately upstream of the initiation codon, ATG. The control region between positions -37 and -1381 from the translation initiation codon, ATG was cloned (see Example 11) and is shown in FIG. 10.

Northern blot studies evaluating tissue distribution showed that the ~4.4 kb ELG3 transcript is moderately expressed in brain, with lower levels in heart, liver and placenta. This transcript was not detected in any of the other tissues examined.

ELG4 Gene and Polypeptide

BLASTP of the GenBank NR database with yeast ELO1 identified a protein with unknown function (GenBank Accession No. CAB70777) as a potential elongase. This protein sequence was deduced from cDNA (GenBank Accession No. AL137506) and represents only a partial sequence. Using GeneTrapper technology (Gibco BRL) and PCR amplification the full coding sequence for this protein, termed ELG4 by the present inventors, was cloned. The cDNA sequence was determined by DNA sequencing. The coding sequence and amino sequence of ELG4 are shown in FIG. 11. Since then, Kawakami and coworkers have submitted a cDNA sequence to GenBank (Accession No. AK027216) that is similar to ELG4. However, in comparison to ELG4 it does not contain the first 31 nucleotides of the coding sequence, has several nucleotide substitutions and has a one nucleotide insertion.

The cDNA coding for ELG4 was obtained by PCR and cloned into the yeast expression vector pYES2/CT. The sequence was verified by DNA sequencing and the resulting plasmid was designated pTh1021.1.

Figure 21:
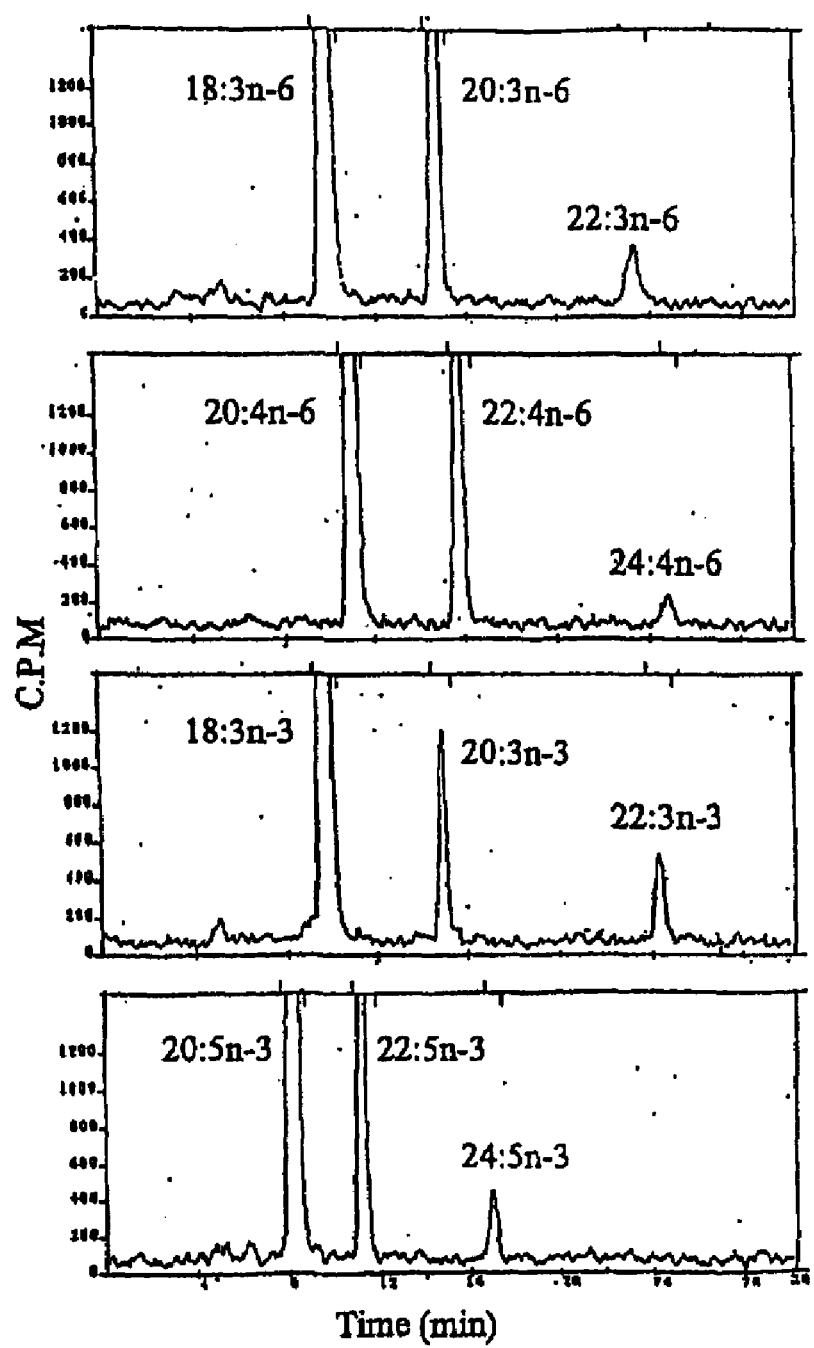
FIG. 21 shows an HPLC analysis of radiolabelled methyl esters of fatty acids from yeast transformed with pTh1021.1 incubated with [1-$^{14}$C]18:3n-6, [1-$^{14}$C]20:4n-6, [1-$^{14}$C]18:3n-3 and [1-$^{14}$C]20:5n-3.

Yeast cells transformed with pTh1021.1 and expressing ELG4 were shown to elongate 18:3n-6 to 20:3n-6 and 22:3n-6, 20:4n-6 to 22:4n-6 and 24:4n-6, and 18:3n-3 to 20:3n-3 and 22:3n-3, and 20:5n-3 to 22:5n-3 and 24:5n-3 (Refer to Table 3 in Example 19 and FIG. 21). Yeast transformed with the pYES2/CT vector did not elongate any of these substrates. This proved that the ELG4 gene encodes a PUFA elongase.

Exons for ELG4 were mapped onto genomic DNA from human chromosome 5 (GenBank Accession No.

AC021601). The gene was found to comprise 7 coding exons spanning at least 32 kb.

Using bioinformatic techniques, the control region of the ELG4 gene was identified and mapped out. Using sequence data from the present inventors' clones obtained by GeneTrapper technology, the 5' UTR was identified in 3 consecutive, alternatively spliced, upstream exons from the exon containing the initiation codon, ATG. The most immediate upstream exon is approximately 12 kb upstream, the next exon is over 13 kb upstream and the farthest upstream exon is at least 19 kb upstream from the ATG. The control region containing a 2456 bp fragment with its end at the 3' end of this first (most upstream) exon is shown in FIG. 12. It is flanked at its 5' end by a repetitive element.

Northern blot studies evaluating tissue distribution showed that the ~4.3 kb ELG4 transcript is highly expressed in kidney and moderately expressed in brain and heart. Low levels of transcript were detected in skeletal muscle, colon, thymus, liver, small intestine and placenta. The transcript was not detected in spleen and peripheral blood leukocytes.

ELG5 Gene and Polypeptide

The cDNA sequence of a GenBank entry (Accession No. AK027031) encodes another potential elongase. The deduced protein sequence (GenBank Accession No. BAB15632) is termed ELG5 by the present inventors.

The cDNA coding for ELG5 was obtained by PCR and cloned into the yeast expression vector pYES2/CT. The nucleotide sequence was verified by DNA sequencing and the resulting plasmid was designated pTh1018.1.

Yeast cells transformed with pTh1018.1 and expressing ELG5 were shown to convert 18:3n-6 to 20:3n-6 and 18:3n-3 to 20:3n-3 (refer to Table 3 in Example 19). Yeast cells transformed with the pYES2/CT vector did not elongate either of these substrates. This proved that the ELG5 gene encodes a PUFA elongase. There is no published data demonstrating that this protein is a PUFA elongase. Mukerji et al. (PCT Application WO 00/12720) indicate that HS3, which is identical to ELG5, might be a PUFA elongase. The coding sequence was cloned, however, enzymatic function was not evaluated.

Exons for ELG5 were mapped onto genomic DNA from human chromosome 4 (GenBank Accession Nos. AC004050, AC022952 and AP002080). The gene was found to comprise 4 coding exons spanning at least 88 kb.

Using bioinformatic techniques, the control region of the ELG5 gene was identified and mapped out. By searching GenBank's EST division using BLASTN with genomic DNA and CDS for the ELG5 gene, a number of different ESTs were identified containing 5' UTR for the gene. The control region between positions −1 and −1411 from the ATG is shown in FIG. 13. This region is flanked at its 5' end by a repetitive element.

Northern blot studies evaluating tissue distribution showed two transcripts for ELG5 (FIG. 27). The ~3.0 kb transcript is highly expressed in liver, with moderate expression in brain, colon and kidney, and low expression in heart, thymus, small intestine, placenta and skeletal muscle. The ~7.6 kb transcript is expressed in moderate levels in the brain and low levels in colon, kidney and liver.

ELG6 Gene and Polypeptide

ELG6 was identified by searching Homo sapiens sequences in GenBank's HTGS division with the coding sequences for ELG1, ELG2, ELG3, ELG4 and ELG5 using the TBLASTN algorithm. One sequence was identified as containing sequences similar to human elongases (GenBank Accession No. AL160011). This approach, however, failed to identify the beginning of the gene containing the translation initiation site. Therefore, further mapping and identification of ELG6 coding sequences was obtained using Cig30 (cold inducible membrane glycoprotein 30) from Mus musculus (GenBank Accession No. U97107), a protein found to be similar to ELG6, as a template. The first coding exon of ELG6 containing the initiation codon, ATG, was identified in this manner.

The cDNA coding for ELG6 was obtained by PCR and cloned into the yeast expression vector pYES/CT. The nucleotide sequence was verified by DNA sequencing and the resulting plasmid was designated pTh1041.1. The coding sequence and amino sequence of ELG6 are shown in FIG. 14.

Yeast cells transformed with pTh1041.1 and expressing ELG6 were shown to elongate 18:3n-6 to 20:3n-6 and 18:3n-3 to 20:3n-3 (refer to Table 3 in Example 19). Yeast cells transformed with the pYES2/CT vector did not elongate either of these substrates. This proved that the ELG6 gene encodes a PUFA elongase.

The mouse ortholog of human ELG6, Cig30 (GenBank Accession No. U97107), has been implicated in fatty acid elongation due to its ability to complement yeast ELO2 mutants. Furthermore, Cig30 gene expression correlates with elongase activity during brown fat recruitment in mice (Tvrdik et al., 1997, *J. Biol. Chem.*, 272: 31738-31746 and Tvrdik et al., 2000, *J. Cell Biol.*, 149: 707-717). Mouse Cig30 is 69% identical and 81% similar to human ELG6.

Since the inventors' discovery of ELG6 another record has been submitted to GenBank (GenBank Accession No. AF292387) containing genomic DNA and a partial CDS for the Homo sapiens Cig30 ortholog. Sequence annotations, however, do not indicate the presence of the first coding exon.

Exons for ELG6 were mapped onto genomic DNA from human chromosome 10 (GenBank Accession No. AL160011). The gene was found to comprise 4 coding exons spanning approximately 2.7 kb.

Using bioinformatic techniques, the control region of the ELG6 gene was identified and mapped out. The control region between positions −1 and −1937 from the ATG is shown in FIG. 15.

The transcript for ELG6 was not detected in standard Northern blot analysis in any of the tissues examined.

ELG7 Gene and Polypeptide

ELG7 was identified by searching Homo sapiens sequences in GenBank's HTGS division with the coding sequences for ELG1, ELG2, ELG3, ELG4 and ELG5 using the TBLASTN algorithm. A number of sequences were identified containing exons with sequences similar to human elongases. One such sequence, 164 kb in length, (GenBank Accession No. AL132875) was found by the present inventors to contain a previously unidentified gene, termed ELG7, in 6 coding exons spanning approximately 30.5 kb of genomic DNA.

The cDNA coding for ELG7 was obtained by PCR and cloned into the yeast expression vector pYES2/CT. The nucleotide sequence was verified by DNA sequencing and the resulting plasmid was designated pTh1044.1. The coding sequence and amino sequence of ELG7 are shown in FIG. 16.

Yeast cells transformed with pTh1044.1 and expressing ELG7 were shown to convert 18:3n-3 to 20:3n-3 (refer to Table 3 in Example 19). Yeast transformed with the pYES2/CT vector did not elongate this substrate. This proved that ELG7 encodes a PUFA elongase.

Using bioinformatic techniques, the control region of the ELG7 gene was identified and mapped out. By searching GenBank's EST division using BLASTN with genomic DNA for the ELG7 gene, a human EST containing 118 bp of 5' UTR for the gene was identified immediately upstream of the initiation codon, ATG (GenBank Accession No. BE878648). The control region between positions −1 and −2000 from the ATG is shown in FIG. 17. A repetitive element is further identified upstream of −2700.

Northern blot studies evaluating tissue distribution showed that the 3.0 kb ELG7 transcript is expressed in brain, thymus and placenta. This transcript was not detected in any of the other tissues examined.

Subject Polynucleotides and Polypeptides

The subject polynucleotides and polypeptides may be employed as research reagents and materials for discovery of treatments of and diagnostics for disease, particularly human disease, as further discussed herein.

Nucleotide Probes

The nucleic acid molecules of the invention allow those skilled in the art to construct nucleotide probes for use in the detection of nucleotide sequences in biological materials. As described herein, a number of unique restriction sequences for restriction enzymes are incorporated in the nucleic acid molecule identified in the sequence listings of the subject polynucleotides, and these provide access to nucleotide sequences which code for polypeptides unique to the subject polynucleotides of the invention. Nucleotide sequences unique to the subject polynucleotides or isoforms thereof can also be constructed by chemical synthesis and enzymatic ligation reactions carried out by procedures known in the art.

A nucleotide probe may be labeled with a detectable marker such as a radioactive label which provides for an adequate signal and has sufficient half-life such as $^{32}P$, $^{3}H$, $^{14}C$ or the like. Other detectable markers which may be used include antigens that are recognized by a specific labeled antibody, fluorescent compounds, enzymes, antibodies specific for a labeled antigen, and chemiluminescent compounds. An appropriate label may be selected with regard to the rate of hybridization and binding of the probe to the nucleotide to be detected and the amount of nucleotide available for hybridization. The nucleotide probes may be used to detect genes related to or analogous to the subject polynucleotides of the invention.

Accordingly, the present invention also provides a method of detecting the presence of nucleic acid molecules encoding a polypeptide related to or analogous to the subject polynucleotides in a sample comprising contacting the sample under hybridization conditions with one or more of the nucleotide probes of the invention labeled with a detectable marker, and determining the degree of hybridization between the nucleic acid molecule in the sample and the nucleotide probes.

Hybridization conditions which may be used in the method of the invention are known in the art and are described for example in Sambrook et al., 1989, *Molecular Cloning, 2nd Edition*, Cold Spring Harbor Laboratory Press, Cold Spring Harbour, N.Y. The hybridization product may be assayed using techniques known in the art. The nucleotide probe may be labeled with a detectable marker as described herein and the hybridization product may be assayed by detecting the detectable marker or the detectable change produced by the detectable marker.

Primers

The identification of the nucleic acid molecule of the invention also permits the identification and isolation, or synthesis of nucleotide sequences which may be used as primers to amplify a polynucleotide molecule of the invention, for example in polymerase chain reaction (PCR). The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length.

Primers which may be used in the invention are oligonucleotides i.e. molecules containing two or more deoxyribonucleotides of the nucleic acid molecule of the invention which occur naturally as in a purified restriction endonuclease digest or are produced synthetically using techniques known in the art such as, for example, phosphotriester and phosphodiester methods or automated techniques (Connolly B. A., 1987, *Nucl. Acid Res.*, 15: 3131-3139). The primers are capable of acting as a point of initiation of synthesis when placed under conditions which permit the synthesis of a primer extension product which is complementary to the DNA sequence of the invention e.g. in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer may be single or double-stranded. When the primer is double-stranded it may be treated to separate its strands before using it to prepare amplification products. The primer preferably contains between about 7 and 25 nucleotides.

The primers may be labeled with detectable markers which allow for detection of the amplified products. Suitable detectable markers are radioactive markers such as $^{32}P$, $^{35}S$, $^{125}I$ and $^{3}H$, luminescent markers such as chemiluminescent markers, preferably luminol and fluorescent markers, preferably dansyl chloride, fluorescein-5-isothiocyanate and 4-fluor-7-nitrobenz-2-oxa-1,3diazole and cofactors such as biotin. It will be appreciated that the primers may contain non-complementary sequences provided that a sufficient amount of the primer contains a sequence which is complementary to a nucleic acid molecule of the invention or oligonucleotide sequence thereof, which is to be amplified. Restriction site linkers may also be incorporated into the primers allowing for digestion of the amplified products with the appropriate restriction enzymes facilitating cloning and sequencing of the amplified product.

Assays—Amplifying Sequences

Thus, a method of determining the presence of a nucleic acid molecule having a sequence encoding the subject polynucleotides or a predetermined oligonucleotide fragment thereof in a sample, is provided comprising treating the sample with primers which are capable of amplifying the nucleic acid molecule or the predetermined oligonucleotide fragment thereof in a polymerase chain reaction to form amplified sequences, under conditions which permit the formation of amplified sequences and, assaying for amplified sequences.

The polymerase chain reaction refers to a process for amplifying a target nucleic acid sequence as generally described in Innis M. A. and Gelfand D. H., 1989, PCR Protocols, A Guide to Methods and Applications, Innis M. A., Gelfand D. H., Shinsky J. J. and White T. J. (eds), Academic Press, New York, pp. 3-12, which are incorporated herein by reference. Conditions for amplifying a nucleic acid template are described in Innis M. A. and Gelfand D. H., 1989, PCR Protocols, A Guide to Methods and Applications, Innis M. A., Gelfand D. H., Shinsky J. J. and White T. J. (eds), Academic Press, New York, pp. 3-12, which is also incorporated herein by reference.

The amplified products can be isolated and distinguished based on their respective sizes using techniques known in the art. For example, after amplification, the DNA sample can be separated on an agarose gel and visualized, after staining with ethidium bromide, under ultraviolet (UV) light. DNA may be amplified to a desired level and a further extension reaction may be performed to incorporate nucleotide derivatives having detectable markers such as radioactive labeled or biotin labeled nucleoside triphosphates. The primers may also be labeled with detectable markers. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see Innis M. A. and Gelfand D. H., 1989, PCR Protocols, A Guide to Methods and Applications, Innis M. A., Gelfand D. H., Shinsky J. J. and White T. J. (eds), Academic Press, New York, pp. 3-12, which is incorporated herein by reference. Preferably, the PCR utilizes polymerase obtained from thermophilic bacterium *Thermus aquaticus* (Taq polymerase, GeneAmp Kit, Perkin Elmer Cetus) or other thermostable polymerase may be used to amplify DNA template strands.

It will be appreciated that other techniques such as the Ligase Chain Reaction (LCR) and Nucleic-Acid Sequence Based Amplification (NASBA) may be used to amplify a nucleic acid molecule of the invention. In LCR, two primers which hybridize adjacent to each other on the target strand are ligated in the presence of the target strand to produce a complementary strand (Backman, 1991 and European Published Application No. 0320308, published Jun. 14, 1989). NASBA is a continuous amplification method using two primers, one incorporating a promoter sequence recognized by an RNA polymerase and the second derived from the complementary sequence of the target sequence to the first primer (U.S. Pat. No. 5,130,238 to Malek).

Vectors

The present invention also teaches vectors which comprise a polynucleotide or polynucleotides of the present invention, host cells which are genetically engineered with vectors of the invention and the production of polynucleotides of the invention by recombinant techniques.

In accordance with this aspect of the invention the vector may be, for example, a plasmid vector, a single or double-stranded phage vector, or a single or double-stranded RNA or DNA viral vector. In certain embodiments in this regard, the vectors provide for specific expression. Such specific expression may be inducible expression or expression only in certain types of cells or both inducible and cell-specific. Particular among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art. Such vectors include, among others, chromosomal, episomal and virus-derived vectors, e.g., vectors derived from bactial plasmids, from bacteriophage, from transposons, from yeast episomes, from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All of these may be used for expression in accordance with this aspect of the present invention.

The following vectors, which are commercially available, are provided by way of example. Among vectors for use in bacteria are pQE-9, pQE-16, pQE-30, pQE40, pQE-50 and pQE-60 (Qiagen); pCRII, PCRII-TOPO, pTrcHis and pBAD-TOPO (Invitrogen); pGEM-3Z, pGEMEX-1, pET-5 (Promega); pBS phagemid vectors, Phagescript vectors, Bluescript vectors, pCAL, pET-3 and pSPUTK (Stratagene); pTrc99A, pKK223-3, pKK232-8 and pRIT2T (Pharmacia); pMAL (New England Biolabs); and pBR322 (ATCC 37017). Among eukaryotic vectors are pGAPZ, pYES2, pYES2/CT and pcDNA3.1 (Invitrogen); pCAT3 and pGL3 (Promega); pCMV-Script, pXT1, pDual, pCMVLacI, pESC, HybriZAP2.1, ImmunoZAP and pRS (Stratagene); and pSVK3, pSVL and pMSG (Pharmacia). These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention. Generally, any vector suitable to maintain, propagate or express polynucleotides to express a polypeptide or polynucleotide in a host may be used for expression in this regard.

The DNA sequence in the expression vector is operatively linked to appropriate expression control sequence(s), including, for instance, a promoter to direct mRNA transcription. Promoter regions can be selected from any desired gene using vectors that contain a reporter transcription unit lacking a promoter region, such as a chloramphenicol acetyl transferase (CAT) transcription unit, downstream of restriction site or sites for introducing a candidate promoter fragment; i.e., a fragment that may contain a promoter. As is well known, introduction into the vector of a promoter-containing fragment at the restriction site upstream of the CAT gene engenders production of CAT activity, which can be detected by standard CAT assays. Vectors suitable to this end are well known and readily available, such as pKK232-8 and pCAT3. Promoters for expression of polynucleotides of the present invention include not only well known and readily available promoters, but also promoters that readily may be obtained by the foregoing technique, using a reporter gene. Among known prokaryotic promoters suitable for expression of polynucleotides and polypeptides in accordance with the present invention are the *E. coli* lacI and lacZ promoters, the T3 and T7 promoters, the gpt promoter, the lambda PR and PL promoters, and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Vectors for propagation and expression generally will include selectable markers and amplification regions, such as, for example, those set forth in Sambrook et al., supra.

Host Cells

As hereinbefore mentioned, the present invention also teaches host cells which are genetically engineered with vectors of the invention.

Polynucleotide constructs in host cells can be used in a conventional manner to produce the gene product encoded by the recombinant sequence. The subject polynucleotides or polypeptides products or isoforms or parts thereof, may be obtained by expression a suitable host cell using techniques known in the art. Suitable host cells include prokaryotic or eukaryotic organisms or cell lines, for example bacterial, mammalian, yeast, or other fungi, viral, plant or insect cells. Methods for transforming or transfecting cells to express foreign DNA are well known in the art (See for example, Itakura et al., U.S. Pat. No. 4,704,362; Murray et al. U.S. Pat. No. 4,801,542; McKnight et al., U.S. Pat. No. 4,935,349; Hagen et al., U.S. Pat. No. 4,784,950; Axel et al., U.S. Pat. No. 4,399,216; Goeddal et al., U.S. Pat. No. 4,766,075 and Sambrook et al., 1989, *Molecular Cloning, 2nd Edition*, Cold Spring Harbor Laboratory Press, Cold Spring Harbour, N.Y. all of which are incorporated herein by reference). Representative examples of appropriate hosts include bacterial cells, such as Streptococci, Staphylococci, *E. coli, Streptomyces* and *Bacillus subtilis*; fungal cells, such as yeast cells and *Aspergillus* cells; insect cells such as *Drosophila* S2 and *Spodoptera* Sf9 cells; animal cells such as CHO, COS-1, ZR-75-1, Chang, HeLa, C127, 3T3, HepG2, BHK, 293 and Bowes melanoma cells; and plant cells.

Host cells can be genetically engineered to incorporate polynucleotides and express polynucleotides of the present invention. Introduction of polynucleotides into the host cell can be effected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., 1986, *Basic Methods in Molecular Biology*, Elsevier, NY and Sambrook et al., 1989, *Molecular Cloning, 2nd Edition*, Cold Spring Harbor Laboratory Press, Cold Spring Harbour, N.Y.

Production of the Subject Polypeptides

As hereinbefore mentioned, the present invention also teaches the production of polynucleotides of the invention by recombinant techniques.

The subject polynucleotides encode polypeptides which are the mature protein plus additional amino- or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. Generally, as is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

Thus, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

The polypeptides of the invention may be prepared by culturing the host/vector systems described above, in order to express the recombinant polypeptides. Recombinantly produced subject protein or parts thereof, may be further purified using techniques known in the art such as commercially available protein concentration systems, by salting out the protein followed by dialysis, by affinity chromatography, or using anion or cation exchange resins.

Mature proteins can be expressed in mammalian cells, yeast, bacteria, or other cells under the control of appropriate promoters. Cell-free translation systems can also be employed to produce such proteins using DNA derived from the DNA constructs of the present invention. Appropriate cloning and expression vectors for use with prokaryotic and eukaryotic hosts are described by Sambrook et al., supra.

Polynucleotides of the invention, encoding the heterologous structural sequence of a polynucleotide or polypeptide of the invention generally will be inserted into a vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polynucleotide or polypeptide to be expressed. Generally, there will be no other open reading frames that begin with an initiation codon, usually AUG, and lie between the ribosome binding site and the initiation codon. Also, generally, there will be a translation stop codon at the end of the expressed polynucleotide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polynucleotide or polypeptide. These signals may be endogenous to the polynucleotide or they may be heterologous signals. Microbial cells employed in expression of proteins can be disrupted by any convenient method, including freeze-thaw cycling, sonication, mechanical disruption, or use of cell lysing agents, or other such methods know to those skilled in the art. A subject polynucleotide or polypeptide can be recovered and purified from recombinant cell cultures by known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polynucleotide is denatured during isolation and or purification.

A nucleic acid molecule of the invention may be cloned into a glutathione S-transferase (GST) gene fusion system for example the pGEX-1T, pGEX-2T and pGEX-3X of Pharmacia. The fused gene may contain a strong lac promoter, inducible to a high level of expression by IPTG, as a regulatory element. Thrombin or factor Xa cleavage sites may be present which allow proteolytic cleavage of the desired polypeptide from the fusion product. The glutathione S-transferase-subject polypeptide fusion protein may be easily purified using a glutathione sepharose 4B column, for example from Pharmacia. The 26 kDa glutathione S-transferase polypeptide can be cleaved by thrombin (pGEX-1T or pGEX-2T) or factor Xa (pGEX-3X) and resolved from the polypeptide using the same affinity column. Additional chromatographic steps can be included if necessary, for example Sephadex or DEAE cellulose. The two enzymes may be monitored by protein and enzymatic assays and purity may be confirmed using SDS-PAGE.

The subject protein or parts thereof may also be prepared by chemical synthesis using techniques well known in the chemistry of proteins such as solid phase synthesis (Merrifield, 1964, *J. Am. Chem. Assoc.,* 85: 2149-2154) or synthesis in homogenous solution (Houbenweyl et al., 1987, *Methods of Organic Chemistry*, Wansch E. (ed), Vol. 15 I and II, Thieme, Germany).

Within the context of the present invention, the subject polypeptide includes various structural forms of the primary protein which retain biological activity. For example, the subject polypeptide may be in the form of acidic or basic salts or in neutral form. In addition, individual amino acid residues may be modified by oxidation or reduction. Furthermore, various substitutions, deletions or additions may be made to the amino acid or nucleic acid sequences, the net effect being that biological activity of the subject polypeptide is retained. Due to code degeneracy, for example there maybe considerable variation in nucleotide sequences encoding the same amino acid.

The polypeptide may be expressed in a modified form, such as a fusion protein, and may include not only secretion signals but also additional heterologous functional regions. Thus, for instance, a region of additional amino acids, particularly charged amino acids, may be added to the carboxyl- or amino-terminus of the polypeptide to improve stability and persistence in the host cell during purification or during subsequent handling and storage. Also, fusion proteins may be added to the polynucleotide or polypeptide to facilitate purification. Such regions may be removed prior to final preparation of the polynucleotide or polypeptide. The addition of peptide moieties to polynucleotides or polypeptides to engender secretion or excretion, to improve stability or to facilitate purification, among others, are familiar and routine techniques in the art. In drug discovery, for example, proteins have been fused with antibody Fc portions for the purpose of high-throughput screening assays to identify antagonists (Bennett et al., 1995, *J. Mol. Recognit.,* 8: 52-58, and Johanson et al., 1995, *J. Biol. Chem.,* 270: 9459-9471).

Antibodies

With respect to protein-based testing, antibodies can be generated to the elongase gene product using standard immunological techniques, fusion proteins or synthetic peptides as described herein. Monoclonal antibodies can also be produced using now conventional techniques such as those described in Waldmann T. A., 1991, *Science,* 252: 1657-1662 and Harlow E. and Lane D. (eds.), 1988, *Antibodies: A Laboratory Manual*, Cold Harbour Press, Cold Harbour, N.Y. It will also be appreciated that antibody fragments, i.e. Fab' fragments, can be similarly employed. Immunoassays, for example ELISAs, in which the test sample is contacted with antibody and binding to the gene product detected, can provide a quick and efficient method of determining the presence and quantity of the elongase gene product. For example, the antibodies can be used to test the effect of pharmaceuticals in subjects enrolled in clinical trials.

Thus, the present invention also provides polyclonal and/or monoclonal antibodies and fragments thereof, and immunologic binding equivalents thereof, which are capable of specifically binding to the subject polypeptides and fragments thereof or to polynucleotide sequences from the subject polynucleotide region, particularly from the subject polypeptide locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the subject polypeptide or fragment. Monoclonal antibodies may be made by injecting mice with the protein polypeptides, fusion proteins or fragments thereof. Monoclonal antibodies are screened by ELISA and tested for specific immunoreactivity with subject polypeptide or fragments thereof (Harlow E. and Lane D. (eds.), 1988, *Antibodies: A Laboratory Manual*, Cold Harbour Press, Cold Harbour, N.Y.). These antibodies are useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical routes for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art, such as in Harlow E. and Lane D. (eds.), 1988, *Antibodies: A Laboratory Manual*, Cold Harbour Press, Cold Harbour, N.Y., or Goding J. W., 1996, *Monoclonal Antibodies: Principles and Practice: Production and Application of Monoclonal Antibodies in Cell Biology, Biochemistry and Immunology*, $3^{rd}$ edition, Academic Press, New York.

Monoclonal antibodies with affinities of $10^8$ $M^{-1}$ or preferably $10^9$ to $10^{10}$ $M^{-1}$ or stronger will typically be made by standard procedures as described in Harlow E. and Lane D. (eds.), 1988, *Antibodies: A Laboratory Manual*, Cold Harbour Press, Cold Harbour, N.Y. or Goding J. W., 1996, *Monoclonal Antibodies: Principles and Practice: Production and Application of Monoclonal Antibodies in Cell Biology, Biochemistry and Immunology*, $3^{rd}$ edition, Academic Press, New York. Briefly, appropriate animals will be selected and the desired immunization protocol followed. After the appropriate period of time, the spleens of such animals are excised and individual spleen cells fused, typically, to immortalized myeloma cells under, appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors (Huse et al., 1989, Science, 246: 1275-1281). The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

Generation of Polyclonal Antibody Against the Subject Polynucleotide

Sequences of the subject polynucleotide coding sequence are expressed as fusion protein in E. coli. The overexpressed protein is purified by gel elution and used to immunize rabbits and mice using a procedure similar to the one described by Harlow E. and Lane D. (eds.), 1988, Antibodies: A Laboratory Manual, Cold Harbour Press, Cold Harbour, N.Y. This procedure has been shown to generate antibodies against various other proteins (for example, see Kraemer et al., 1993, J. Lipid Res., 34: 663-671).

Briefly, a stretch of coding sequence selected from the subject polynucleotide is cloned as a fusion protein in plasmid pET5A (Novagen, WI) or pMAL system (New England Biolabs, U.S.). After induction with IPTG, the overexpression of a fusion protein with the expected molecular weight is verified by SDS-PAGE. Fusion protein is purified from the gel by electroelution. The identification of the protein as the subject polypeptide fusion product can be verified by protein sequencing at the N-terminus. Next, the purified protein is used as immunogen in rabbits. Rabbits are immunized with 100 μg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter.

This procedure is repeated to generate antibodies against the mutant forms of the subject polypeptide. These antibodies, in conjunction with antibodies to wild type subject polypeptide, are used to detect the presence and the relative level of the mutant forms in various tissues and biological fluids.

Generation of Monoclonal Antibodies Specific for the Subject Polypeptide

Monoclonal antibodies are generated according to the following protocol. Mice are immunized with immunogen comprising intact subject polypeptide or its peptides (wild type or mutant) conjugated to keyhole limpet hemocyanin using glutaraldehyde or EDC as is well known.

The immunogen s mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared as described by Harlow E. and Lane D. (eds.), 1988, Antibodies: A Laboratory Manual, Cold Harbour Press, Cold Harbour, N.Y. Cell fusions are performed essentially as described by Kohler G. and Milstein C., 1975, Nature, 256: 495-497. Briefly, P3.65.3 myeloma cells (American Type Culture Collection, Rockville, Md.) are fused with immune spleen cells using polyethylene glycol as described by Harlow E. and Lane D. (eds.), 1988, Antibodies: A Laboratory Manual, Cold Harbour Press, Cold Harbour, N.Y. Cells are plated at a density of $2 \times 10^5$ cells/well in 96 well tissue culture plates. Individual wells are examined for growth and the supernatants of wells with growth are tested for the presence of subject polypeptide specific antibodies by ELISA or RIA using wild type or mutant target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

Sandwich Assay for the Subject Polypeptide

Monoclonal antibody is attached to a solid surface such as a plate, tube, bead, or particle. Preferably, the antibody is attached to the well surface of a 96-well ELISA plate. A 100 μl sample (e.g., serum, urine, tissue cytosol) containing the subject polypeptide/protein (wild-type or mutant) is added to the solid phase antibody. The sample is incubated for 2 hrs at room temperature. Next the sample fluid is decanted, and the solid phase is washed with buffer to remove unbound material. One hundred μl of a second monoclonal antibody (to a different determinant on the subject polypeptide/protein) is added to the solid phase. This antibody is labeled with a detector molecule or atom (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of subject polypeptide/protein present in the sample, is quantitated. Separate assays are performed using monoclonal antibodies which are specific for the wild-type subject polypeptide as well as monoclonal antibodies specific for each of the mutations identified in subject polypeptide.

Detecting Presence of or Predisposition for Disorders Affected by Lipid Metabolism and Monitoring Treatment of Same As previously discussed, lipid metabolism is frequently disregulated in disease. It is likely that genetic polymorphisms in elongase genes will contribute to disease susceptibility.

The subject polynucleotides taught herein are useful to detect genetic polymorphisms of the subject polynucleotides, or to detecting changes in the level of expression of the subject polynucleotides, as a diagnostic tool. Detection of an aberrant form of the subject polynucleotide, or a decrease or increase in the level of expression of the subject polynucleotide in a eukaryote, particularly a mammal, and especially a human, will provide a method for diagnosis of a disease. Eukaryotes (herein also "individual(s)"), particularly mammals, and especially humans, exhibiting genetic polymorphisms of the subject polynucleotides, or changes in expression of the subject polynucleotides may be detected by a variety of techniques.

Since elongase genes are widely expressed, test samples of the subject can be obtained from a variety of tissues including blood. An elongase gene test can also be included in panels of prenatal tests since elongase genes, DNA, RNA or protein can also be assessed in amniotic fluid. Quantitative testing for elongase gene transcript and gene product is thus also contemplated within the scope of the present invention.

Nucleic acid and protein-based methods for screening genetic polymorphisms in elongase genes are all within the scope of the present teachings. For example, knowing the sequence of the elongase gene, DNA or RNA probes can be constructed and used to detect mutations in elongase genes through hybridization with genomic DNA in a tissue such as blood using conventional techniques. RNA or cDNA probes can be similarly probed to screen for mutations in elongase genes or for quantitative changes in expression. A mixture of different probes, i.e. "probe cocktail", can also be employed to test for more than one mutation.

With respect to nucleic acid-based testing, genomic DNA may be used directly for detection of a specific sequence or may be amplified enzymatically in vitro by using PCR prior to analysis. (Saiki et al., 1985, *Science*, 230: 1350-1353 and Saiki et al., 1986, *Nature*, 324: 163-166). Reviews of this subject have been presented by Caskey C. T., 1989, *Science*, 236: 1223-1229 and by Landegren et al., 1989, *Science*, 242: 229-237. The detection of specific DNA sequence may be achieved by methods such as hybridization using specific oligonucleotides (Wallace et al., 1986, *Cold Spring Harbour Symp. Quant. Biol.*, 51: 257-261), direct DNA sequencing (Church et al., 1988, *Proc. Natl. Acad. Sci.*, 81: 1991-1995, the use of restriction enzymes (Flavell et al., 1978, *Cell*, 15: 25-41; Geever et al., 1981, *Proc. Natl. Acad. Sci.*, 78: 5081-5085), discrimination on the basis of electrophoretic mobility in gels with denaturing reagent (Myers et al., 1986, *Cold Spring Harbour Sym. Quant. Biol.*, 51: 275-284), RNase protection (Myers et al., 1985, *Science*, 230: 1242-1246), chemical cleavage (Cotton et al., 1985, *Proc. Natl. Acad. Sci.*, 85: 4397-4401), and the ligase-mediated detection procedure (Landegren et al., 1988, *Science*, 241: 1077-1080). Using PCR, characterization of the level of or condition of the subject polynucleotides present in the individual may be made by comparative analysis.

With respect to protein-based testing, antibodies can be generated to the elongase gene product using standard immunological techniques, fusion proteins or synthetic peptides as described herein.

With the characterization of the elongase gene product and its function, functional assays can also be used for elongase gene diagnosis and screening and to monitor treatment. For example, enzymatic testing to determine levels of gene function, rather than direct screening of the elongase gene or product, can be employed. Testing of this nature has been utilized in other diseases and conditions, such as in Tay-Sachs.

The invention thus provides a process for detecting disease by using methods known in the art and methods described herein to detect changes in expression of or mutations to the subject polynucleotides. For example, decreased expression of a subject polynucleotide can be measured using any one of the methods well known in the art for the quantification of polynucleotides, such as, for example, PCR, RT-PCR, DNase protection, Northern blotting and other hybridization methods. Thus, the present invention provides a method for detecting disorders affected by lipid metabolism, and a method for detecting a genetic pre-disposition for such diseases including eczema, cardiovascular disorders (including but not limited to hypertriglyceridemia, dyslipidemia, atherosclerosis, coronary artery disease, cerebrovascular disease and peripheral vascular disease), inflammation (including but not limited to sinusitis, asthma, pancreatitis, osteoarthritis, rheumatoid arthritis and acne), body weight disorders (including but not limited to obesity, cachexia and anorexia), psychiatric disorders, cancer, cystic fibrosis, premenstrual syndrome, diabetes and diabetic complications.

Drug Screening Assays

The present teachings provide methods for screening compounds to identify those which enhance (agonist) or block (antagonist) the action of subject polypeptides or polynucleotides, such as its interaction with fatty acid binding molecules. The identification of the subject polynucleotides in inherited fatty acid disorders, combined with advances in the field of transgenic methods, provides the information necessary to further study human diseases. This is extraordinarily useful in modeling familial forms of fatty acid disorders and other diseases of fatty acid metabolism including eczema, cardiovascular disorders (including but not limited to hypertriglyceridemia, dyslipidemia, atherosclerosis, coronary artery disease, cerebrovascular disease and peripheral vascular disease), inflammation (including but not limited to sinusitis, asthma, pancreatitis, osteoarthritis, rheumatoid arthritis and acne), body weight disorders (including but not limited to obesity, cachexia and anorexia), psychiatric disorders, cancer, cystic fibrosis, pre-menstrual syndrome, diabetes and diabetic complications. Drug screening assays are made effective by use of the control regions of the genes described in the present invention or part of it, in a yeast based DNA-protein interaction assay (yeast one-hybrid). The use of the genes described here, or parts thereof, or the transcribed RNA in a yeast protein-protein interaction (2-hybrid) or protein-RNA interaction assays for drug screening also provide effective drug screening methods. Such interacting molecules can also be reconstructed in vitro for drug screening purposes.

For example, to screen for agonists or antagonists, a synthetic reaction mix, a cellular compartment such as a membrane, cell envelope or cell wall, or a preparation of any thereof, may be prepared from a cell that expresses a molecule that binds a subject polynucleotide. The preparation is incubated with labeled polynucleotide in the absence or the presence of a candidate molecule which may be an agonist or antagonist. The ability of the candidate molecule to bind the binding molecule is reflected in decreased binding of the labeled ligand.

Effects of potential agonists and antagonists may by measured, for instance, by determining activity of a reporter system following interaction of the candidate molecule with a cell or appropriate cell preparation, and comparing the effect to a baseline (control) measurement. Reporter systems that may be useful in this regard include, but are not limited to, calorimetric labeled substrate converted into product, a reporter gene that is responsive to changes in elongase enzyme activity, and binding assays known in the art.

Another example of an assay for antagonists is a competitive assay that combines a subject polypeptide and a potential antagonist with membrane-bound subject polypeptide-binding molecules, recombinant subject polypeptide binding molecules, natural substrates or ligands, or substrate or ligand mimetics, under appropriate conditions for a competitive inhibition assay. A subject polypeptide can be labeled, such as by radioactivity or a colorimetric compound, such that the number of subject polypeptide molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, peptides, polypeptides, such as closely related proteins or antibodies that bind the same sites on a binding molecule, without inducing subject polypeptide-induced activities, thereby preventing the action of the subject polypeptide by excluding the subject polypeptide from binding. Potential antagonists include antisense molecules (Okano et al., 1988, *EMBO J.*, 7: 3407-3412). Potential antagonists include compounds related to and derivatives of the subject polypeptides.

Potential antagonists include small organic molecules, peptides, polypeptides and antibodies that bind to a polynucleotide or polypeptide of the invention and thereby inhibit or extinguish its activity. Potential agonists may be selected from the group consisting of small organic molecules, peptides, polypeptides, antisense molecules, oligonucleotides, polynucleotides, fatty acids, and chemical and functional derivatives thereof.

Developing modulators of the biological activities of specific elongases requires differentiating elongase isozymes present in a particular assay preparation. The classical enzymological approach of isolating elongases from natural tissue sources and studying each new isozyme may be used. Another approach has been to identify assay conditions which might favor the contribution of one isozyme and minimize the contribution of others in a preparation. Still another approach is the separation of elongases by immunological means. Each of the foregoing approaches for differentiating elongase isozymes is time consuming. As a result many attempts to develop selective elongase modulators have been performed with preparations containing more than one isozyme. Moreover, elongase preparations from natural tissue sources are susceptible to limited proteolysis and may contain mixtures of active proteolytic products that have different kinetic, regulatory and physiological properties than the full length elongases.

Recombinant subject polypeptide products of the invention greatly facilitate the development of new and specific modulators. The need for purification of an isozyme can be avoided by expressing it recombinantly in a host cell that lacks endogenous elongase activity. Once a compound that modulates the activity of the elongase is discovered, its selectivity can be evaluated by comparing its activity on the particular subject enzyme to its activity on other elongase isozymes. Thus, the combination of the recombinant subject polypeptide products of the invention with other recombinant elongase products in a series of independent assays provides a system for developing selective modulators of particular elongases. Selective modulators may include, for example, antibodies and other proteins or peptides which specifically bind to the subject polypeptide or polynucleotide, oligonucleotides which specifically bind to the subject polypeptide (see Patent Cooperation Treaty International Publication No. WO 93/05182 which describes methods for selecting oligonucleotides which selectively bind to target biomolecules) or the subject polynucleotide (e.g., antisense oligonucleotides) and other non-peptide natural or synthetic compounds which specifically bind to the subject polynucleotide or polypeptide. Mutant forms of the subject polynucleotide which alter the enzymatic activity of the subject polypeptide or its localization in a cell are also contemplated. Crystallization of recombinant subject polypeptides alone and bound to a modulator, analysis of atomic structure by X-ray crystallography, and computer modeling of those structures are methods useful for designing and optimizing non-peptide selective modulators. See, for example, Erickson et al., 1992, *Ann. Rep. Med. Chem.*, 27: 271-289 for a general review of structure-based drug design.

Targets for the development of selective modulators include, for example: (1) the regions of the subject elongases which contact other proteins and/or localize the proteins within a cell, (2) the regions of the proteins which bind substrate, and (3) the phosphorylation site(s) of the subject polypeptides.

Thus, the present invention provides methods for screening and selecting compounds which promote disorders affected by lipids. As well, the present invention provides methods for screening and selecting compounds which treat or inhibit progression of diseases associated with lipid metabolism, such as eczema, cardiovascular disorders (including but not limited to hypertriglyceridemia, dyslipidemia, atherosclerosis, coronary artery disease, cerebrovascular disease and peripheral vascular disease), inflammation (including but not limited to sinusitis, asthma, pancreatitis, osteoarthritis, rheumatoid arthritis and acne), body weight disorders (including but not limited to obesity, cachexia and anorexia), psychiatric disorders, cancer, cystic fibrosis, premenstrual syndrome, diabetes and diabetic complications, and other diseases not necessary related to lipid metabolism.

Protein Interaction Assays for DNA Control Regions, CDS and RNA of Elongase Genes Protein interaction is implicated in virtually every biological process in the cell, for example, metabolism, transport, signaling and disease. Development of the yeast 2-hybrid and 1-hybrid systems have made it possible to study and identify protein-protein interaction, protein-DNA interaction or protein-RNA interaction in vivo (Fields S. and Song O., 1989, *Nature,* 340: 245-246; Ulmasov et al., 1997, *Science,* 276: 1865-1868; Furuyama K. and Sassa S., 2000, *J. Clin. Invest.,* 105: 757-764 and Gyuris et al., 1993, *Cell,* 75: 791-803). Because these interactions are key to cellular functions, identification of interacting partners is the first step towards elucidation of function and involvement in pathogenesis. New chemical entities that modulate (inhibit or activate) such interactions may have strong pharmaceutical and therapeutic benefit in human, animal as well as plant diseases. It is now known that in sideroblastic anemic patients, the interaction between succinyl-CoA synthetase and the heme biosynthetic enzyme δ-aminolevulinate synthase-E (ALAS-E) is disrupted (Furuyama K. and Sassa S., 2000, *J. Clin. Invest.,* 105: 757-764). Inhibition of gene expression in human cells through small molecule-RNA interaction have been recently described (Hwang et al., 1999, *Proc. Natl. Acad. Sci.,* 96: 12997-13002). The use of protein-RNA inhibition technology is a potential approach for development of anti-HIV therapeutics (Hamy et al., 1997, *Proc. Natl. Acad. Sci.,* 94: 3548-3553 and Mei et al., 1998, *Biochemistry,* 37: 14204-14212).

Drug Design

Antagonists and agonists and other compounds of the present invention may be employed alone or in conjunction with other compounds such as therapeutic compounds. The pharmaceutical compositions may be administered in any effective, convenient manner including, for instance, administration by direct microinjection into the affected area, or by intravenous or other routes. These compositions of the present invention may be employed in combination with a non-sterile or sterile carrier or carriers for use with cells, tissues or organisms, such as a pharmaceutical carrier suitable for administration to a subject. Such compositions comprise, for instance, a medium additive or a therapeutically effective amount of antagonists or agonists of the invention and a pharmaceutically acceptable carrier or excipient. Such carriers may include, but are not limited to, saline, buffered saline, dextrose, water, glycerol, ethanol and combinations thereof. The formulation is prepared to suit the mode of administration.

Modulation of elongase gene function can be accomplished by the use of therapeutic agents or drugs which can be designed to interact with different aspects of elongase structure or function. For example, a drug or antibody can bind to a structural fold of the protein to correct a defective structure. Alternatively, a drug might bind to a specific functional residue and increase its affinity for a substrate or cofactor. Efficacy of a drug or agent can be identified by a screening program in which modulation is monitored in vitro in cell systems in which a defective elongase is expressed.

Alternatively, drugs can be designed to modulate the activity of proteins of elongase genes from knowledge of the structure and function correlations for such proteins and from knowledge of the specific defect in various mutant proteins (Copsey et al., 1988, *Genetically Engineered Human Therapeutic Drugs*, Stockton Press, NY).

Gene Therapy

A variety of gene therapy approaches may be used in accordance with the invention to modulate expression of the subject polynucleotides in vivo. For example, antisense DNA molecules may be engineered and used to block translation of mRNA of the subject polynucleotides in vivo. Alternatively, ribozyme molecules may be designed to cleave and destroy the mRNA of the subject polynucleotides in vivo. In another alternative, oligonucleotides designed to hybridize to the 5' region of the subject polynucleotide (including the region upstream of the coding sequence) and form triple helix structures may be used to block or reduce transcription of the subject polynucleotide. In yet another alternative, nucleic acid encoding the full length wild-type subject polynucleotide may be introduced in vivo into cells which otherwise would be unable to produce the wild-type subject polynucleotide product in sufficient quantities or at all.

For example, in conventional replacement therapy, gene product or its functional equivalent is provided to the patient in therapeutically effective amounts. Elongases can be purified using conventional techniques such as those described in Deutcher M. (ed.), 1990, *Guide to Protein Purification*, *Meth. Enzymol.*, Vol. 182. Sufficient amounts of gene product or protein for treatment can be obtained, for example, through cultured cell systems or synthetic manufacture. Drug therapies which stimulate or replace the gene product can also be employed. Delivery vehicles and schemes can be specifically tailored to the particular target gene.

Gene therapy using recombinant technology to deliver the gene into the patient's cells, or vectors which will supply the patient with gene product in vivo, is also within the scope of the invention. Retroviruses have been considered preferred vectors for experiments in somatic gene therapy, with a high efficiency of infection and stable integration and expression (Orkin et al., 1988, *Prog. Med. Genet.*, 7: 130-142). For example, elongase cDNAs can be cloned into a retroviral vector and driven from either its endogenous promoter or from the retroviral LTR (long terminal repeat). Other delivery systems which can be utilized include adeno-associated virus (McLaughlin et al., 1988, *J. Virol.*, 62: 1963-1973), vaccinia virus (Moss et al., 1987, *Annu. Rev. Immunol.*, 5: 305-324), bovine papilloma virus (Rasmussen et al., 1987, *Meth. Enzymol.*, 139: 642-654), or a member of the herpes virus group such as Epstein-Barr virus (Margolskee et al., 1988, *Mol. Cell. Biol.*, 8: 2837-2847).

Antisense, ribozyme and triple helix nucleotides are designed to inhibit the translation or transcription of the subject polynucleotides. To accomplish this, the oligonucleotides used should be designed on the basis of relevant sequences unique to the subject polynucleotides. For example, and not by way of limitation, the oligonucleotides should not fall within those regions where the nucleotide sequence of a subject polynucleotide is most homologous to that of other polynucleotides, herein referred to as "unique regions".

In the case of antisense molecules, it is preferred that the sequence be chosen from the unique regions It is also preferred that the sequence be at least 18 nucleotides in length in order to achieve sufficiently strong annealing to the target mRNA sequence to prevent translation of the sequence (Izant J. G. and Weintraub H., 1984, *Cell*, 36: 100.7-1015 and Rosenberg et al., 1985, *Nature*, 313. :703-706).

In the case of the "hammerhead" type of ribozymes, it is also preferred that the target sequences of the ribozymes be chosen from the unique regions. Ribozymes are RNA molecules which possess highly specific endoribonuclease activity. Hammerhead ribozymes comprise a hybridizing region which is complementary in nucleotide sequence to at least part of the target RNA, and a catalytic region which is adapted to cleave the target RNA. The hybridizing region contains 9 or more nucleotides. Therefore, the hammerhead ribozymes of have a hybridizing region which is complementary to the sequences listed above and is at least nine nucleotides in length. The construction and production of such ribozymes are well known in the art and are described more fully in Haseloff J. and Gerlach W. L., 1988, *Nature*, 334: 585-591.

The ribozymes also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug et al., 1984, *Science*, 224: 574-578; Zaug A. J. and Cech T. R, 1986, *Science*, 231: 470-475; Zaug et al., 1986, *Nature*, 324: 429-433; Patent Publication Treaty International Patent Application No. WO 88/04300 and Been M. D. and Cech T. R., 1986, *Cell*, 47: 207-216). The Cech endoribonucleases have an eight base pair active site which hybridizes to a target RNA sequence whereafter cleavage of the target RNA takes place. Cech-type ribozymes target eight base-pair active site sequences are present in a subject polynucleotide but not other polynucleotides for elongases.

The compounds can be administered by a variety of methods which are known in the art, including, but not limited to the use of liposomes as a delivery vehicle. Naked DNA or RNA molecules may also be used where they are in a form which is resistant to degradation, such as by modification of the ends, by the formation of circular molecules, or by the use of alternate bonds including phosphothionate and thiophosphoryl modified bonds. In addition, the delivery of nucleic acid may be by facilitated transport where the nucleic acid molecules are conjugated to polylysine or transferrin. Nucleic acid may also be transported into cells by any of the various viral carriers, including but not limited to, retrovirus, vaccinia, adeno-associated virus, and adenovirus.

Alternatively, a recombinant nucleic acid molecule which encodes or is, such antisense, ribozyme, triple helix, or subject polynucleotide molecule can be constructed. This nucleic acid molecule may be either RNA or DNA. If the nucleic acid encodes an RNA, it is preferred that the sequence be operatively attached to a regulatory element so that sufficient copies of the desired RNA product are produced. The regulatory element may permit either constitutive or regulated transcription of the sequence. A transfer vector such as a bacterial plasmid or viral RNA or DNA, encoding one or more of the RNAs, may be transfected into cells or cells of an organism (Llewellyn et al., 1987, *J. Mol. Biol.,* 195: 115-123 and Hanahan et al., 1983, *J. Mol. Biol.,* 166: 557-580). Once inside the cell, the transfer vector may replicate, and be transcribed by cellular polymerases to produce the RNA or it may be integrated into the genome of the host cell. Alternatively, a transfer vector containing sequences encoding one or more of the RNAs may be transfected into cells or introduced into cells by way of micromanipulation techniques such as microinjection, such that the transfer vector or a part thereof becomes integrated into the genome of the host cell.

Composition, Formulation, and Administration of Pharmaceutical Compositions

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids gels, syrups, slurries, suspensions and the like for oral ingestion by a patient to be treated. Pharmaceutical preparations for oral use can be obtained by solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol, or cellulose preparations such as, maize starch, wheat starch, rice starch, potato starch, gelatin, gum tragacanth, methyl cellulose, hydroxypropylmethylcellulose, sodium carboxymethylcellulose, and/or polyvinylpyrrolidone. If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges (e.g. gelatin) for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally the compounds may be delivered using a sustained-release system, such as semipermeable matrices of solid hydrophobic polymers containing therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of therapeutic reagent, additional strategies for protein stabilization may be employed.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but, not limited to, hydrochloric, sulfuric, acetic, lactic, tartaric, malic, succinic, etc. Salts tend to be more soluble in aqueous or other protonic solvents than are the corresponding free base forms.

Suitable routes of administration may, for example, include oral, rectal, transmucosal, transdermal, or intestinal administration; or parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

The pharmaceutical compositions generally are administered in an amount effective for treatment or prophylaxis of a specific indication or indications. It is appreciated that optimum dosage will be determined by standard methods for each treatment modality and indication, taking into account the indication, its severity, route of administration, complicating conditions and the like. In therapy or as a prophylactic, the active agent may be administered to an individual as an injectable composition, for example, as a sterile aqueous dispersion, preferably isotonic. A therapeutically effective dose further refers to that amount of the compound sufficient to result in amelioration of symptoms associated with such disorders. Techniques for formulation and administration of the compounds of the instant application may be found in "Remington's Pharmaceutical Sciences," Mack Publishing Co., Easton, Pa., latest edition. For administration to mammals, and particularly humans, it is expected that the daily dosage level of the active agent will be from 0.001 mg/kg to 10 mg/kg, typically around 0.01 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The compounds of the invention may be particularly useful in animal disorders (veterinarian indications), and particularly mammals.

The invention further provides diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Definitions

To facilitate a complete understanding of the invention, the terms defined below have the following meaning:

Agonist refers to any molecule or pharmaceutical agent, such as a drug or hormone, which enhances the activity of another molecule.

Antagonist refers to any molecule or pharmaceutical agent, such as a drug or hormone, which inhibits or extinguishes the activity of another molecule.

Chemical Derivative. As used herein, a molecule is said to be a "chemical derivative" of another molecule when it contains additional chemical moieties not normally a part of the molecule. Such moieties can improve the molecule's solubility, absorption, biological half life and the like. The moieties can alternatively decrease the toxicity of the molecule, eliminate or attenuate any undesirable side effect of the molecule, and the like. Moieties capable of mediating such effects are disclosed in Mack E. W., 1990, *Remington's Pharmaceutical Sciences*, Mack Publishing Company, Easton, Pa., 13$^{th}$ edition. Procedures for coupling such moieties to a molecule are well known in the art.

Compositions include genes, proteins, polynucleotides, peptides, compounds, drugs, and pharmacological agents.

Control region refers to a nucleic acid sequence capable of, or required for assisting or impeding initiation, termination, or otherwise regulating the transcription of a gene. The control region may include a promoter, enhancer, silencer and/or any other regulatory element. A control region also includes a nucleic acid sequence that may or may not be independently or exclusively sufficient to initiate, terminate, or otherwise regulate transcription, however, is capable of effecting such regulation in association with other nucleic acid sequences.

Desaturase refers to a fatty acid desaturase, which is an enzyme capable of generating a double bond in the hydrocarbon region of a fatty acid molecule.

Disorder as used herein refers to derangement or abnormality of structure or function. Disorder includes disease.

Drug. Drugs include, but are not limited to, proteins, peptides, degenerate peptides, agents purified from conditioned cell medium, organic molecules, inorganic molecules, antibodies or oligonucleotides. The drug can be naturally occurring or synthetically or recombinantly produced.

Enhancer is a nucleic acid sequence comprising a DNA regulatory element that enhances or increases transcription when bound by a specific transcription factor or factors. Moreover, an enhancer may function in either orientation and in any location (upstream or downstream relative to the promoter) to effect and generate increased levels of gene expression when bound by specific factors. In addition, according to the present invention, an enhancer also refers to a compound (i.e. test compound) that increases or promotes the enzymatic activity of the elongase gene, and/or increases or promotes the transcription of the gene.

Fatty Acids are a class of compounds comprising a long saturated or mono or polyunsaturated hydrocarbon chain and a terminal carboxyl group.

Fatty Acid Delta-5-Desaturase (D5D) is an enzyme capable of generating a double bond between carbons 5 and 6 from the carboxyl group in a fatty acid molecule.

Fatty Acid Delta-6-Desaturase is an enzyme capable of generating a double bond between carbons 6 and 7 from the carboxyl group in a fatty acid molecule.

Fatty Acid Elongase is an enzyme required for the addition of an acetyl or a 2-carbon chain to the carboxyl end of a fatty acid.

Functional Enzyme, as used herein, refers to a biologically active or non-active protein with a known enzymatic activity.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein can contain post-translational modifications such as covalently linked carbohydrate, depending on the necessity of such modifications for the performance of a specific function. The term "functional derivative" is intended to include the "fragments," "sequences," "variants," "analogs," or "chemical derivatives" of a molecule.

Gene refers to a nucleic acid molecule or a portion thereof, the sequence of which includes information required for the production of a particular protein or polypeptide chain. The polypeptide can be encoded by a full-length sequence or any portion of the coding sequence, so long as the functional activity of the protein is retained. A gene may comprise regions preceding and following the coding region as well as intervening sequences (introns) between individual coding sequences (exons). A "heterologous" region of a nucleic acid construct (i.e. a heterologous gene) is an identifiable segment of DNA within a larger nucleic acid construct that is not found in association with the other genetic components of the construct in nature. Thus, when the heterologous gene encodes a mammalian elongase gene, the gene will usually be flanked by a promoter that does not flank the structural genomic DNA in the genome of the source organism.

Host system may comprise a cell, tissue, organ, organism or any part thereof, which provides an environment or conditions that allow for, or enable, transcription and/or translation.

Identity, similarity, homology or homologous, refer to relationships between two or more polynucleotide sequences, as determined by comparing the sequences. In the art, identity also means the degree of sequence relatedness between polynucleotide sequences, as the case may be, as determined by the match between strings of such sequences. Both identity and similarity can be readily calculated (Lesk A. M., ed., 1988, *Computational Molecular Biology*, Oxford University Press, NY; Smith D. W., ed., 1993, *Biocomputing: Informatics and Genome Project*, Academic Press, NY; Griffin A. M. and Griffin H. G., eds., 1994, *Computer Analysis of Sequence Data, Part 1*, Humana Press, NJ; von Heijne G., 1987, *Sequence Analysis in Molecular Biology*, Academic Press, NY and Gribskov M. and Devereux J., eds., 1991, *Sequence Analysis Primer*, M Stockton Press, NY). While there exist a number of methods to measure identity and similarity between two polynucleotide sequences, both terms are well known to skilled artisans (von Heijne G., 1987, *Sequence Analysis in Molecular Biology*, Academic Press, NY; Gribskov M. and Devereux J., eds., 1991, *Sequence Analysis Primer*, M Stockton Press, NY and Carillo H. and Lipman D., 1988, *SIAM J. Applied Math.*, 48: 1073). Methods commonly employed to determine identity or similarity between sequences include, but are not limited to those disclosed in Carillo H. and Lipman D., 1988, *SIAM J. Applied Math.*, 48: 1073. Methods to determine identity and similarity are codified in computer programs. Computer program methods to determine identity and similarity between two sequences include, but are not limited to, GCG program package (Devereux et al., 1984, *Nucl. Acid Res.*, 12: 387-395), BLASTP, BLASTN and FASTA (Altschul et al., 1990, *J. Molec. Biol.*, 215: 403-410).

Isolated means altered "by the hand of man" from its natural state; i.e., that, if it occurs in nature, it has been changed or removed from its original environment, or both. For example, a naturally occurring polynucleotide naturally present in a living organism in its natural state is not "isolated," but the same polynucleotide separated from coexisting materials of its natural state is "isolated", as the term is employed herein. As part of or following isolation, such polynucleotides can be joined to other polynucleotides, such as DNA, for mutagenesis, to form fusion proteins, and for propagation or expression in a host, for instance. The isolated polynucleotides, alone or joined to other polynucleotides such as vectors, can be introduced into host cells in culture or in whole organisms. Introduced into host cells in culture or in whole organisms, such DNA still would be isolated, as the term is used herein, because they would not be in their naturally occurring form or environment. Similarly, the polynucleotides may occur in a composition, such as a media formulations, solutions for introduction of polynucleotides for example, into cells, compositions or solutions for chemical or enzymatic reactions, for instance, which are not naturally occurring compositions, and, therein remain isolated polynucleotides within the meaning of that term as it is employed herein.

Mutation. A "mutation" is any detectable change in the genetic material. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens or by site-directed mutagenesis. A mutant polypeptide can result from a mutant nucleic acid molecule.

Nucleic acid construct refers to any genetic element, including, but not limited to, plasmids and vectors, that incorporate polynucleotide sequences. For example, a nucleic acid construct may be a vector comprising a promoter or control region that is operably linked to a heterologous gene.

Operably linked as used herein indicates the association of a promoter or control region of a nucleic acid construct with a heterologous gene such that the presence or modulation of the promoter or control region influences the transcription of the heterologous gene, including genes for reporter sequences. Operably linked sequences may also include two segments that are transcribed onto the same RNA transcript. Thus, two sequences, such as a promoter and a "reporter sequence" are operably linked if transcription commencing in the promoter produces an RNA transcript of the reporter sequence.

Plasmids. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention.

Polynucleotides(s) the present invention may be in the form of RNA, such as mRNA, or in the form of DNA, including, for instance, cDNA and genomic DNA obtained by cloning or produced by chemical synthetic techniques or by a combination thereof The DNA may be double-stranded or single-stranded. Single-stranded polynucleotides may be the coding strand, also known as the sense strand, or it may be the non-coding strand, also referred to as the anti-sense strand. Polynucleotides generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide also includes DNA or DNA that contain one or more modified bases. Thus, DNA or DNA with backbones modified for stability or for other reasons are "polynucleotides" as that term is intended herein. Moreover, DNA or DNA comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s). It will also be appreciated that RNA made by transcription of this doubled stranded nucleotide sequence, and an antisense strand of a nucleic acid molecule of the invention or an oligonucleotide fragment of the nucleic acid molecule, are contemplated within the scope of the invention. An antisense sequence is constructed by inverting the sequence of a nucleic acid molecule of the invention, relative to its normal presentation for transcription. Preferably, an antisense sequence is constructed by inverting a region preceding the initiation codon or an unconserved region. The antisense sequences may be constructed using chemical synthesis and enzymatic ligation reactions using procedures known in the art.

Promoter refers to a nucleic acid sequence comprising a DNA regulatory element capable of binding RNA polymerase directly or indirectly to initiate transcription of a downstream (3' direction) gene. In accordance with the present invention, a promoter of a nucleic acid construct that includes a nucleotide sequence, wherein the nucleotide sequence may be linked to a heterologous gene such that the induction of the promoter influences the transcription of the heterologous gene.

Purified: A "purified" protein or nucleic acid is a protein or nucleic acid preparation that is generally free of contaminants, whether produced recombinantly, chemically synthesized or purified from a natural source.

Recombinant refers to recombined or new combinations of nucleic acid sequences, genes, or fragments thereof which are produced by recombinant DNA techniques and are distinct from a naturally occurring nucleic acid sequence Regulatory element refers to a deoxyribonucleotide sequence comprising the whole, or a portion of a nucleic acid sequence to which an activated transcriptional regulatory protein, or a complex comprising one or more activated transcriptional regulatory proteins, binds so as to transcriptionally modulate the expression of an associated gene or genes, including heterologous genes.

Reporter gene is a nucleic acid coding sequence whose product is a polypeptide or protein that, is not otherwise produced by the host cell or host system, or which is produced in minimal or negligible amounts in the host cell or host system, and which is detectable by various known methods such that the reporter gene product may be quantitatively assayed to analyse the level of transcriptional activity in a host cell or host system. Examples include genes for luciferase, chloramphenicol acetyl transferase (CAT), beta-galactosidase, secreted placental alkaline phosphatase and other secreted enzymes.

Silencer refers to a nucleic acid sequence or segment of a DNA control region such that the presence of the silencer sequence in the region of a target gene suppresses the transcription of the target gene at the promoter through its actions as a discrete DNA segment or through the actions of trans-acting factors that bind to these genetic elements and consequently effect a negative control on the expression of a target gene.

Stringent hybridization conditions are those which are stringent enough to provide specificity, reduce the number of mismatches and yet are sufficiently flexible to allow formation of stable hybrids at an acceptable rate. Such conditions are known to those skilled in the art and are described, for example, in Sambrook et al., 1989, *Molecular Cloning, 2nd Edition*, Cold Spring Harbor Laboratory Press, Cold Spring Harbour, N.Y. or Ausubel et al., 1994, *Current Protocols in Molecular Biology*, John Wiley & Sons, NY. By way of example only, stringent hybridization with short nucleotides may be carried out at 5-10° C. below the $T_M$ using high concentrations of probe such as 0.01-1.0 pmole/ml. Preferably, the term "stringent conditions" means hybridization will occur only if there is at least 95% and preferably at least 97% identity between the sequences.

Tag refers to a specific short amino acid sequence, or the oligonucleotide sequence that encodes it, wherein said amino acid or nucleic acid sequence may comprise or encode, for example, a c-myc epitope and/or a string of six histidine residues recognizable by commercially available antibodies. In practice, a tag facilitates the subsequent identification and purification of a tagged protein.

Tagged; protein as used herein refers to a protein comprising a linked tag sequence. For example, a tagged protein includes a mammalian elongase polypeptide linked to a c-myc epitope and six histidine residues at the carboxyl terminus of the amino acid sequence.

Test compounds as used herein encompass small molecules (e.g. small organic molecules), pharmacological compounds or agents, peptides, proteins, antibodies or antibody fragments, and nucleic acid sequences, including DNA and RNA sequences.

Transfection refers to a process whereby exogenous or heterologous DNA (i.e. a nucleic acid construct) is introduced into a recipient eukaryotic host cell. Therefore, in eukaryotic cells, the acquisition of exogenous DNA into a host cell is referred to as transfection. In prokaryotes and eukaryotes (for example, yeast and mammalian cells) introduced DNA may be maintained on an episomal element such as a plasmid or integrated into the host genome. With respect to eukaryotic cells, a stably transfected cell is one in which the introduced DNA has become integrated into a chromosome so that it is inherited by daughter cells through chromosome replication. This stability is demonstrated by the ability of the eukaryotic cell to establish cell lines or clones comprised of a population of daughter cells containing the introduced DNA.

Transformation refers to a process whereby exogenous or heterologous DNA (i.e. a nucleic acid construct) is introduced into a recipient prokaryotic host cell. Therefore, in prokaryotic cells, the acquisition of exogenous DNA into a host cell is referred to as transformation. Transformation in eukaryotes refers to the conversion or transformation of eukaryotic cells to a state of unrestrained growth in culture, resembling a tumongenic condition. In prokaryotes and eukaryotes(for example, yeast and mammalian cells) introduced DNA may be maintained on an episomal element such as a plasmid or integrated into the host genome. With prokaryotic cells, a stably transformed bacterial cell is one in which the introduced DNA has become integrated into a chromosome so that it is inherited by daughter cells through chromosome replication. This stability, is demonstrated by the ability of the prokaryotic cell to establish cell lines or clones comprised of a population of daughter cells containing the introduced DNA.

Transfection/transformation as used herein refers to a process whereby exogenous or heterologous DNA (e.g. a nucleic acid construct) has been introduced into a eukaryotic or prokaryotic host cell or into a host system.

Variant(s) of polynucleotides are polynucleotides that differ in nucleotide sequence from another, reference polynucleotide. A "variant" of a protein or nucleic acid is meant to refer to a molecule substantially similar in structure and biological activity to either the protein or nucleic acid. Thus, provided that two molecules possess a common activity and can substitute for each other, they are considered variants as that term is used herein even if the composition or secondary, tertiary, or quaternary structure of one of the molecules is not identical to that found in the other, or if the amino acid or nucleotide sequence is not identical. Generally, differences are limited so that the nucleotide sequences of the reference and the variant are closely similar overall and, in many regions, identical. Changes in the nucleotide sequence of the variant may be silent. That is, they may not alter the amino acids encoded by the polynucleotide. Where alterations are limited to silent changes of this type a variant will encode a polypeptide or polynucleotide with the same amino acid sequence as the reference. Changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide or polynucleotide encoded by the reference sequence.

Vector. A plasmid or phage DNA or other DNA sequence into which DNA can be inserted to be cloned. The vector can replicate autonomously in a host cell, and can be further characterized by one or a small number of endonuclease recognition sites at which such DNA sequences can be cut in a determinable fashion and into which DNA can be inserted. The vector can further contain a marker suitable for use in the identification of cells transformed with the vector. Markers, for example, are tetracycline resistance or ampicillin resistance. The words "cloning vehicle" are sometimes used for "vector."

The terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

The present invention is further described and will be better understood by referring to the working examples set forth below. These non-limiting examples are to be considered illustrative only of the principles of the invention. Since numerous modifications and changes will readily occur to those skilled in the art, it is not desired to limit the invention to the exact construction and operation shown and described. Accordingly, all suitable modifications and equivalents may be used and will fall within the scope of the invention and the appended claims.

EXAMPLES

The present invention is further described by the following examples. These examples, while illustrating certain specific aspects of the invention do not portray the limitations or circumscribe the scope of the disclosed invention.

Example 1

Cloning ELG1

ELG1 was cloned into the pYES2/CT yeast expression vector (Invitrogen) using PCR. Two plasmid constructions were made for the production of the ELG1 protein with either a C-terminal tag containing the V-5 epitope and polyhistidine peptide (ELG1/V5-His), or the ELG1 protein without the tag (ELG1). The forward primer (5'-CACGCG GGTACCAGGATGGAGGCTGTTGTGAAC-3') (SEQ. ID. NO. 14) contains the translation start codon and a KpnI site (underlined). The reverse primers for cloning ELG1 and ELG1/V5-His, 5'-ATATCACGAT GCGGCCGCTCAGTTGGCCTTGACCTTGGC-3' (SEQ.

ID. NO. 15) and 5'-ATATCACGAT GCGGCCGCCAGTTGGCCTTGACCTTGGC-3'(SEQ. ID. NO. 16), respectively, contain a NotI site (underlined). The reverse primer for cloning ELG1 provides the translation stop codon. The reverse primer for cloning ELG1/V5-His only contains 2 of the 3 bases of the stop codon, therefore, placing the gene in frame with the tag provided by the vector.

PCR was carried out using Advantage-HF polymerase (Clontech) as per the manufacturer's instructions. The SuperScript human leukocyte cDNA library (Gibco BRL) was used as the DNA template for cloning ELG1. pTh1009.1 (defined below) was used as the template for cloning ELG1/V5-His.

Figure 18:
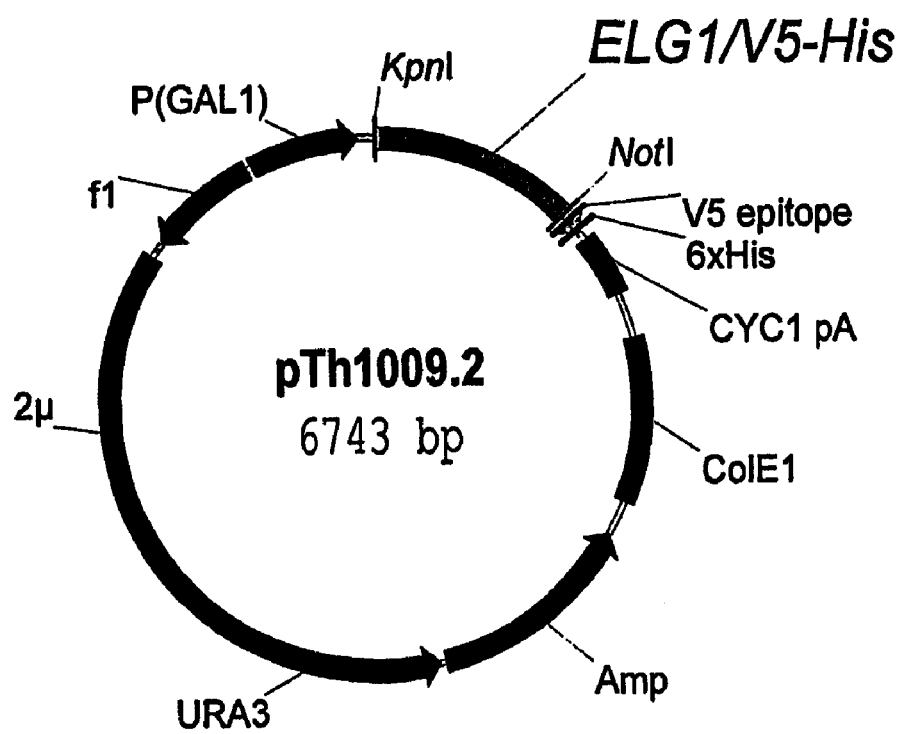
FIG. 18 is a schematic representation of plasmid pTh1009.2 (6743 bp). The human elongase (ELG1) coding sequence is shown between restriction sites for KpnI and NotI.

The PCR products were gel purified, digested with KpnI and NotI, and ligated into pYES2/CT cut with the same enzymes. The ligation products were used to transform *E. coli* strain INVαF' (Invitrogen). Plasmids were isolated and their inserts were sequenced. Plasmids coding for ELG1 and ELG1/V5-His were designated pTh1009.1 (FIG. 7) and pTh1009.2 (FIG. 18), respectively.

Example 2

Cloning ELG2

Obtaining Complete Coding Sequence for ELG2

Clones containing the complete coding sequence for ELG2 were obtained from the SuperScript human leukocyte cDNA library (Gibco BRL) using the GeneTrapper cDNA Positive Selection System (Gibco BRL) as per the manufacturer's instructions. The sequence of the oligonucleotide used to probe the library and repair the captured cDNA target was 5'-GTAACAGGAGTATGGGAAGGCA-3' (SEQ. ID. NO. 17). The repaired DNA was used to transform UltraMax DH5α-FT cells (Gibco BRL). Clones containing ELG2 were identified by colony PCR using 5'-TTGGACTCACACTGCTGTCTCT-3' (SEQ. ID. NO. 18) and 5'-GTGTGGCACCAAAATAAGAGTG-3' (SEQ. ID. NO. 19) as gene specific primers and Platinum Taq DNA polymerase (Gibco BRL). Plasmid DNA was isolated from selected colonies and their inserts were sequenced. The nucleotide sequence obtained was used to identify the open reading frame for ELG2 and to design primers for cloning ELG2 into a yeast expression vector. A plasmid containing the complete ELG2 coding sequence was designated pSh1010.1.

Cloning ELG2 into Expression Vector

ELG2 was cloned into the pYES2/CT yeast expression vector (Invitrogen) using PCR. Two plasmid constructions were made for the production of the ELG2 protein with either a C-terminal tag containing the V-5 epitope and polyhistidine peptide (ELG2/V5-His), or the ELG2 protein without the tag (ELG2). The forward primer (5'-CACGCG GGATCCCAAATGGAACATTTTGATGCATCAC-3') (SEQ. ID. NO. 20) contains the translation start codon and a BamHI site (underlined). The reverse primers for cloning ELG2 and ELG2/V5-His, 5'-ATATCACGAT GCGGCCGCTCAATCCTTCCGCAGCTTCC-3' (SEQ. ID. NO. 21) and 5'-ATATCACGAT GCGGCCGCCAATCCTTCCGCAGCTTCC-3'(SEQ. ID. NO. 22), respectively, contain a NotI site (underlined). The reverse primer for cloning ELG2 provides the translation stop codon. The reverse primer for cloning ELG2/V5-His only contains 2 of the 3 bases of the stop codon, therefore, placing the gene in frame with the tag provided by the vector.

PCR was carried out using Advantage-HF polymerase (Clontech) as per the manufacturer's instructions. pSh1010.1 was used as the DNA template for cloning ELG2. pMr1014.1 (described below) was used as the DNA template for ELG2/V5-His.

The PCR products were gel purified, digested with BamHI and NotI, and ligated into pYES2/CT cut with the same enzymes. The ligation products were used to transform *E. coli* strain TOP10F' (Invitrogen). Plasmids were isolated and their inserts were sequenced. Plasmids coding for ELG2 and ELG2/V5-His were designated pTh1014.1 and pTh1014.2, respectively.

Example 3

Cloning ELG3

ELG3 was cloned into the pYES2/CT yeast expression vector (Invitrogen) using PCR. Two plasmid constructions were made for the production of the ELG3 protein with either a C-terminal tag containing the V-5 epitope and polyhistidine peptide (ELG3/V5-His), or the ELG3 protein without the tag (ELG3). The forward primer (5'-CACGCG GGATCCACATGAACACTAAAGGCC-3') (SEQ. ID. NO. 23) contains the translation start codon and a BamHI site (underlined). The reverse primers for cloning ELG3 and ELG3/V5-His, 5'-ATATCACGAT GCGGCCGCTTATTGTGCTTCTTGTTCATCACTCC-3' (SEQ. ID. NO. 24) and 5'-ATATCACGAT GCGGCCGCTTTTGTGCTTCTTGTTCATCACTCC-3', (SEQ. ID. NO. 25), respectively, contain a NotI site (underlined). The reverse primer for cloning ELG3 provides the translation stop codon. The reverse primer for cloning ELG3/V5-His only contains 2 of the 3 bases of the stop codon, therefore, placing the gene in frame with the tag provided by the vector.

PCR was carried out using Advantage-HF polymerase (Clontech) as per the manufacturer's instructions. cDNA prepared from ZR-75-1 cells (ATCC No. CRL-1500) was used as the DNA template. This cDNA was prepared by isolating RNA from the ZR-75-1 cells using Trizol reagent (Gibco BRL) as per the manufacturer's instructions and then reverse transcribing the RNA using MuLV reverse transcriptase and random hexamers as described for the GeneAmp RNA PCR kit (PE Applied Biosystems).

PCR products were gel purified, digested with BamHI and NotI, and ligated into pYES2/CT cut with the same enzymes. The ligation products were used to transform *E. coli* strain TOP10F' (Invitrogen). Plasmids were isolated and their inserts were sequenced. Plasmids coding for ELG3 and ELG3/V5-His were designated pTh1015.1 and pTh1017.1, respectively.

Figure 19:
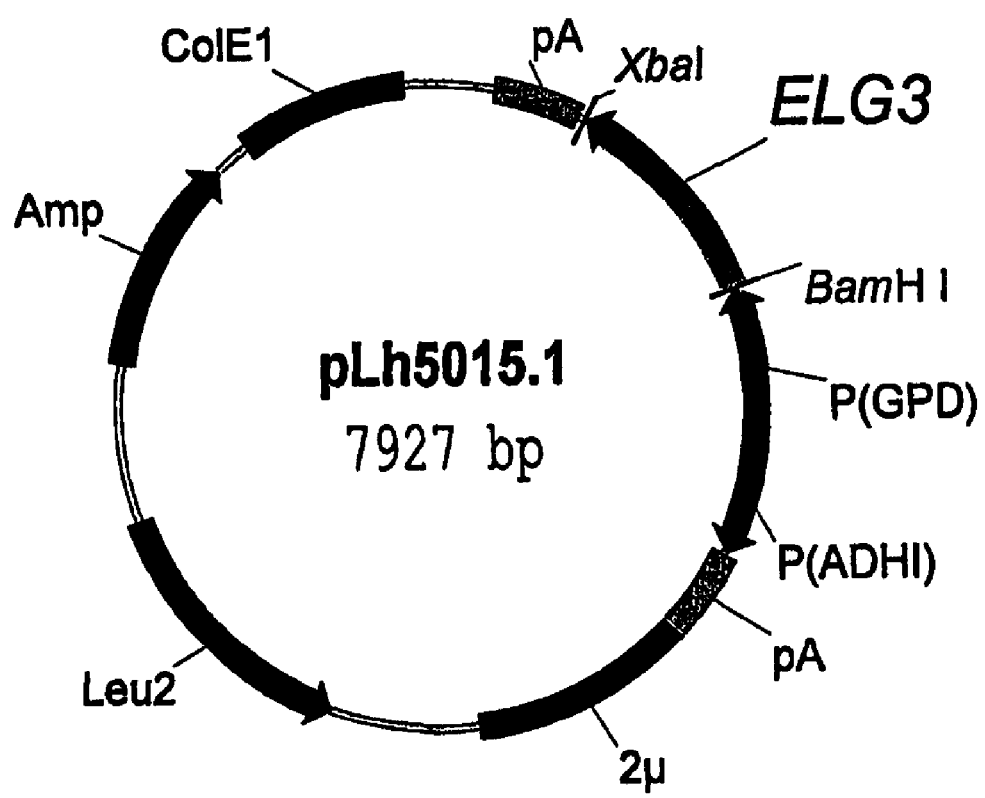
FIG. 19 is a schematic representation of plasmid pLh5015.1 (7927 bp). The human elongase (ELG3) coding sequence is shown between restriction sites for BamHI and XbaI.

ELG3 was also cloned into the pBEVY-L yeast expression vector (Miller et al., 1998, *Nuc. Acids Res.*, 26: 3577-3583) under the control of the constitutive glyceraldehyde 3-phosphate dehydrogenase promoter. The ELG3 coding sequence was obtained by restricting pTh1015.1 with BamHI and XbaI, and gel purifying the ~0.9 kb fragment. The pBEVY vector was restricted with BamHI and EcoRI, or XbaI and EcoRI, and the ~1 kb and ~6 kb fragments, respectively, were gel purified. The three fragments were ligated and the ligation products were used to transform *E. coli* strain INVαF' (Invitrogen). A plasmid containing the ELG3 gene was isolated and identified by restriction analysis. The insert DNA was confirmed by DNA sequencing and the plasmid designated pLh5015.1 (FIG. 19).

Example 4

Cloning ELG4

Obtaining Complete Coding Sequence for ELG4

A cDNA clone with an incomplete coding sequence for ELG4 was obtained from the SuperScript human leukocyte cDNA library (Gibco BRL) using the GeneTrapper cDNA Positive Selection System (Gibco BRL) as per the manufacturer's instructions. The sequence of the oligonucleotide used to probe the library and repair the captured cDNA target was 5'-GCCAGCCTACCAGAAGTATTTG-3'(SEQ. ID. NO. 26). The repaired DNA was used to transform UltraMax DH5α-FT cells (Gibco BRL). A clone containing ELG4 was identified by colony PCR using 5'-GCGCAA-GAAAAATAGCCAAG-3' (SEQ. ID. NO. 27) and 5'-AAT-GATGCACGCAAAGACTG-3' (SEQ. ID. NO. 28) as gene specific primers and Platinum Taq DNA polymerase (Gibco BRL). Plasmid DNA was isolated and the insert was sequenced. The plasmid was designated pSh1026.1. The complete coding sequence for ELG4 could not be determined, however, an open reading frame containing the C-terminus of the ELG4 protein was identified. Subsequent cloning (described below) revealed that pSh1026.1 contains an ELG4 variant with an internal deletion of nucleotides 210-255 of the coding sequence.

The nucleotide sequence obtained from pSh1026.1 was used to design a forward (5'-CACGCG GGATCCCTGATGAATACAGAGCCGTGG-3') (SEQ. ID. NO. 29)and reverse (5'-ATATCACGAT GCGGCCGCTCAATTATTGTTTGCAAGTTCC-3') (SEQ. ID. NO. 30) primer for cloning ELG4 by PCR. These primers contain a BamHI and NotI site, respectively (underlined). The forward primer includes the first possible translation start codon identified in pSh1026.1. The reverse primer provides the translation stop codon.

PCR was carried out using Advantage HF polymerase (Clontech) as per the manufacturer's instructions. The Superscript human leukocyte cDNA library (Gibco BRL) was used as the DNA template.

The PCR products were gel purified, digested with BamHI and NotI, and ligated into PYES2/CT (Invitrogen), cut with the same enzymes. The ligation products were used to transform E. coli strain TOP10 (Invitrogen). Plasmids were isolated and their inserts were sequenced. A plasmid containing the complete coding sequence for ELG4 as well as 108 nucleotides of 5'-UTR was designated pTh1030.1.

Cloning ELG4 into Expression Vector

ELG4 was cloned into the pYES2/CT yeast expression vector using PCR. Two plasmid constructions were made for the production of the ELG4 protein with either a C-terminal tag containing the V-5 epitope and polyhistidine peptide (ELG4/V5-His), or the ELG4 protein without the tag (ELG4). The forward primer (5'-CACGCG GGATCCCTGATGGAAAAAGCCCATTAATATTC-3') (SEQ. ID. NO. 31) contains the translation start codon and a BamHI site (underlined). The reverse primers for cloning ELG4 and ELG4/V5-His, 5'-ATATCACGAT GCGGCCGCTCAATTATCTTTGTTTTTGCAAGTTCC-3' (SEQ. ID. NO. 32) and 5'-ATATCACGAT GCGCGCCAATTTTTGTGCAAGTTCC-3' (SEQ. ID. NO. 33), respectively, contain a NotI site (underlined). The reverse primer for cloning ELG4 provides the translation stop codon. The reverse primer for cloning ELG4/V5-His only contains 2 of the 3 bases of the stop codon, therefore, placing the gene in frame with the tag provided by the vector.

PCR was carried out using Advantage-HF polymerase (Clontech) as per the manufacturer's instructions. pTh1030.1 was used as the DNA template for ELG4 and pTh1021.1 (described below) was used as the template for ELG4/V5-His.

The PCR products were gel purified, digested with BamHI and NotI, and ligated into pYES2/CT cut with the same enzymes. The ligation products were used to transform E. coli strain TOP10 (Invitrogen). Plasmids were isolated and their inserts were sequenced. Plasmids coding for ELG4 and ELG4/V5-His were designated pTh1021.1 and pTh1021.2, respectively.

Example 5

Cloning ELG5

ELG5 was cloned into the pYES2/CT yeast expression vector (Invitrogen) using PCR. Two plasmid construction were made for the production of the ELG5 protein with either a C-terminal tag containing the V-5 epitope and polyhistidine peptide (ELG5/V5-His), or the ELG5 protein without the tag (ELG5). The forward primer (5'-CACGCG GGATCCAAAATGAACATGTCAGTGTTGACTTTACA AG-3') (SEQ. ID. NO. 34) contains the translation start codon and a BamHI site (underlined). The reverse primers for cloning ELG5 and ELG5/V5-His, 5'-ATATCACGAT GCGGCCGCCTATTCAGCTTTCGTTGTTTTCCTC-3' (SEQ. ID. NO. 35) and 5'-ATATCACGAT GCGGCCGCCATTCAGCTTCGTTGTTTTCCTC-3' (SEQ. ID. NO. 36), respectively, contain a NotI site (underlined). The reverse primer for cloning ELG5 provides the translation stop codon. The reverse primer for cloning ELG5/V5-His only contains 2 of the 3 bases of the stop codon, therefore, placing the gene in frame with the tag provided by the vector.

PCR was carried out using Advantage-HF polymerase (Clontech) as per the manufacturer's instructions. The Pro-Quest human liver cDNA library (Gibco BRL) was used as the DNA template.

The PCR products were gel purified, digested with BamHI and NotI, and ligated into pYES2/CT cut with the same enzymes. The ligation products were used to transformed E. coli strain TOP10 (his were isolated and their inserts were sequenced. Plasmids coding for ELG5 and ELG5/V5-His were designated pTh1018.1 and pTh1019. 1, respectively.

Example 6

Cloning ELG6

ELG6 was cloned into the pYES2/CT yeast expression vector (Invitrogen) using PCR. Two plasmid constructions were made for the production of the ELG6 protein with either a C-terminal tag containing the V-5 epitope and polyhistidine peptide (ELG6/V5-His), or the ELG6 protein without the tag (ELG6). The forward primer (5'-CACGCG GGATCCAAAAATGGTCACAGCCATGAATGTCTC-3') (SEQ. ID. NO. 37) contains the translation start codon and a BamHI site (underlined). The reverse primers for cloning ELG6 and ELG6/V5-His, 5'-ATATCACGAT GCGGCCGCTCACTGGCTCTTGGTCTTGGC-3' (SEQ.

ID. NO. 38) and 5'-ATATCACGAT GCGGCCGCCACTGGCTCTTGGTCTTGGC-3' (SEQ. ID. NO. 39), respectively, contain a NotI site (underlined). The reverse primer for cloning ELG6 provides the translation stop codon. The reverse primer for cloning ELG6/V5-His only contains 2 of the 3 bases of the stop codon, therefore, placing the gene in frame with the tag provided by the vector.

PCR was carried out using Advantage-HF polymerase (Clontech) as per the manufacturer's instructions. The SuperScript human leukocyte cDNA library (Gibco BRL) was used as the DNA template.

The PCR products were gel purified, digested with BamHI and NotI, and ligated into pYES2/CT cut with the same enzymes. The ligation products were used to transform E. coli strain TOP10 (Invitrogen). Plasmids were isolated and their inserts were sequenced. Plasmids coding for ELG6 and ELG6/V5-His were designated pTh1041.1 and pTh1042.1, respectively.

Example 7

Cloning ELG7

ELG7 was cloned into the pYES2/CT yeast expression vector (Invitrogen) using PCR. Two plasmid constructions were made for the production of the ELG7 protein with either a C-terminal tag containing the V-5 epitope and polyhistidine peptide (ELG7/V5-His), or the ELG7 protein without the tag (ELG7). The forward primer (5'-CACGCG GGATCCAAAAATGGGGCTCCTGGACTCGGAGC-3') (SEQ. ID. NO. 40) contains the translation start codon and a BamHI site (underlined). The reverse primers for cloning ELG7 and ELG7/V5-His, 5'-ATATCACGAT GCGGCCGTTAATCTCCTTTTGCTTTTCCATTTTCT GC-3' (SEQ. ID. NO. 41) and 5'-ATATCACGAT GCGGCCGCTTATCTCCTTTTGCTTTTCCATTTTCT GC-3'(SEQ. ID. NO. 42), respectively, contain a NotI site (underlined). The reverse primer for cloning ELG7 provides the translation stop codon. The reverse primer for cloning ELG7/V5-His only contains 2 of the 3 bases of the stop codon, therefore, placing the gene in frame with the tag provided by the vector.

PCR was carried out using Platinum Taq DNA polymerase (Gibco BRL) as per the manufacturer's instructions. The SuperScript human leukocyte cDNA library (Gibco BRL) was used as the DNA template.

The PCR products were gel purified, digested with BamHI and NotI, and ligated into pYES2/CT cut with the same enzymes. The ligation products were used to transform E. coli strain TOP10 (Invitrogen). Plasmids were isolated and their inserts were sequenced. Plasmids coding for ELG7 and ELG7/V5-His were designated pTh1044.1 and pTh1045.1, respectively.

Example 8

Determination of Tissue Distribution by Northern Blot Analysis

A membrane containing poly(A)+ RNA from 12 different human tissues (brain, heart, skeletal muscle, colon, thymus, spleen, kidney, liver, small intestine, placenta, lung and peripheral blood leukocytes) was purchased from Clontech (Human 12-lane MTN blot). Northern blot analysis was carried out using standard procedures (Ausubel et al. 1994-, *Current Protocols in Molecular Biology*, John Wiley & Sons, NY). The hybridization solution contained 10% dextran sulphate. Probes were prepared by labelling cDNA using [alpha-$^{32}$P]dCTP and Rediprime II Random Prime Labelling System (Amersham Pharmacia Biotech). The cDNA probes for ELG1, ELG3, ELG5, and ELG6 corresponded to the complete CDS for the genes. The cDNA probes for ELG2, ELG4 and ELG7 corresponded to bases 209-514, 408-726 and 113-566 of the CDS, respectively. The membrane was washed at high stringency using 0.25× SSC, 0.1% SDS at 55° C.

Example 9

Cloning Human ELG1 Control Region

The ELG1 control region (989 bp) is cloned from human leukocyte genomic DNA by PCR. The control region is amplified by PCR using synthetic forward and reverse primers starting at positions −2865 bp and −1877 bp upstream from the translation initiation codon, ATG. The forward and reverse primers used for cloning human ELG1 control region by PCR amplification are 5'-GGA AGATCTTACAGGCTCGTGAGGCTTCCCTCCCG-3' (SEQ. ID. NO. 43) and 5'-GGA AGATCTCCGGCAGGAGGGACCAAGGCT-3' (SEQ. ID. NO. 44), respectively. The BglII recognition sequence (underlined) is included to facilitate cloning.

The PCR amplification is performed in a Perkin-Elmer GeneAMP PCR system 9700 instrument. For example, the PCR is performed in a 50 µl reaction volume containing 0.5 µg of genomic DNA, 0.4 µM of each primer, 1× dNTP mix (Clontech, CA), 1× cDNA PCR reaction buffer (Clontech) and 1× Advantage cDNA polymerase mix (Clontech).

The conditions for the PCR reaction are:

7 cycles at 94° C. for 2 seconds, 72° C. for 3 minutes
32 cycles at 94° C. for 2 seconds, 67° C. for 3 minutes
67° C. for 4 minutes The PCR product is gel-purified using QIAquick gel extraction kit (Qiagen, Germany) and ligated into the TA cloning vector pCRII (Invitrogen) according to manufacturers instruction. The ligation product is used to transform E. coli TOP10 strain (Invitrogen). The resulting plasmids are screened by restriction analysis and confirmed by DNA sequencing. The human EL1 control region is then recloned from the pCRII/ELG1 control region construct into the luciferase reporter vector pGL3-Basic (Promega). The resulting human ELG1 control region/reporter construct is used to transfect different mammalian cell lines, and reporter activity measured.

Example 10

Cloning Human EG2 Control Region

The ELG2 control region (509 bp) is cloned from human leukocyte genomic DNA by PCR. The control region is amplified by PCR using synthetic forward and reverse primers starting at positions −53626 bp and −53118 bp upstream from the translation initiation site, ATG. The forward and reverse primers used for cloning human ELG2 control region by PCR amplification are 5'-GGA AGATCTCGAGGGTGGGCTTCTGCCACCC-3' (SEQ. ID. NO. 45) and 5'-GGA AGATCTCTTTTAGCCCAAGGGGCGGCAGC-3' (SEQ. ID. NO. 46), respectively. The BglII recognition sequence (underlined) is included to facilitate cloning.

The PCR amplification and cloning are performed as described in Example 9.

The resulting human ELG2 control region/reporter construct is used to transfect different mammalian cell lines, and reporter activity measured.

Example 11

Cloning of the Human ELG3 Control Region

The human ELG3 control region was cloned from human leukocyte genomic DNA by nested PCR. Blood was obtained from volunteers in the present inventors' laboratory and used to prepare genomic DNA that served as template. In the first PCR reaction, synthetic forward and reverse primers starting at position −2025 bp and −1 bp, respectively, upstream from the translation initiation codon, ATG of the ELG3 gene were used. The forward and reverse primers were 5'-GGA AGATCTTTCGTGTGAATTTCCTTCAAGTCTC-3' (SEQ. ID. NO. 47) and 5'-GGA AGATCTTGATCCGCAGCGGCTGTG-3' (SEQ. ID. NO. 48), respectively. The BglII recognition sequence (underlined) was included to facilitate cloning.

The PCR amplification was conducted in a Perkin-Elmer GeneAMP PCR system 9700 instrument, in a 50 µl reaction volume containing 0.5 µg of genomic DNA, 0.4 µM of each primer, 1× dNTP mix (Clontech, CA), 1× cDNA PCR reaction buffer (Clontech) and 1× Advantage cDNA polymerase mix (Clontech).

The conditions for the PCR reaction were:
7 cycles at 94° C. for 2 seconds, 72° C. for 3 minutes
32 cycles at 94° C. for 2 seconds, 67° C. for 3 minutes
67° C. for 4 minutes Analysis of the PCR product by agarose gel electrophoresis revealed that at least two primer specific bands of about 2 kb were amplified. This result necessitated the use of the PCR products as a template and a new set of internal primers in a second PCR reaction to generate a unique primer specific band corresponding to the ELG3 control region. The internal forward and reverse primers start at positions −1381 and −37 respectively, upstream from the translation initiation codon, ATG. The internal forward and reverse primers used were 5'-GGA AGATCTCCGGTACCTACAGTTACTCACTCTGC-3' (SEQ. ID. NO. 49) and 5'-GGA AGATCTGGCGATGCGCTGTCCAGGGTA-3' (SEQ. ID. NO. 50).

The conditions for PCR reaction described herein were used for the second PCR reaction except for the following modifications: the second temperature cycle was lowered from 32 to 22 cycles, Taq DNA polymerase was substituted for cDNA polymerase and Q solution (Qiagen) was used according to manufacturer's instruction.

Figure 20:
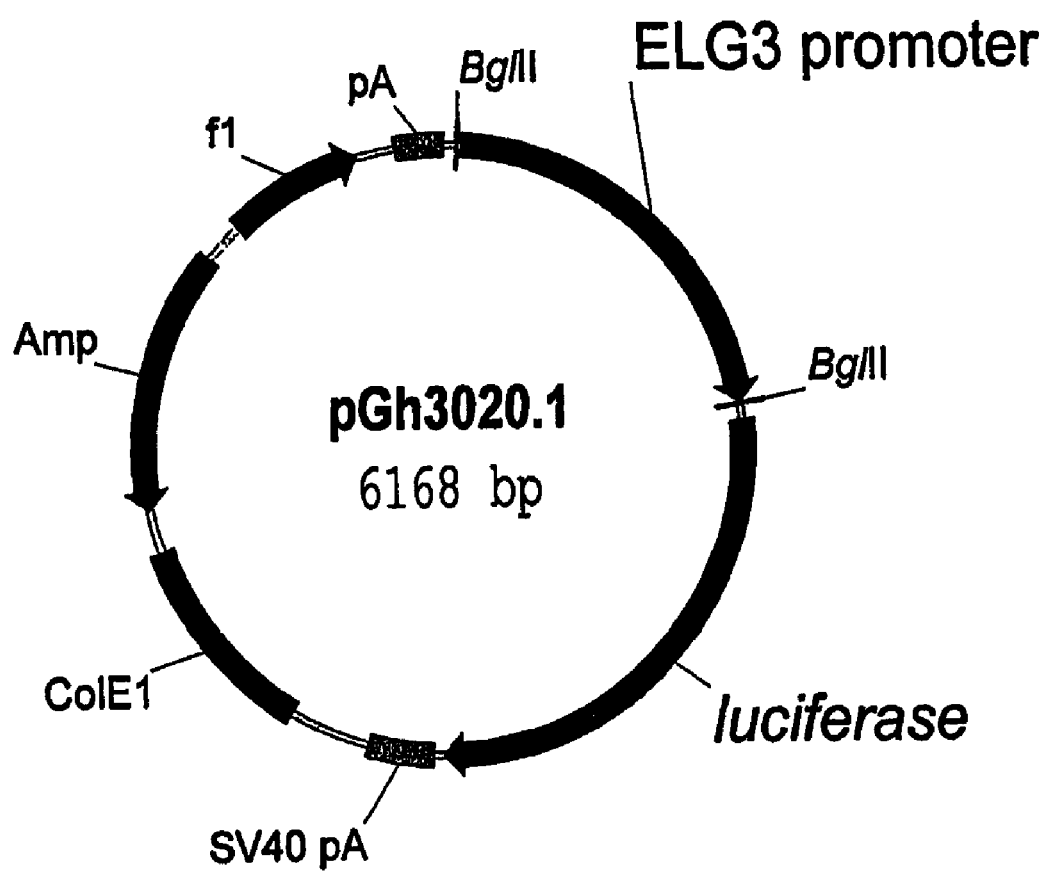
FIG. 20 is a schematic representation of plasmid pGh3020.1 (6168 bp). The control region for human elongase (ELG3) is shown between two BglII restriction sites.

The PCR product was gel-purified using QIAquick gel extraction kit (Qiagen). The purified PCR product and the reporter vector pGL3-Basic were separately digested with BglII restriction enzyme to generate compatible ends suitable for in-frame ligation of the PCR product to the luciferase gene of pGL3-basic. The ligation product was used to transform *E. coli* TOP10 strain (Invitrogen). The resulting plasmid, pGh3020.1 (FIG. 20), was screened by restriction analysis and confirmed by DNA sequencing. The resulting human ELG3 control region/reporter construct is used to transfect different mammalian cell lines, and reporter activity measured.

Example 12

Cloning Human ELG4 Control Region

The ELG4 control region (2456 bp) is cloned from human leukocyte genomic DNA by PCR. The control region is amplified by PCR using synthetic forward and reverse primers. The forward and reverse primers used for cloning human ELG4 control region by PCR amplification are 5'-CG ACGCGTTGCGCCTGGCTGAACACTAC-3' (SEQ. ID. NO. 51) and 5'-GGA AGATCTCTGGGACAAACAACAGGC-3' (SEQ. ID. NO. 52), respectively. The MluI and BglII recognition sequences (underlined), respectively, are included to facilitate cloning.

The PCR amplification and cloning are performed as described in Example 9.

The resulting human ELG4 control region/reporter construct is used and to transfect different mammalian cell lines, and reporter activity measured.

Example 13

Cloning Human ELG5 Control Region

The ELG5 control region (1411 bp) is cloned from human leukocyte genomic DNA by PCR. The control region is amplified by PCR using synthetic forward and reverse primers starting at positions −1411 bp and −1 bp upstream the translation initiation codon, ATG. The forward and reverse primers used for cloning human ELGS control region by PCR amplification are 5'-CCG CTCGAGGTGAGCCACCACCGCGGCC-3' (SEQ. ID. NO. 53) and 5'-CCG CTCGAGTGGGGCTGATCTTCGGAGTCGC-3' (SEQ. ID. NO. 54), respectively. The XhoI recognition sequence (underlined) is included to facilitate cloning.

The PCR amplification and cloning are performed as described in Example 9.

The resulting human ELG5 control region/reporter construct is used to transfect different mammalian cell lines, and reporter activity measured.

Example 14

Cloning Human ELG6 Control Region

The ELG6 control region (1937 bp) is cloned from human leukocyte genomic DNA by PCR. The control region is amplified by PCR using synthetic forward and reverse primers starting at positions −1937 bp and −1 bp upstream the initiation codon, ATG. The forward and reverse primers used for cloning human ELG6 control region by PCR amplification are 5'-CC GAGCTCGATTAGCTGTCAGGCTATATATGGAGCC-3' (SEQ. ID. NO. 55) and 5'-CC GAGCTCCTAGTTTGCAGAAGGTCCAAAGC-3' (SEQ. ID. NO. 56), respectively. The SacI recognition sequence (underlined) is included to facilitate cloning.

The PCR amplification and cloning are performed as described in Example 9.

The resulting human ELG6 control region/reporter construct is used to transfect different mammalian cell lines, and reporter activity measured.

Example 15

Cloning Human-ELG7 Control Region

The ELG7 control region (2006 bp) is cloned from human leukocyte genomic DNA by PCR. The control region is amplified by PCR using synthetic forward and reverse primers starting at positions −2000 bp and −1 bp upstream the translation initiation codon, ATG. The forward and reverse primers used for cloning human ELG7 control region by PCR amplification are 5'-CC GAGCTCGGAAATACCTGAAGCTGTTTTAAC-3' (SEQ. ID. NO. 57) and 5'-CC GAGCTCCGCGGCGATGAGCGGGC-3' (SEQ. ID. NO. 58), respectively. The SacI recognition sequence (underlined) is included to facilitate cloning.

The PCR amplification and cloning are performed as described in Example 9.

The resulting human ELG7 control region/reporter construct is used to transfect different mammalian cell lines, and reporter activity measured.

Example 16

Drug Screening Assay Using ELG3 Control Region

Plasmid pGh3020.1 (FIG. 20), containing the ELG3 control region, is used to screen test compounds that modulate the ELG3 promoter activity. Transient transfections are performed to evaluate the functionality of the ELG3 control region using techniques known by persons skilled in the art.

Alternatively, HepG2 cells are stably transfected with 10 µg of pGh3020.1 and 1 µg of vector pRSV-NEO (ATCC), using 10 µl of Lipofectamine 2000 Reagent (Gibco BRL) in a 60 mm tissue culture dish as described by the manufacturer. After a 24 h incubation, the cells are passaged into two 150 mm tissue culture dishes at a 1:2 dilution and grown for another 24 h. Geneticin (Gibco BRL) is added to the medium at a concentration of 800 µg/ml. After 3-4 weeks of growth under the selection pressure of the antibiotic, the resistant clones are isolated and characterized for their luciferase activity.

Drug screening is performed using the Luciferase Enzyme Assay System (Promega), following the manufacturer's recommendations. Briefly, transfected cells grown in a 96 well plate are exposed to test compounds. After an appropriate incubation time, the cells are washed with $Mg^{2+}$ and $Ca^{2+}$ free PBS. Cells are lysed with 20 µl of 1× Luciferase Cell Culture Lysis Reagent (CCLR, Promega). The plate is placed into a luminometer with an automatic injector. For each well, the injector adds 100 µl of Luciferase Assay Reagent (Promega), and the light emission generated by the reaction is read for 10 seconds after a 2 second delay. Cell cultures without a test compound are used as controls. Any significant difference in the luciferase activity indicates that the test compound is modulating the ELG3 promoter activity.

This assay or other reporter assays are suitable for drug-screening using the control region of any elongase gene.

Example 17

Drug Screening Assays Using Yeast One-Hybrid Systems

Methods for yeast one-hybrid assays are known by persons skilled in the art (Fields S. and Song O., 1989, *Nature*, 340: 245-246 and Ulmasov et al., 1997, *Science*, 276: 1865-1868). Reagents and/or kits are commercially available for the assays, e.g., the Matchmaker One-Hybrid System (Clontech).

This assay is suitable for all of the elongase control regions described herein.

The known target elements, or elongase control region 'bait' is inserted upstream of a reporter gene (e.g. HIS3) and integrated into the yeast genome to make a new reporter strain. The yeast strain is transformed with an activation domain (AD) fusion library to screen for DNA binding proteins that interact with the bait DNA sequence. Binding of an AD/DNA-binding domain (DBD) hybrid protein to the target sequence results in activation of the reporter gene transcription and subsequent selection. For example, expression of HIS3 will allow colony growth on minimal medium lacking histidine. The cDNA encoding DNA binding protein (DBP) is isolated and characterized. The interaction is reconstructed in vitro or in vivo for screening test compounds by exposing the target elements or elongase control region to the DBP in the presence of test compounds. The effect of the test compound is evaluated through assays, well known to those skilled in the art, that measure DNA/protein binding interactions.

Example 18

Drug Screening Assays Using Yeast Two-Hybrid Systems

Methods for the yeast two-hybrid assays are known by persons skilled in the art (Fields S. and Song O., 1989, *Nature*, 340: 245-246 and Furuyama K. and Sassa S., 2000, *J. Clin. Invest.*, 105: 757-764). Reagents and/or kits are commercially available for the assays, e.g., the Hybrid Hunter Yeast Two-Hybrid (Invitrogen), the Matchmaker Two-Hybrid Systems (Clontech) and the HybriZAP Two Hybrid System (Stratagene).

This assay is suitable for all of the elongase genes disclosed herein.

Two physically distinct functional domains are necessary: a DNA binding domain (DBD) and an activation domain (AD). The elongase polypeptide of interest is cloned into a "bait" vector, and expressed as a hybrid protein with a DBD. A library of cDNAs encoding potential interacting proteins is cloned in frame with AD in the "prey" vector. The bait and prey vector fusion constructs are transformed into one of several engineered yeast strains. If an interaction between bait and prey hybrid proteins occurs, the AD of the prey is brought into close contact with the DBD and transcription of the reporter genes is activated. Positive interacting proteins are easily identified by plating on nutrient deficient medium, and screening for reporter activity.

The interaction between these two proteins is reconstructed in vitro or in vivo for screening test compounds by exposing the two interacting proteins to test compounds. The effect of the test compound is evaluated through assays, well known to those skilled in the art, that measure protein/protein binding interactions.

Example 19

Functional Analysis of Human Elongases in *Saccharomyces cerevisiae*

The example presented herein demonstrates that the human elongase genes, ELG1, ELG2, ELG3, ELG4, ELG5, ELG6 and ELG7 cloned by the inventors, encode enzymes able to elongate, by at least two carbons, n-3 and/or n-6 fatty acid substrates.

Materials

Lithium [1-$^{14}$C]8:3n-6, [1-$^{14}$C]18:3n-3, [1-$^{14}$C]20:4n-6, and [1-$^{14}$C]20:5n-3 (99% radiochemical purity; specific activity: 48 to 58 µCi/µmol), were purchased from NEN (Boston, Mass.). All unsaturated fatty acids were saponified with 0.1 M LiOH and dissolved in a synthetic minimal medium lacking uracil (SC-U) with 1% tergitol.

Fatty acid free bovine serum albumin, tergitol, Tris-HCl, carbohydrates, amino acids and fatty acids were obtained from Sigma-Aldrich Canada (ON, Canada). Yeast nitrogen base without amino acids was purchased from Difco (Becton Dickinson). All organic solvents (HPLC grade) were obtained from Fisher-Scientific (Fair Lawn, N.J.).

Yeast Transformation

*Saccharomyces cerevisiae* strain INVSc1 (Invitrogen) was transformed with the elongase constructs previously described (Examples 1-7) or pYES2/CT using the lithium acetate method as supplied by Invitrogen. For the expression of ELG1, ELG2, ELG3, ELG4, ELG5, ELG6 or ELG7 the yeast were transformed with pTh1009.1, pTh1014.1, pTh1015.1, pTh1021.1, pTh1018.1, pTh1041.1 or pTh1044.1, respectively. For the expression of ELG1/V5-His, ELG2/V5-His, ELG3/V5-His, ELG4/V5-His, ELG5/V5-His, ELG6/V5-His or ELG7/V5-His the yeast were transformed with pTh1009.2, pTh1014.2, pTh1017.1, pTh1021.2, pTh1019.1, pTh1042.1 or pTh1045.1, respectively. Recombinant yeast cells were selected on SC-U medium.

Incubation

Transformed yeast (approximately 3.2×10$^6$ cells/ml; O.D.$_{600}$ 0.4) were incubated in a 125 ml Erlenmeyer containing 10 ml of SC-U medium with 1% raffinose, 1% tergitol and 25 µM of the lithium salts of either [1-$^{14}$C]18:3n-3 (1 µCi), [1-$^{14}$C]18:3n-6 (1 µCi), [1-$^{14}$C]20:4n-6 (2 µCi), or [1-$^{14}$C]20:5n-3 (2 µCi). After 4 h incubation in an orbital incubator at 270 rpm and 30° C., cells reached the log phase and the transgene, expression was induced with galactose 30° C., cells reached the log phase and the transgene expression was induced with galactose (2% final concentration). The yeast were incubated for an additional 19 h and then harvested by centrifugation at 5000×g for 10 minutes at 4° C.

Cells were washed with Tris-HCl buffer (100 mM, pH 8.0) containing 0.1% BSA and total lipids were extracted as described below. The radioactivity from aliquots of the incubation medium, supernatant and cells was determined by liquid scintillation counting using a LS6500-Scintillation System (Beckman).

The host yeast transformed with pYES2/CT was used as negative control.

Lipid Extraction

Total lipids were extracted from cells with chloroform/methanol (2:1 v/v) according to the method of Folch et al., 1957, *J. Biol. Chem.*, 226: 497-509. Alternatively, cells were resuspended in 1.5 ml of water and saponified with 2 ml of 10% KOH in ethanol. The total lipid extracts or the free fatty acids from the saponified samples were methylated using boron trifluoride in methanol at 90° C. for 30 min. The resultant methyl esters (FAME) were analyzed as described below.

Reverse Phase-High Performance Liquid Chromatography (RP-HPLC) Analysis

Analyses of radiolabelled FAME were carried out on a Hewlett Packard 1090, series II chromatograph equipped with a diode array detector set at 205 nm, a radioisotope detector (model 171, Beckman, CA) with a solid scintillation cartridge (97% efficiency for $^{14}$C-detection) and a reverse phase ODS (C-18) Beckman column (250 mm×4.6 mm i.d.; 5 µm particle size) attached to a pre-column with a µBondapak C-18 (Beckman) insert. FAME were separated isocratically with acetonitrile/water (95.5 v/v) at a flow rate of 1 ml/min and were identified by comparison with authentic standards. Alternatively, the eluted FAME were collected and the solvent evaporated. FAME were re-dissolved in hexane for further analysis by gas chromatography.

Gas Chromatography (GC) Analysis

The FAME profile was determined using a Hewlett Packard Gas Chromatograph equipped with an interfaced ChemStation, a flame-ionization detector and a 30 m×0.25 mm i.d. fused silica column (HP-wax, cross linked polyethylene glycol, film thickness 0.25 µm) and He as gas carrier. The temperatures of the injector and detector were maintained at 225° C. and 250° C., respectively. After an initial hold of 1 min at 180° C., the column temperature was increased by 4° C./min to 190° C. (7 min hold), then by 10° C/min to 200° C. (5 min hold) and finally by 25° C./min to 215° C. This temperature was maintained for 17.9 min. FAME were identified by comparison with authentic standards.

Results

Figure 22:
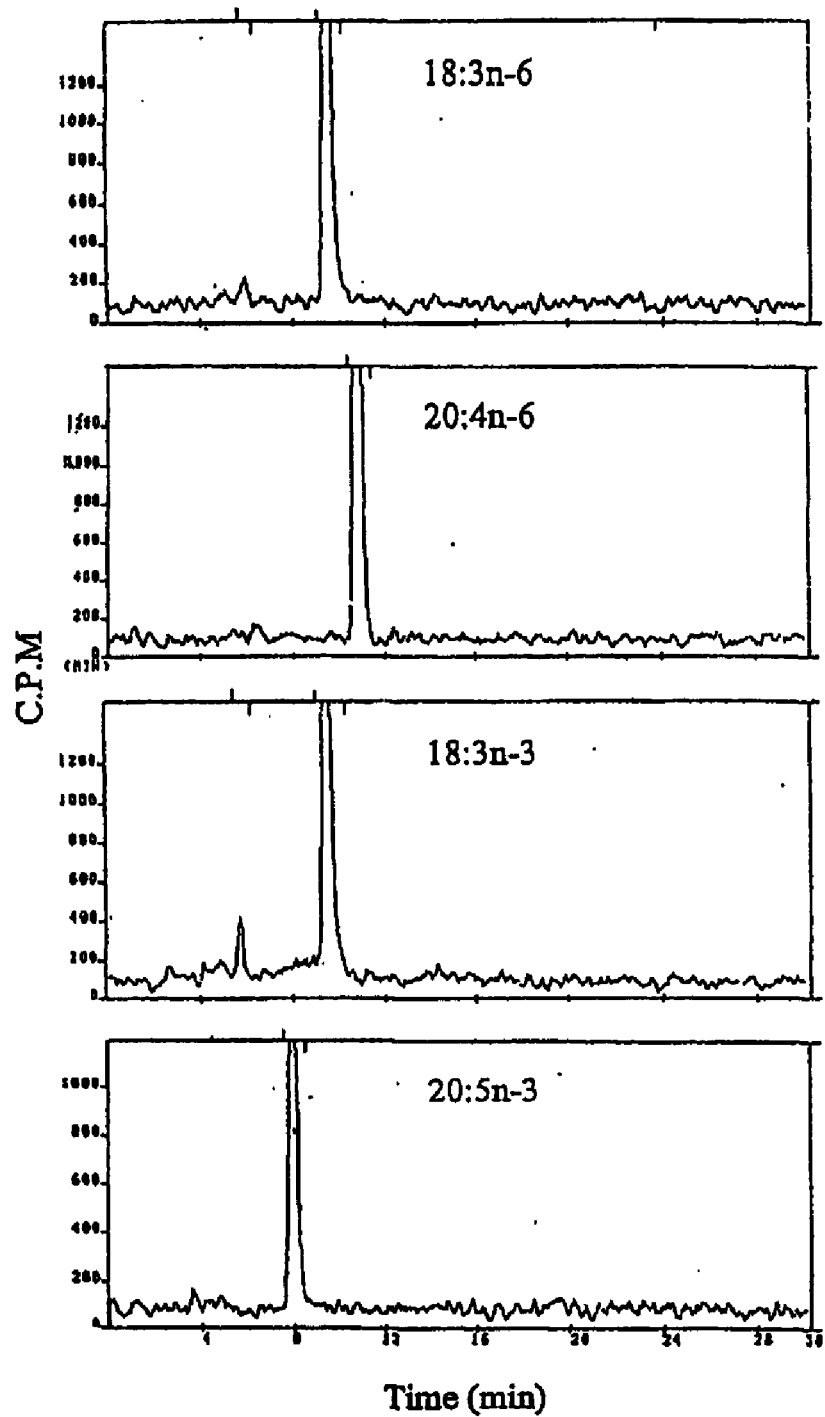
FIG. 22 shows an HPLC analysis of radiolabelled methyl esters of fatty acids from yeast transformed with pYES2/CT incubated with [1-$^{14}$C]18:3n-6, [1-$^{14}$C]20:4n-6, [1-$^{14}$C]18:3n-3 and [1-$^{14}$C]20:5n-3.

RP-HPLC analyses revealed that the exogenously added radiolabelled polyunsaturated fatty acids were elongated by at least two carbons in yeast transformed with human elongase genes (Table 3). In yeast expressing ELG4, 18:3n-6 was converted into 20:3n-6 which was then elongated to 22:3n-6, 20:4n-6 was converted into 22:4n-6 which was further elongated to 24:4n-6 and 18:3n-3 was converted into 20:3n-3 and 22:3n-3 (FIG. 21). Yeast transformed with pYES2/CT did not elongate any of these substrates (FIG. 22).

In yeast expressing elongases with V5-His tag, the percent elongation of selected substrates was similar to that detected in yeast with non-tagged enzymes (Table 4).

Conclusion

The functional analysis of the human ELG1, ELG2, ELG3, ELG4, ELG5, ELG6 and ELG7 genes confirmed that each gene encodes a fatty acid elongase which is active on various PUFAs.

TABLE 3

Percent Elongation of PUFA Substrates to their Products in Yeast Expressing Human Elongases

| | | 18:3n-6 | | 20:4n-6 | | 18:3n-3 | | 20:5n-3 | |
|---|---|---|---|---|---|---|---|---|---|
| Gene | Plasmid | 20:3 | 22:3 | 22:4 | 24:4 | 20:3 | 22:3 | 22:5 | 24:5 |
| ELG1 | pTh1009.1 | 2 | nd | 6 | 2 | 1 | nd | 2 | nd |
| ELG2 | pTh1014.1 | 62 | 3 | 39 | 1 | 16 | nd | 59 | nd |
| ELG3 | pTh1015.1 | 10 | nd | 11 | 21 | 2 | nd | 16 | 29 |
| ELG4 | pTh1021.1 | 20 | 4 | 24 | 2 | 10 | 4 | 15 | 3 |
| ELG5 | pTh1018.1 | 3 | nd | nd | nd | 9 | nd | — | — |

TABLE 3-continued

Percent Elongation of PUFA Substrates to their Products in Yeast Expressing Human Elongases

| Gene | Plasmid | 18:3n-6 | | 20:4n-6 | | 18:3n-3 | | 20:5n-3 | |
|---|---|---|---|---|---|---|---|---|---|
| | | 20:3 | 22:3 | 22:4 | 24:4 | 20:3 | 22:3 | 22:5 | 24:5 |
| ELG6 | pTh1041.1 | 2 | nd | nd | nd | 3 | nd | nd | nd |
| ELG7 | pTh1044.1 | nd | nd | nd | nd | 5 | nd | nd | nd | nd: not detected
—: not tested

TABLE 4

Percent Elongation of PUFA Substrates to their Products in Yeast Expressing V5-His Tagged Human Elongases

| Gene | Plasmid | 18:3n-6 | | 20:4n-6 | | 18:3n-3 | | 20:5n-3 | |
|---|---|---|---|---|---|---|---|---|---|
| | | 20:3 | 22:3 | 22:4 | 24:4 | 20:3 | 22:3 | 22:5 | 24:5 |
| ELG1 | pTh1009.2 | — | — | 7 | nd | — | — | — | — |
| ELG2 | pTh1014.2 | 73 | 11 | — | — | — | — | — | — |
| ELG3 | pTh1017.1 | — | — | 8 | 15 | — | — | — | — |
| ELG4 | pTh1021.2 | — | — | 12 | nd | — | — | — | — |
| ELG5 | pTh1019.1 | 5 | — | — | — | — | — | — | — |
| ELG6 | pTh1042.1 | nd | nd | Nd | nd | 3 | nd | nd | nd |
| ELG7 | pTh1045.1 | nd | nd | Nd | nd | 4 | nd | nd | nd | nd: not detected
—: not tested

Example 20

Drug Screening Assay for Elongases Using Yeast

This example provides a methodology suitable for screening test compounds that modulate the activity of recombinant elongases in whole cells and spheroplasts of *Saccharomyces cerevisiae*. The test compound uptake is likely to be enhanced in yeast spheroplasts due to their lack of a cell wall. Thus, this is the model of choice for assessing the effect of low concentrations of test compounds on elongase activity.

Spheroplast Preparation

*Saccharomyces cerevisiae* heterologous for any of the human elongase genes are grown in SC-U medium with 1% raffinose and 2% galactose to induce the expression of the transgene. After 16 h incubation, cells are centrifuged at 2060×g for 5 min at 4° C., washed once with distilled water and centrifuged again. The volume and weight of the cell pellet are measured. Cells are suspended (1:2 w/v) in 0.1 M Tris.SO$_4$ (pH 9.4), 10 mM DTT and incubated at 30° C.

After 10 min incubation, the cell pellet is obtained by centrifugation, washed once (1:20 w/v) with 1.2 M sorbitol and suspended (1:1 w/v) in 1.2 M sorbitol, 20 mM phosphate buffer (pH 7.4) as described elsewhere (Daum et al., 1982, *J. Biol. Chem.*, 257: 13028-13033). A 15,800×g (1 min) supernatant of lyticase is added to the cell suspension at a concentration of 2000 U/ml and the suspension incubated at 30° C. with 50 rpm shaking. Conversion to spheroplasts is checked after 40 min incubation by diluting the suspension with distilled water followed by observation under the microscope (Schatz G. and Kovac L., 1974, *Meth. Enzymol.*, 31A: 627-632). After 70 min incubation, approximately 90% of the cells are converted to spheroplasts.

Incubation of Spheroplasts with Test Compounds

Spheroplasts are harvested by centrifugation at 2060×g for 5 min at 4° C. and washed once with 1.2 M sorbitol. Spheroplasts are resuspended in SC-U medium with 1% raffinose, 1% tergitol, 1.2 M sorbitol and 2% galactose to maintain the induction conditions and to give an O.D.$_{600}$ reading of approximately 2.5-3.0. A 10 ml aliquot of the sheroplast suspension is transferred to a 125 ml Erlenmeyer flask and incubated with 200 μl of a test compound in ethanol (e.g. pebulate sulphoxide with a final concentration ranging from 0.01 to 100 μM) at 30° C. in an orbital incubator at 270 rpm. After 30 min incubation, 1 μCi of a selected elongase substrate (i.e., lithium salts of [(1-$^{14}$C]18:3n-6, [1-$^{14}$C]20:4n-6, [1-$^{14}$C]20:5n-3 or [1-$^{14}$C]18:3n-3) is added to the culture to a final concentration of 2 to 200 μM and further incubated for 120 min. Cell density is determined (O.D.$_{600}$) and spheroplasts are harvested by centrifugation and washed with Tris-HCl buffer (100 mM, pH 8.0) containing 0.1% BSA. Total lipids are extracted and analyzed as described in Example 19.

Incubation of Whole Yeast with Test Compounds

*Saccharomyces cerevisiae* heterologous for any of the human elongase genes are incubated in a 125 ml Erlenmeyer flask containing 9 ml of SC-U medium with 1% raffinose, 1% tergitol (O.D.$_{600}$ 0.4, approximately 3.2×10$^6$ cells/ml) and 200 pi of a test compound in ethanol (e.g. pebulate sulphoxide, with a final concentration in the culture that range between 0.1 and 5 mM). After 1 h incubation in an orbital incubator at 270 rpm and 30° C., 1 μCi of a selected elongase substrate (i.e., lithium salts of [1-$^{14}$C]18:3n-6, [1-$^{14}$C]20:4n-6, [1-$^{14}$C]20:5n-3 or [1-$^{14}$C]18:3n-3) is added to the culture to a final concentration of 2 to 200 μM. After 4 h incubation with the inhibitor, cells reach the log phase and the transgene expression is induced with the addition of 1 ml of galactose to a final concentration of 2%. The yeast are incubated for an additional 19 h and then harvested by centrifugation at 5000×g for 10 minutes at 4° C. Cells are washed with Tris-HCl buffer (100 mM, pH 8.0) containing 0.1% BSA and total lipids are extracted and analyzed as described in Example 19.

Calculations

The elongase activity is determined by measuring the conversion of radiolabelled 18:3n-6 to 20:3n-6 and 22:3n-6, 20:4n-6 to 22:4n-6 and 24:4n-6, 18:3n-3 to 20:3n-3 and 22:3n-3 or 20:5n-3 to 22:5n-3 and 24:5n-3. The percent inhibition is calculated as described elsewhere (Kawashima et al., 1996, *Biosci. Biotech. Biochem.*, 60: 1672-7676):

% Inhibition=100(activity without the inhibitor−activity with the inhibitor)/activity without the inhibitor

Example 21

Drug Screening Assay for Elongase Using Yeast Microsomes

This example teaches that microsomes from yeast with elongase transgenes contain all the enzymes required for testing the effect of test compounds on the activity of a specific recombinant fatty acid elongase.

Materials

A sulphoxide derivative of S-propylbutylethylthiocarbamate (pebulate sulphoxide) was obtained from Zeneca Agrochemicals, UK, and dissolved in ethanol at a concentration of 5 mM.

Yeast Microsome Preparation

A 5 l culture of *Saccharomyces cerevisiae* transformed with pTh1017.1 encoding ELG3/V5-His was started with a cell density of approximately $3.2 \times 10^5$ cells/ml ($O.D._{600}$ 0.4) using SC-U medium with 1% raffinose. After 8 h of incubation at 30° C. in an orbital shaker at 270 rpm, galactose was added to a final concentration of 2%. Yeast were incubated for an additional 12 h until they were harvested by centrifugation at 2060×g for 10 minutes at 4° C. and washed with water. The cell pellet was resuspended in ⅓ of its volume in a pH 7.2 isolation buffer (80 mM Hepes-KOH, 10 mM KCl, 320 mM sucrose, 2 mM PMSF and a protease inhibitor cocktail). The cell suspension was poured into a mortar containing liquid $N_2$ and ground with sand using a ceramic pestle. The yeast powder was transferred to a conical test tube, to which ⅔ of the pellet volume of isolation buffer was added. The sand was removed by centrifugation at 228×g for 1 min and the suspension centrifuged at 10,000×g for 20 min to separate cell debris, nuclei and mitochondria. The supernatant was centrifuged at 106,000×g for 1.5 h to obtain the microsomal pellet, which was resuspended in storage buffer (80 mM Hepes-KOH, 10 mM KCl, 320 mM sucrose, 1 mM PMSF and a protease inhibitor cocktail) to a final protein concentration of 20 μg/μl. The protein concentration was measured by the method of Lowry et al. (1951, *J Biol. Chem.*, 193: 265-275) with bovine serum albumin as standard.

Incubation of Yeast Microsomes with Pebulate Sulphoxide

The activity of ELG3/V5-His was determined by measuring the conversion of [1-$^{14}$C]20:5n-3 to [1-$^{14}$C]22:5n-3 and [1-$^{14}$C]24:5n-3. Reactions were started by adding 500 μg of yeast microsomal protein to pre-incubated tubes containing 0.20 μCi of the substrate fatty acid at a final concentration of 7.2 μM in 0.25 ml of 80 mM Hepes-KOH (pH 7.2) with 43 mM $MgCl_2$, 1.0 mM ATP, 500 μM NADPH, 10 μM coenzyme A, 100 μM marinyl-CoA (as lithium salt) and pebulate sulphoxide at concentrations that ranged between 1 to 100 μM. The tubes were vortexed vigorously and after 30 min incubation at 37° C. in a shaking water bath, the reactions were stopped by the addition of 2 ml of 10% (w/v) KOH in ethanol. Lipids in the incubation mixture were saponified at 80° C. for 45 min under $N_2$. The samples were then left in ice for 5 min before acidification with 750 μl of concentrated HCl. The fatty acids were extracted with hexane and esterified with $BF_3$ in methanol at 90° C. for 30 min. The fatty acid methyl esters were analyzed by HPLC as described in Example 19.

Results

The enzyme activity was expressed in percent conversion of radiolabelled 20:5n-3 into its elongation products. Alternatively, it can be expressed in pmol of the fatty acids produced/mg microsomal protein/min.

Table 5 shows the effect of a thiocarbamate derivative (pebulate sulphoxide) on the ELG3/V5-His activity when 20:5n-3 was provided as substrate. Pebulate sulphoxide at 100 μM substantially reduced elongation, by approximately 27%. This effect was mainly due to a reduction in the synthesis of 22:5n-3 rather than in the production of its metabolite, 24:5n-3.

TABLE 5

Effect of Pebulate Sulphoxide on the Elongation of [1-$^{14}$C]20:5n-3 in Microsomes of Yeast Expressing ELG3/V5-His.

| Pebulate sulphoxide | % conversion | | |
|---|---|---|---|
| [μM] | 22:5n-3 | 24:5n-3 | Total |
| 0 | 13.7 | 5.0 | 18.7 |
| 1 | 13.8 | 5.6 | 19.4 |
| 10 | 12.8 | 6.6 | 19.4 |
| 50 | 11.3 | 4.6 | 15.9 |
| 100 | 9.4 | 4.3 | 13.7 |

Values expressed are the average (dispersion ≦ 10%) of two determinations.

Example 22

Isolation of Recombinant Elongases from Yeast

This example provides a methodology for the isolation of recombinant elongase from yeast homogenate or microsomes. The purified enzyme is useful for drug screening or for antibody production.

Yeast Homogenate and Microsome Preparations

Yeast cell fractionation was performed as described in Example 21 using yeast expressing ELG3/V5-His.

Elongase Solubilization

Yeast cell homogenate or yeast microsomes were resuspended in solubilization buffer (80 mM HEPES-KOH pH 7.2, 10 mM KCl, 320 mM sucrose, 1 mM PMSF, protease inhibitor cocktail, and 0.5 M NaCl) at 1.3 or 4 mg/ml, respectively. Zwittergent 3-14, n-octyl-beta-glucopyranoside or n-octyl-beta-thioglucopyranoside (Calbiochem, CA) was added to a final concentration of 2%, with a detergent: protein ratio of 15:1. The mixture was incubated for 2 h at 4° C. with stirring and then centrifuged at 106,000×g for 1 h. The supernatant was removed and stored at −80° C. until use. The pellet was resuspended in ¼ volume of the supernatant using solubilization buffer. The efficiency of each detergent to solubilize the elongase was determined by Western blot analysis as described below.

SDS-PAGE and Western Blot Analysis

Supernant (60 μl) or pellet suspension (20 μl) was mixed with 15 μl or 5 μl of 5× sample loading buffer (1× concentration: 50 mM Tris-HCl pH 8.0, 2% SDS, 10 mM beta-mercaptoethanol, 0.1% bromophenol blue, 10% glycerol), respectively, and boiled at 100° C. for 5 minutes. Molecular weight standards (Santa Cruz Biotechnology, CA), controls, 25 μl of the supernatant, and 12.5 μl of the pellet were loaded on 12% pre-cast SDS-polyacrylamide gels. After electrophoresis, the protein was electro-transferred onto a PVDF membrane (Bio-Rad). The membrane was incubated with a blocking solution and subsequently probed with an anti-V5-HRP antibody as recommended by the manufacturer (Invitrogen). The membrane was washed and the antibody was, detected using the enhanced chemiluminescence reagent, ECL (Amersham-Pharmacia Biotech.). The membrane was exposed to autoradiography film (Labscientific, NJ).

Zwittergent 3-14 was the most effective detergent in solubilizing ELG3/V5-His, the majority of the tagged protein having been detected in the 106,000×g supernatant.

Immobilized Metal Ion Affinity Chromatography (IMAC)

The supernatant containing the solubilized enzyme is loaded onto a pre-equilibrated HiTrap chelating ($Ni^{2+}$ charged iminodiacetate) column (Pharmacia) attached to a fast protein liquid chromatography system (Pharmacia). The column is washed with 50 mM sodium phosphate pH 8.0. The tagged protein is eluted with the same buffer containing imidazole ranging from 0 to 500 mM and further concentrated by ultrafiltration using Centriprep (Amicon) concentrators.

Alternatively, Macro-Prep ceramic hydroxyapatite (Bio-Rad, CA), TALON metal affinity resin (a Cobalt-based IMAC resin, Clontech, CA), Ni-nitriloacetic acid resin (Novagen, WI) or other similar resin is used.

Example 23

Drug Screening Assay for Elongase Using Purified Enzyme

The concentrated enzyme (Example 22) is incubated at 30-37° C. in 0.25 ml of 80 mM Hepes-KOH (pH 7.2) with 6 mM egg phosphatidylcholine, 2% Triton X-100, 0.4% sodium deoxycholate, 43 mM $MgCl_2$, 1.0 mM ATP, 500 μM NADPH, 10 μM coenzyme A, 100 μM malonyl-CoA (as lithium salt), 0.20 μCi of the substrate fatty acid (i.e., radiolabelled eicosapentaenoyl-CoA) at a final concentration of 7.2 μM and a test compound (e.g., pebulate sulphoxide) at concentrations ranging between 0.01 to 100 μM. The tubes are vortexed vigorously and after 30 min incubation at 37° C. in a shaking water bath the reactions are stopped by the addition of 2 ml of 10% (w/v) KOH in ethanol.

Total lipids are extracted and methyl ester analyzed as described in Example 19.

Example 24

Validation of Drug Screening Assays Described in Examples 20, 21 and 23 Using Rat Liver Microsomes Preparation of Rat Liver Microsomes Wistar rats under light halothane (15% in mineral oil) anesthesia were sacrificed by exsanguination during periods of high enzyme activity. Livers were immediately rinsed with cold 0.9% NaCl solution, weighed and minced with scissors. All procedures were performed at 4° C. unless specified-otherwise. Livers were homogenized in a solution (1:3 w/v) containing 0.25 M sucrose, 62 mM potassium phosphate buffer (pH 7.0), 0.15 M KCl, 1.5 mM N-acetyl-cysteine, 5 mM $MgCl_2$, and 0.1 mM EDTA using 4 strokes of a Potter-Elvehjem tissue homogenizer. The homogenate was centrifuged at 10,400×g for 20 min to pellet mitochondria and cellular debris. The supernatant was filtered through a 3-layer cheesecloth and centrifuged at 105,000×g for 60 min. The microsomal pellet was gently resuspended in the same homogenization solution with a small glass/teflon homogenizer and stored at −80° C. The absence of mitochondrial contamination was enzymatically assessed as described elsewhere (Kilberg, M. S. and Christensen H. N., 1979, *Biochemistry,* 18: 1525-1530). The protein concentration was measured by the method of Lowry et al (1951, *J. Biol. Chem.,* 193: 265-275) with bovine serum albumin as standard.

Incubation of Rat Liver Microsomes with Test Compounds

Reactions were performed using 500 μg of rat liver microsomal protein with the same concentrations of pebulate sulphoxide, radiolabelled fatty acid, conditions and procedures described in Example 21.

Results

The enzyme activity was expressed in percent conversion of radiolabelled 20:5n-3 into its elongation and final delta-6-desaturation products (i.e., 22:5n-3, 24:5n-3 and 24:6n-3). When the incubation was performed under nitrogen, the desaturation reaction did not occur.

Table 6 shows the effect of a thiocarbamate derivative (pebulate sulphoxide) on the rat liver elongase activity when 20:5n-3 was provided as substrate. Pebulate sulphoxide (100 μM) reduced elongation by approximately 30%. This effect was mainly due to a reduction in the synthesis of 24:5n-3 rather than in the synthesis of 22:5n-3.

TABLE 6

Effect of Pebulate Sulphoxide on the Elongation of [$1$-$^{14}$C]20:5n-3 in Rat Liver Microsomes

| Pebulate sulphoxide | % conversion | | | |
|---|---|---|---|---|
| [μM] | 22:5n-3 | 24:5n-3 | 24:6n-3* | Total |
| 0 | 11.6 | 39.7 | 9.1 | 60.4 |
| 1 | 12.5 | 47.5 | 9.6 | 69.3 |
| 10 | 12.5 | 47.2 | 10.9 | 70.7 |
| 50 | 12.2 | 48.7 | 7.9 | 68.8 |
| 100 | 10.2 | 28.0 | 4.5 | 42.7 |

Values are expressed as the mean (dispersion ≤ 10%) of two determinations.
*24:6n-3 is the product of a delta-6-desaturation of 24:5n-3.

Since the rat liver microsomal and the recombinant human elongase (Example 21) activities were similarly affected by pebulate sulphoxide, it is concluded that rat liver microsomes are suitable to use in the validation of drug screening assays.

Example 25

Functional Characterization of Recombinant Fatty Acid Elongase and Desaturase in Yeast Co-expressing ELG3 and D6D This example shows a partial reconstitution of the n-3 and n-6 polyunsaturated fatty acid biosynthetic pathway in a heterologous host such as *Saccharomyces cerevisiae* using human fatty acid elongase and desaturase genes.

Materials

[1-$^{14}$C]18:3n-3, [1-$^{14}$C]20:4n-6, [1-$^{14}$C]20:5n-3 and [1-$^{14}$C]18:2n-6 (99% radiochemical purity; specific activity: 51 to 56 µCi/µmol) were purchased from NEN (Boston, Mass.). Fatty acids were saponified with 0.1 M LiOH and dissolved in synthetic minimal medium lacking either leucine (SC-Leu) or uracil and leucine (SC-U-Leu), containing 1% tergitol.

Yeast Transformation

Saccharomyces cerevisiae strain INVSc1 (Invitrogen) was transformed using the lithium acetate method as supplied by Invitrogen. The coding sequence for human delta-6-desaturase (GenBank Accession No. AF126799) was previously cloned into the pYES2/CT vector for the production of the protein with a C-terminal tag containing the V-5 epitope and polyhistidine peptide (D6D/V5-His) as described in Canadian Patent Application No. 2,301,158, March, 2000, Winther et al. (plasmid designated pTh5002.1). For the co-expression of ELG3 and D6DN5-His, the yeast were initially transformed with pTh5002.1. Recombinant yeast cells were selected on SC-U medium and then transformed with pTh5015.1 (Example 3). Double recombinant yeast cells containing both pTh5002.1 and pLh5015.1 were selected on SC-U-Leu medium. Yeast cells transformed with pBEVY-L alone, the cloning vector for ELG3, were selected on SC-Leu medium.

Incubation

Transformed yeast cultures (approximately $3.2 \times 10^6$ cells/ml; O.D.$_{.600}$ 0.4) were divided in two experimental groups. The first group was incubated in a 125 ml Erlenmeyer flask containing 10 ml of SC-U-Leu medium with 2% raffinose, 1% tergitol and 25 µM lithium [1-$^{14}$C]20:4n-6 (1 µCi). Yeast of the second group were incubated in 10 ml of SC-U-Leu medium containing 1% raffinose, 2% galactose (to induce the expression of D6DN5-His) and 1% tergitol. Lithium salts (1 µCi) of either [1-$^{14}$C]18:3n-3, [1-$^{14}$C]20:4n-6, [1-$^{14}$C]20:5n-3 or [1-$^{14}$C]8:2n-6 were added to both experimental groups at a final concentration of 25 µM. After 24 h incubation in an orbital incubator at 270 rpm and 30° C., cells were harvested by centrifugation at 5000×g for 10 minutes at 4° C.

The cell pellet was washed with Tris-HCl buffer (100 mM, pH 8.0) containing 0.1% BSA total lipids were extracted and radiolabelled fatty acids analyzed as described in Example 19.

The host yeast transformed with pBEVY-L was used as negative control.

Results

Figure 23:
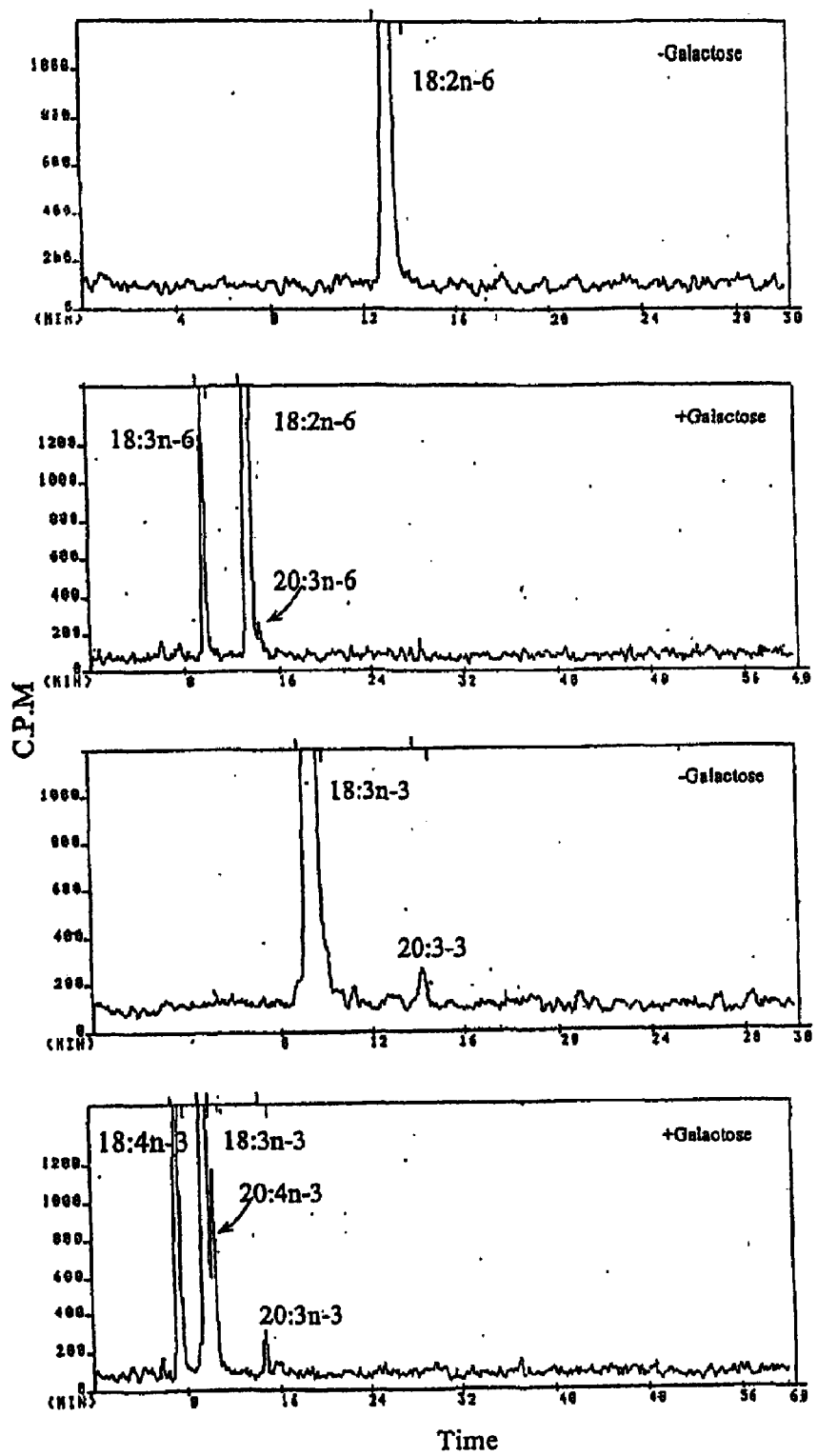
FIG. 23 shows an HPLC analysis of radiolabelled methyl esters of fatty acids from yeast co-expressing D6D/V5-His and ELG3, incubated with [1-$^{14}$C]18:2n-6 or [1-$^{14}$C]18:3n-3 and with or without galactose.
Figure 24:
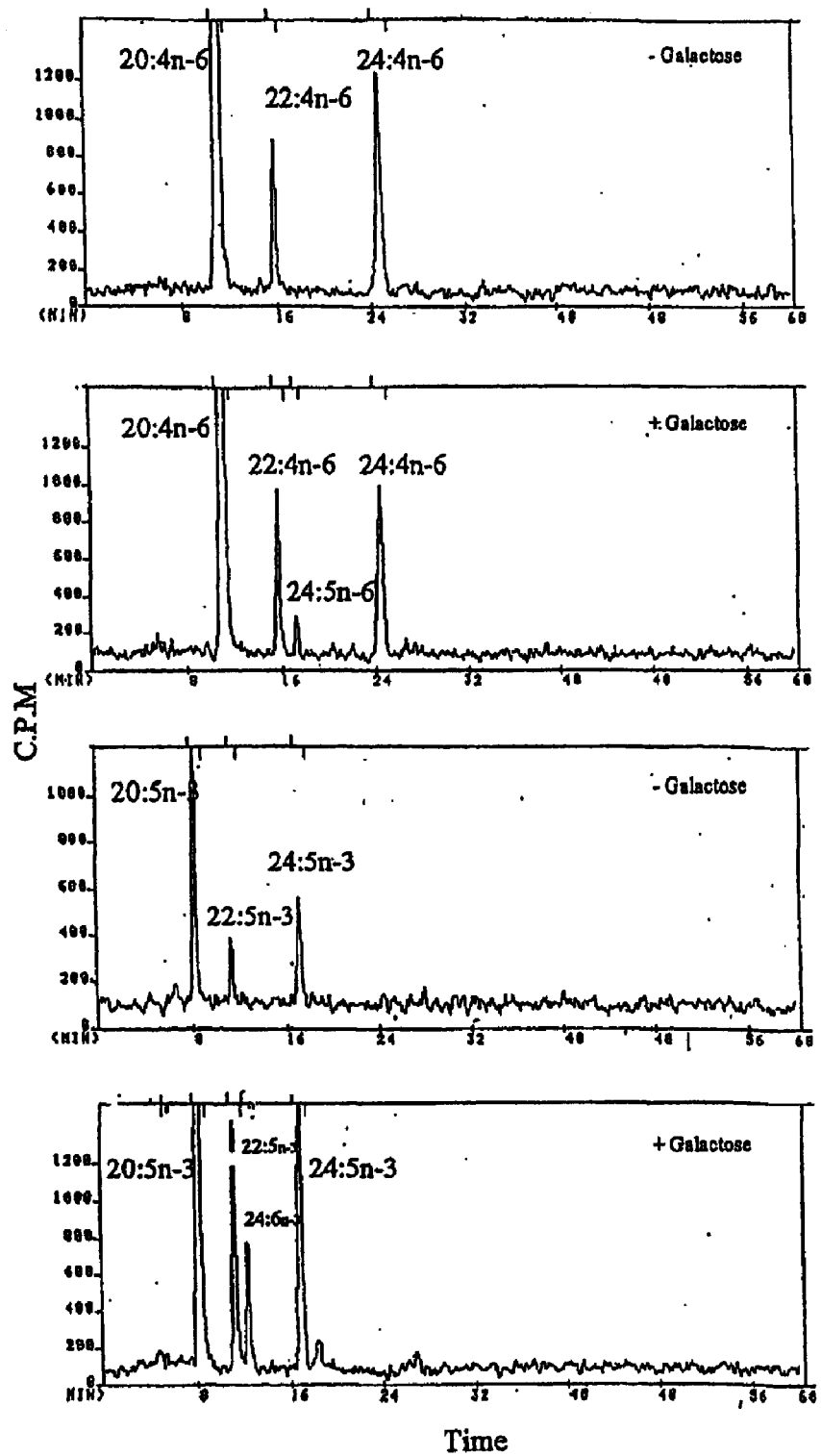
FIG. 24 shows an HPLC analysis of radiolabelled methyl esters of fatty acids from yeast co-expressing D6DN5-His and ELG3, incubated with [1-$^{14}$C]20:4n-6 or [1-$^{14}$C]20:5n-3 and with or without galactose.

FIGS. 23 and 24 show that only elongation products of PUFA substrates for ELG3 were detected when galactose was absent from the culture medium since the expression of D6DN5-His was not induced. The constitutively expressed ELG3 was able to elongate 20:4n-6 to 22:4n-6 and 24:4n-6, 20:5n-3 to 22:5n-3 and 24:5n-3, and to a lesser extent 18:3n-3 to 20:3n-3. These findings are consistent with those described in Example 19. ELG3 did not elongate 18:2n-6.

The elongation products of PUFA substrates for ELG3 were desaturated by D6DN5-His when galactose was added to the medium (FIG. 24). In this regard, 24:5n-6 and 24:6n-3 were produced from 24:4n-6 and 24:5n-3, respectively.

In the presence of galactose, transformed yeast were also able to delta-6-desaturate 18:2n-6 and 18:3n-3 to 18:3n-6 and 18:4n-3, respectively. These products were then substrates of the ELG3, which elongated them to 20:3n-6 and 20:4n-3, respectively.

Both ELG3 and D6D/V5-His seemed to be more active on n-3 than on n-6 fatty acid substrates.

Yeast transgenic for the human elongase, ELG3, and a human D6D, were able to generate polyunsaturated fatty acids of the so called "Sprecher pathway" (Sprecher H., 2000, Biochim. Biophys. Acta, 1486: 219-231). The present inventors are the first to report that products of human ELG3, 24:4n-6 and 24:5n-3, are substrates of a-human D6D, which is also active on 18:2n-6 and 18:3n-3.

Example 26

Functional Characterization of Recombinant Fatty Acid Elongase and Desaturase in Yeast Co-expressing ELG3 and D5D This example expands the inventors' findings described in Example 25. The sequential elongation and desaturation of n-3 and n-6 PUFAs in a heterologous host co-expressing human fatty acid elongase and D5D genes is demonstrated.

Materials

[1-$^{14}$C]18:3n-3, [1-$^{14}$C]20:3n-6 and [1-$^{14}$C]18:2n-6 (99% radiochemical purity; specific activity: 50 to 52 µCi/µmol) were purchased from NEN (Boston, Mass.). [1-$^{14}$C]-$\Delta^{8,11,14,17}$ eicosatetraenoic acid, 20:4n-3, (99% radiochemical purity; specific activity: 55 µCi/µmol) was purchased from ARC (St Louis, Mo.). Fatty acids were saponified with 0.1 M LiOH and dissolved in either SC-Leu or SC-U-Leu medium, containing 1% tergitol.

Yeast Transformation

Saccharomyces cerevisiae strain INVSc1 (Invitrogen) was transformed using the lithium acetate method as supplied by Invitrogen. The coding sequence for human delta-5-desaturase (GenBank Accession No. AF199596) was previously cloned into the pYES2/CT vector for the production of the protein with a C-terminal tag containing the V-5 epitope and polyhistidine peptide (D5D/V5-His) as described in Canadian Patent Application No. 2,301,158, March, 2000, Winther et al. (plasmid designated pTh5009.1). For the co-expression of ELG3 and D5DNV5-His, the yeast were initially transformed with pTh5009.1. Recombinant yeast cells were selected on SC-U medium and then transformed with pLh5015.1 (described in Example 3). Double recombinant yeast cells containing both pTh5009.1 and pLh5015.1 were selected on SC-U-Leu medium. Yeast cells transformed with pBEVY-L alone, the cloning vector for ELG3, were selected on SC-Leu medium.

Incubation

Cultures of transformed yeast (approximately $3.2 \times 10^6$ cells/ml; O.D.$_{.600}$ 0.4) were divided in two experimental groups. In the first group, cells were incubated in a 125 ml Erlenmeyer flask containing 10 ml of SC-U-Leu medium with 2% raffinose and 1% tergitol. In the second group, yeast were incubated in 10 ml of SC-U-Leu medium with 1% raffinose, 2% galactose (to induce the expression of D5D/V5-His) and 1% tergitol. Lithium salts (1 µCi) of either [1-$^{14}$C]18:3n-3, [1-$^{14}$C]20:3n-6, [1-$^{14}$C]18:2n-6, or [1-$^{14}$C]20:4n-3 were added to both experimental groups at a final concentration of 25 µM. After 24 h incubation in an orbital incubator at 270 rpm and 30° C., cells were harvested by centrifugation at 5000×g for 10

The cell pellet was washed with Tris-HCl buffer (100 mM, pH 8.0) containing 0.1% BSA, total lipids were extracted and radiolabelled fatty acids were analyzed as described in Example 19.

The host yeast transformed with pBEVY-L was used as negative control.

Results

Figure 25:
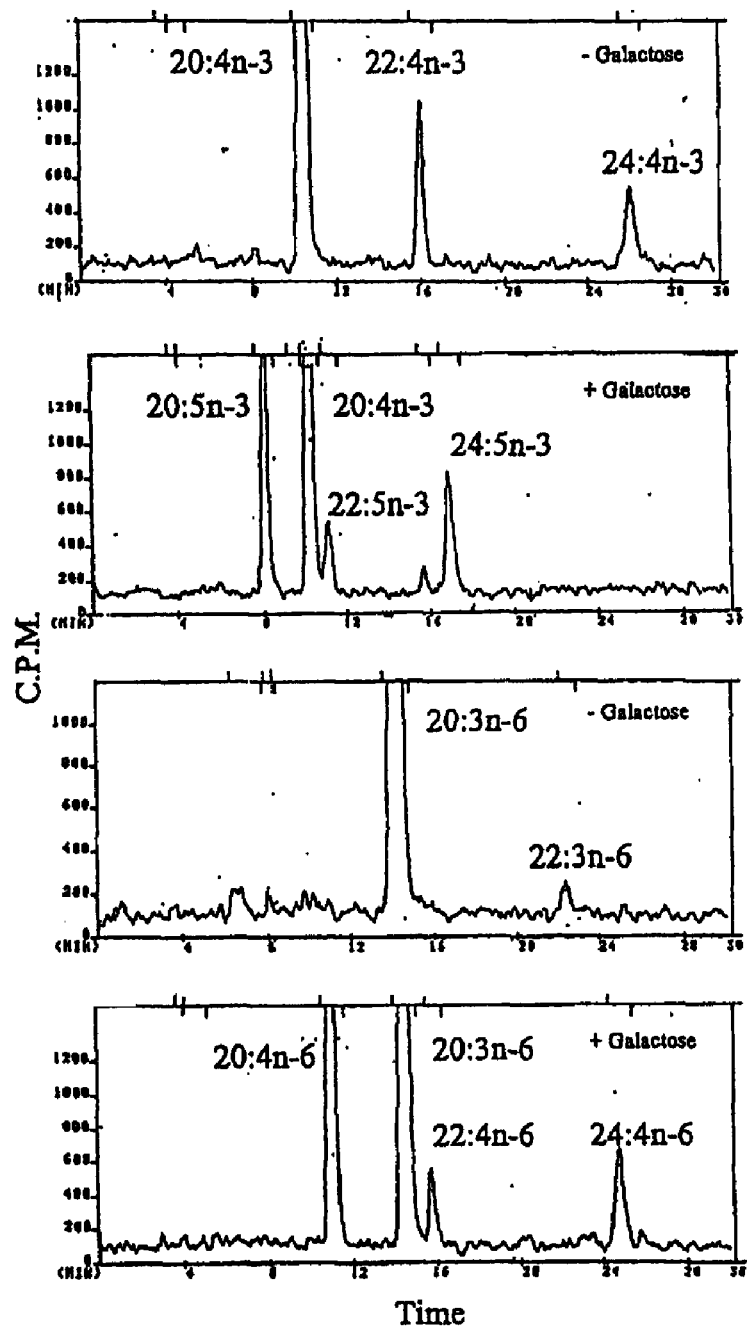
FIG. 25 shows an HPLC analysis, of radiolabelled methyl esters of fatty acids from yeast co-expressing D5D/V5-His and ELG3, incubated with [1-$^{14}$C]20:4n-3 or [1-$^{14}$C]20:3n-6 and with or without galactose.

FIG. 25 shows that 20:3n-6 was desaturated to 20:4n-6, which was further elongated to 22:4n-6 and 24:4n-6, when the yeast co-expressed both genes in the presence of galactose. When galactose was not added to the medium, 20:3n-6 was only elongated to 22:3n-6.

Similarly, D5D/V5-His desaturated 20:4n-3 producing 20:5n-3, which was then elongated to 22:5n-3 and 24:5n-3. The elongation of 20:4n-3 to 22:4n-3 and 24:4n-3 was also detected.

Figure 26:
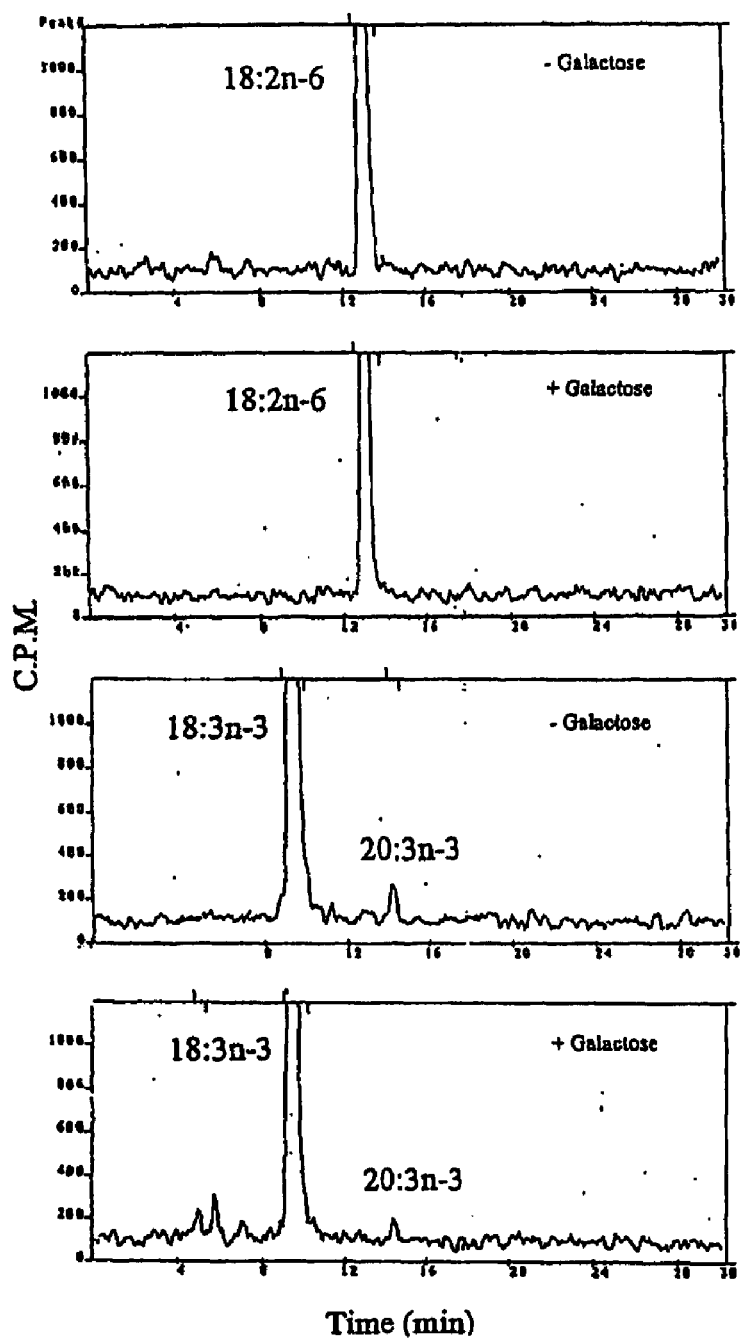
FIG. 26 shows an HPLC analysis of radiolabelled methyl esters of fatty acids from yeast co-expressing D5DNV5-His and ELG3, incubated with [1-$^{14}$C]18:2n-6 or [1-$^{14}$C]8:3n-3 and with or without galactose.

Under these experimental conditions, yeast co-expressing both genes was not able to elongate and further desaturate 18:2n-6. D5D/V5-His was not active on 20:3n-3, the direct elongation product of 18:3n-3 generated by ELG3 (FIG. 26).

Conclusion

Yeast co-expressing ELG3 and a human D5D, both cloned by the inventors, were able to generate substrates (i e., 24:4n-6 and 24:5n-3) of the so called "Sprecher pathway" (Sprecher H. 2000, *Biochim. Biophys. Acta*, 1486: 219-231).

Example 27

Drug Screening Assays Using Whole Cells, Spheroplasts or Microsomes of Yeast Co-Expressing ELG3 and Either Human D6D or D5D The following assays are designed to identify compounds that affect the human elongase ELG3 and/or the human desaturases using one host system or any part thereof.

Spheroplast and Microsome Preparation

Transformed *Saccharomyces cerevisiae* cells are grown in SC-U-Leu medium with 1% raffinose and 2% galactose to induce the expression of the desaturase transgenes. After 16 h incubation, spheroplasts are obtained as described in Example 20.

Microsomes from host cells expressing both elongase and desaturase genes are prepared using the liquid $N_2$ and differential centrifugation methods described in Example 21.

Incubation of Whole Yeast Cells, Spheroplasts or Microsomes with Test Compounds

In these assays with yeast cells containing elongase and desaturase transgenes, the use of SC-U-Leu medium is required to maintain selection pressure. Transformed yeast are incubated with or without galactose to asses the effect of the test component on the activity of ELG3 and the desaturases or the elongase alone, respectively. The substrates of choice are 20:3n-6 or 20:5n-6 for yeast expressing ELG3 and D5D or ELG3 and D6D, respectively. The incubation conditions of whole yeast cells, spheroplasts or microsomes with test compounds are the same as those described in Examples 20 and 21. Regardless of the host system used, the effect of the test compound on the activity of the recombinant enzymes is determined by the RP-HPLC or GC analysis of the relative amounts of FAME produced by ELG3 and/or the desaturases as described in Example 19.

Example 28

Elongation of PUFAs in Primary Cultures of Leukocytes from Control and STZ-Induced Diabetic Rats The present example describes the capability of leukocytes to elongate but not desaturate PUFAs. The example also provides details of how the elongation of 18:3n-6 and 18:2n-6 is affected in rats with STZ-induced diabetes.

Materials

RPMI 1640 medium was obtained from Gibco BRL. Streptozotocin (2-desoxy-2-methylnitrosoamino carbonyl amino-D-glucopyranose) was supplied by Sigma.

Animals

Female Wistar rats were obtained from Charles Rivers, St-Constant, Quebec. Animals were housed in barrier-maintained rooms at 22±2° C., a target relative humidity of 50±10% with 15 air changes per hour and a 12 h light/dark cycle. Water and regular chow were provided ad libitum.

All animals were monitored daily according to standard procedures in compliance with the Canadian Council of Animal Care guidelines for animal experimentation. Fifteen randomly selected rats were intraperitoneally (I.P.) injected with 50 mg of STZ per kg of body weight. Nine days later, animals received a second dose of STZ (75 mg/kg body weight). A second group of 12 rats which were sham injected with sterile 0.9% NaCl served as control. Two and 7 weeks after the last I.P. injection, control and STZ-treated rats (blood glucose levels 21 to >33 mmoles/l) were put under light habitane (15% in mineral oil) anesthesia and sacrificed by exsanguination. Blood was collected into a 10 ml syringe containing 200 µl of a 5% solution of EDTA as anticoagulant.

Leukocyte Isolation

Leukocytes were obtained by mixing 1 volume of whole blood with 5 volumes of sterile erythrocyte lysis buffer (Qiagen, CA). The cell suspension was incubated for 20 min on ice and centrifuged at 400×g for 10 min at 4° C. The supernatant was discarded and the leukocyte pellet was washed and resuspended in 550 µl of 0.9% saline. Aliquots were taken for cell counting. Cellular protein content was measured using the method of Lowry et al (1951, *J. Biol. Chem.*, 193: 265-275) with bovine serum albumin as standard.

Incubation

The present inventors' preliminary studies carried out with leukocytes isolated from Wistar rats showed that leukocytes can elongate 18:2n-6, 18:3n-3, 18:3n-6, 20:3n-6 and 20:4n-6 with the elongation of 18:2n-6 and 18:3n-6 being 6% and 66%, respectively, within 24 h. Based on these results and due to the impairment of D6D in diabetes, 18:2n-6 and 18:3n-6, substrate and product of D6D, respectively, were selected for the incubation of leukocytes from control and STZ-induced diabetic rats. No delta-6-desaturation on 18:2n-6, 18:3n-3 or delta-5-desaturation on 20:3n-6, was detected.

Leukocytes from the 2 and 7 week control group, as well as from the 2 and 7 week STZ-treated rat group, were incubated in RPMI 1640 medium with glutamine, 10% fetal calf serum and antibiotics (50 IU/ml penicillin, 50 µg/ml streptomycin with 5 µM [1-$^{14}$C]8:3n-6 (0.6 µCi) for 10 min to 24 h or with 5 µmM of [1-$^{14}$C]18: n-6. (0.6 µCi) for 24 h.

At the end of each incubation, the cell pellet was obtained by centrifugation at 400×g for 10 min at 4° C. Cells were washed with PBS containing 0.1% bovine serum albumin. Total cellular lipids were extracted with chloroform:methanol (2:1 v/v). Fatty acids were methylated with $BF_3$ and analyzed by RP-HPLC as described in Example 19. Alternatively, FAME can be analyzed by GC as described in Example 19.

Results

Table 7 shows that leukocytes from STZ-induced diabetic rats rapidly converted 18:3n-6 into 20:3n-6. There was a significant increase in the activity of the elongation system in the STZ group, regardless of the time after the last I.P. STZ injection. Conversely, there was an approximately 50% reduction in the elongation of 18:2n-6 to 20:2n-6 in leukocytes obtained 2 weeks after the STZ injection (Table 8). There were no significant changes in the elongation of 18:2n-6 to 20:2n-6 in leukocytes from animals sacrificed 7 weeks after the STZ treatment.

TABLE 7

Conversion of 18:3n-6 into 20:3n-6 in Leukocytes from STZ-Induced Diabetic Rats Sacrificed 2 or 7 Weeks Post-Induction

| Incubation time (h) | 2 weeks | | 7 weeks | |
| --- | --- | --- | --- | --- |
| | STZ | Control | STZ | Control |
| 0 | 0 | 0 | 0 | 0 |
| 0.16 | 50 ± 8 | 31 ± 9 | 37 ± 9 | 33 ± 4 |
| 0.5 | 115 ± 26 | 70 ± 12 | 112 ± 10 | 71 ± 15 |
| 1 | 288 ± 23 | 200 ± 16 | 190 ± 92 | 143 ± 31 |
| 24 | nt | nt | 1008 ± 98 | 628 ± 156 |

Values are expressed in pmol of 20:3n-6 produced/mg cellular protein and represent the mean ± S.D. of 6 rats.
nt: not tested

TABLE 8

Conversion of 18:2n-6 into 20:2n-6 in Leukocytes from STZ-Induced Diabetic Rats Sacrificed 2 or 7 Weeks Post-Induction

| 2 weeks | | 7 weeks | |
| --- | --- | --- | --- |
| STZ | Control | STZ | Control |
| 322 ± 119 | 126 ± 27 | 147 ± 22 | 128 ± 32 |

Leukocytes were incubated for 24 h.
Values are expressed in pmol of 20:2n-6 produced/mg cellular protein and represent the mean ± S.D. of 6 rats.

PUFA metabolism is altered in leukocytes of rats with STZ-induced diabetes. Therefore, leukocytes are an appropriate model to assess the modification or regulation of the elongation system in disease (e.g., diabetes).

Example 29

Elongation of PUFAs in Primary Cultures of Leukocytes from Humans

This example shows that human leukocytes are a suitable model to assess elongase activity on 18:3n-6. This assay may be used in clinical trials to determine alterations in the elongation system in diseases such as diabetes.

Peripheral venous blood from fasted healthy volunteers (30 to 50 years of age) was obtained using 10 ml Vacutainers (Vacutainer Systems, NJ) containing EDTA as anticoagulant. Leukocytes were isolated using the techniques described in Example 28. The incubation of leukocytes with 5 µM [1-$^{14}$C]18:3n-6 (0.6 µCi) for 10 to 60 min was performed under the same conditions described in Example 28.

Results

Table 9 demonstrates that human leukocytes have a capability to rapidly elongate 18:3n-6 to 20:3n-6, similar to that found in rat leukocytes (Example 28). No delta-5-desaturation activity was detected on 20:3n-6.

TABLE 9

Conversion of 18:3n-6 into 20:3n-6 in Leukocytes from Male and Female Volunteers

| Incubation time (h) | Male | Female |
| --- | --- | --- |
| 0 | 0 | 0 |
| 0.16 | 24 ± 5 | 25 ± 4 |
| 1 | 142 ± 60 | 157 ± 50 |
| 24 | 1479 ± 249 | 2233 ± 778 |

Values are expressed in pmol of 20:3n-6 produced/mg cellular protein and represent the mean ± S.D. of 4 volunteers.

REFERENCES

U.S. Pat. No. 3,817,837, June, 1974, Rubinstein et al.
U.S. Pat. No. 3,850,752, November, 1974, Schuurs et al.
U.S. Pat. No. 3,939,350, February, 1976, Kronick et al.
U.S. Pat. No. 3,996,345, December, 1976, Ullman et al.
U.S. Pat. No. 4,275,149, June, 1981, Litman et al.
U.S. Pat: No. 4,277,437, July, 1981, Maggio
U.S. Pat. No. 4,366,241,: December, 1982, Tom et al.
U.S. Pat. No. 4,399,216, August, 1983, Axel et al.
U.S. Pat. No. 4,704,362, November, 1987, Itakura et al.
U.S. Pat. No. 4,766,675, August, 1988, Goeddal et al.
U.S. Pat. No. 4,784,950, November, 1988, Hagen et al.
U.S. Pat. No. 4,801,542, January, 1989, Murray et al.
U.S. Pat. No. 4,816,567, March, 1989, Cabilly et al.
U.S. Pat. No. 4,935,349, June, 1990, McKnight et al.
U.S. Pat. No. 5,130,238, July, 1992, Malek
International Patent Application No. WO 00/55330, September, 2000, Napier J. A.
Patent Cooperation Treaty International Publication No. WO 00/12720, March, 2000, Mukerji et al.
European Published Application No. 0320308, June, 1989, Backman et al.
Patent Cooperation Treaty International Publication No. WO 93/05182, March, 1993, Bruice
International Patent Application No. WO 88/04300, June, 1988, Cech et al.
Canadian Patent Application No. 2,301,158, March, 2000, Winther et al.
Altschul et al., 1990, *J. Molec. Biol.*, 215: 403-410
Ausubel et al., 1994-, *Current Protocols in Molecular Biology*, John Wiley & Sons, Inc., NY
Been M. D. and Cech T. R., 1986, *Cell*, 47: 207-216
Bennett et al., 1995, *J. Mol. Recognit.*, 8: 52-58
Carillo H. and Lipman D., 1988, *SIAM J. Applied Math.*, 48: 1073
Caskey C. T., 1987, *Science*, 236:1223-1229
Church et al., 1988, *Proc. Natl. Acad. Sci.*, 81: 1991-1995
Cinti et al., 1992, *Prog. Lipid Res.*, 31: 1-51
Connolly B. A., 1987, *Nucl. Acids Res.*, 15: 3131-3139
Copsey et al., 1988, *Genetically Engineered Human Therapeutic Drugs*, Stockton Press, NY
Cotter et al., 1995, *Diabetic Neuropathy: New Concepts and Insights*, Elsevier Science B. V., Amsterdam, pp. 115-120
Cotton et al., 1985, *Proc. Natl. Acad. Sci.*, 85: 4397-4401
Daum et al., 1982, *J. Biol. Chem.*, 257: 13028-13033
Davis et al., 1986, *Basic Methods in Molecular Biology*, Elsevier, NY
Deutcher, M., ed., 1990, *Guide to Protein Purification. Meth. in Enzymol.*, Vol.182
Devereux et al., 1984, *Nucl. Acids Res.*, 12: 387-395
Dines et al., 1993, *Diabetologia*, 36: 1132-1138
Erickson et al., 1992, *Ann. Rep. Med. Chem.*, 27: 271-289

Fields S. and Song O., 1989, *Nature*, 340: 245-246
Flavell et al., 1978, *Cell*, 15: 25-41
Folch et al., 1957, *J. Biol. Chem.*, 226: 497-509
Furuyama K. and Sassa S., 2000, *J. Clin. Invest.*, 105: 757-764
Geever et al., 1981, *Proc. Natl. Acad. Sci*, 78: 5081-5085
Goding J. W., 1996, *Monoclonal Antibodies: Principles and Practice: Production and Application of Monoclonal Antibodies in Cell Biology, Biochemistry and Immunology*, 3rd edition, Academic Press, NY
Goszcz et al., 1998, *Methods Find. Exp. Clin. Pharmacol.*, 20: 439-445
Gribskov M. and Devereux J., eds., 1991, *Sequence Analysis Primer*, M Stockton Press, NY
Griffin A. M. and Griffin H. G., eds., 1994, *Computer Analysis of Sequence Data, Part 1*, Humana Press, NJ
Gyuris et al., 1993, *Cell*, 75: 791-803
Hamy et al., 1997, *Proc. Natl. Acad. Sci.*, 94: 3548-3553
Hanahan et al., 1983, *J. Mol. Biol.*, 166: 557-580
Harlow E. and Lane D., eds., 1988, *Antibodies: A Laboratory Manual*, Cold Spring Harbor, N.Y.
Haseloff J. and Gerlach W. L., 1988, *Nature*, 334: 585-591
Horrobin D. F. (ed.), 1990, *Omega-6 Essential Fatty Acids: Pathophysiology and Roles in Clinical Medicine*, Wiley-Liss, NY
Houbenweyl et al., 1987, *Methods of Organic Chemistry*, Wansch E. (ed), Vol. 15 I and II, Thieme, Germany
Huse et al., 1989, *Science*, 246: 1275-1281
Hwang et al., 1999, *Proc. Natl. Acad. Sci*, 96: 12997-13002
Innis M. A. and Gelfand D. H., 1989, *PCR Protocols, A Guide to Methods and Applications*, Innis M. A., Gelfand D. H., Shinsky J. J. and White T. J. (eds), Academic Press, NY, pp. 3-12
Izant J. G. and Weintraub H., 1984, *Cell*, 36: 1007-1015
Jackson et al., 1990, *EMBO J.*, 9: 3153-3162
James et al., 1995, *Plant Cell*, 7: 309-319
Johanson et al., 1995, *J. Biol. Chem.*, 270: 9459-9471
Kawashima et al., 1996, *Biosci. Biotech. Biochem.*, 60: 1672-1676
Kilberg M. S. and Christensen H. N., 1979, *Biochemistry*, 18: 1525-1530
Kohler G. and Milstein C., 1975, *Nature*, 256: 495-497
Kraemer et al., 1993, *J. Lipid Res.*, 34: 663-671
Landegren et al., 1988, *Science*, 241: 1077-1080
Landegren et al., 1989, *Science*, 242: 229-237
Leonard et al., 2000, *Biochem J.*, 350: 765-770
Lesk A. M., ed., 1988, *Computational Molecular Biology*, Oxford University Press, NY
Llewellyn et al., 1987, *J. Mol. Biol.*, 195: 115-123
Lowry et al.; 1951 ,*J. Biol. Chem.*, 193: 265-275
Mack E. W., 1990, *Remington's Pharmaceutical Sciences*, Mack Publishing Company, Easton, Pa., 13th edition
Margolskee et al., 1988, *Mol. Cell. Biol.*, 8: 2837-22847
Mazza G. and Domah B. D. (eds.), 2000, *Herbs, Botanicals, and Teas*, Technomic Publishers, Lancaster, Pa.
McLaughlin et al., 1988, *J. Virol.*, 62: 1963-1973
Mei et al., 1998, *Biochemistry*, 37: 14204-14212
Merrifield, 1964, *J. Am. Chem. Assoc.*, 85: 2149-2154
Miller et al., 1998, *Nucl. Acids Res.*, 26: 3577-3583
Moss et al., 1987, *Annu. Rev. Immunol.*, 5: 305-324
Myers et al., 1985, *Science*, 230: 1242-1246
Myers et al., 1986, *Cold Spring Harbour Sym. Quant. Biol.*, 51: 275-284
Nilsson T. and Warren G., 1994, *Curr. Opini. Cell Biol.*, 6: 517-521
Oh et al., 1997, *J. Biol. Chem.*, 272: 17376-17384
Okano et al., 1988, *EMBO J.*, 7: 3407-3412
Orkin et al., 1988, *Prog. Med. Genet.*, 7: 130-142
Rasmussen et al., 1987, *Meth. Enzymol.*, 139: 642-654
Riemersma et al., 1986, *Br. Med. J. (Clin. Res. Ed.)*, 292: 1423-1427
Rosenberg et al., 1985, *Nature*, 313: 703-706
Saiki et al., 1985, *Science*, 230: 1350-1353
Saiki, et al., 1986, *Nature*, 324: 163-166
Sambrook et al., 1989, *Molecular Cloning, 2nd Edition*, Cold Spring Harbor Laboratory Press, Cold Spring Harbour, N.Y.
Schatz G. and Kovac L., 1974, *Meth. Enzymol.*, 31A: 627-632
Shanklin et al., 1994, *Biochemistry*, 33: 12787-12794
Singer et al., 1984, *Prostaglandis Leukot. Med.*, 15: 159-165
Smith D. W., ed., 1993, *Biocomputing: Informatics and Genome Project*, Academic Press, NY
Sonnhammer et al., 1998, *In Proc. of Sixth Int. Conf. on Intelligent Systems for Molecular Biology*, AAAI Press, CA, pp. 175-182
Sprecher H., 2000, *Biochim. Biophys. Acta*, 1486: 219-231
Suneja et al., 1990, *Biochim. Biophys. Acta*, 1042: 81-85
Thompson et al., 1994, *Nucl. Acids Res.*, 22: 4673-4680
Toke D. A. and Martin C. E., 1996, *J. Biol. Chem.*, 271: 18413-18422
Tvrdik et al., 2000, *J. Cell. Biol.*, 149: 707-717
Tvrdik et al., 1997, *J. Biol. Chem.*, 272: 31738-31746
Ulmasov et al., 1997, *Science*, 276: 1865-1868
von Heijne G., 1987, *Sequence Analysis in Molecular Biology*, Academic Press, NY
Waldmann T. A., 1991, *Science*, 252: 1657-1661
Wallace et al., 1986, *Cold Spring Harbour Symp. Quant. Biol.*, 51: 257-261
Zaug A. J. and Cech T. R, 1986, *Science*, 231: 470-475
Zaug et al., 1984, *Science*, 224: 574-578
Zaug et al., 1986, *Nature*, 324: 429-433

---

We claim:

1. An isolated polynucleotide sequence, comprising a polynucleotide sequence encoding a polypeptide having elongase activity which is selected from the group consisting of: (a) a sequence comprising SEQ ID NO: 4; (b) a sequence at least 95% homologous with sequence (a); (c) a sequence at least 98% homologous with sequence (a); and (d) a sequence at least 99% homologous with sequence (a).

2. A vector transformed with the polynucleotide of claim 1.

3. An isolated host cell comprising the polynucleotide sequence of claim 1, wherein said sequence is heterologous to the host cell.

4. A vector comprising a polynucleotide sequence of claim 1 wherein said sequence is heterologous to the vector.

5. An isolated host cell comprising a polynucleotide encoding a polypeptide sequence having elongase activity selected from the group consisting of: (a) a sequence comprising SEQ ID NO: 5; (b) a sequence which is at least 95% homologous with a sequence of (a); (c) a sequence which is at least 98% homologous with sequence (a); and (d) a sequence which is at least 99% homologous with a sequence of (a) in a host cell which is heterologous to said sequence.

* * * * *

SEQUENCE LISTING

<160> NUMBER OF SEQ ID NOS: 58

<210> SEQ ID NO 1
<211> LENGTH: 989
<212> TYPE: DNA
<213> ORGANISM: human

<400> SEQUENCE: 1
tacaggctcg tgaggcttcc ctcccgctaa gaccagtgcg ccctcagcac acgcagtgtg    60

```
gtctcgcccg ccgctctgcg ctcgccctgc aggagaggga gctctttgaa ggcaaggccg      120
aacctccccc gagccctgag ctgggcctgc cgccacagat gtgcagtcct gccggggagc      180
agtcacccgg ggacagggcc gggcccgggg ctgcacgtcg ggaagagaca gcgtgctcct      240
gaggtggcca ggccgctgca actggccagg gcgggcccgg gcggcgaggg aagggtggg       300 aagcccgggc cgcggcgctt cctgctggga cccggcggca cgcccctgcc ccgccccgg       360 ccgagcctgc gctgccggcc tccggccctg ccggccgccc aatcagcggg cgcccccgc       420 gcggcccgcc cctcccccct ctgtgacaga aagtcggccc agcagatgag gaagtggcag      480
gcaggcaggc tggccccggg gacttctctc tggccctgct ccctccgagc gctccgccgt      540
tgcccgcctg gcccctacgg gtgagtctgg accttccacg gactctccac gtgccggcgc      600
cccctgcctg gccagcccgg cccagcccgg cccagccctg ccctgccctg ccaggctgt      660 gggcgagggt gttcccgggg ccagtgggtg ggaggtccca gctccctggg gccgggcctc      720
gccagcaccc tccctccccc acaccccgt ctctggcccc catttgccta cacccgggcc      780
ttcctccacc acccctgcat ttacctctct ccctcctcct ctcccctccc tcccccgct      840 accctaactt tgccaggcac cttttccctt ccatccatct taaaggaagg aagggacggg      900
ctgagttccc cgacgagaga cacacccaga ttttcctgca gcttggggag aggtcctccc      960
aggagccttg gtccctcctg gcctgccgg                                       989

<210> SEQ ID NO 2
<211> LENGTH: 509
<212> TYPE: DNA
<213> ORGANISM: human

<400> SEQUENCE: 2
cgagggtggg cttctgccac ccaaatgcgg ccacagactc ctgccacgcc tggcagtaaa      60
aaaaccagag ttcagggcat cgacaacttc accggggcta ttgcgcaggc tctgcgttcc      120
acgcaggctt attaggaaga aaggggaaaa aaatttccca gagacacgtg gaaccgaggg     180
gccaaccccg gcctaggctc tccaccgcat cggattctgg aatttacgat cacgaaagtt     240
ctattgtccc gcgattggct cccgggccgc atgacatcat agcgcttgat tcatccttcg     300
ggtcccgatt ggctggccgc gccattgtga cgtcacggtc agcccacgtt ctgattgtag     360
atagccggcg ccttcctctt cccatcgcgc gggtcctagc caccggtgtc tccttctaca     420
tccgcctctg cgccggctgc caccgcgcgt ccctccgccg ccgccgcctt gctgctgctc     480
aaagctgctg ccgcccttg ggctaaaag                                        509

<210> SEQ ID NO 3
<211> LENGTH: 1344
<212> TYPE: DNA
<213> ORGANISM: human

<400> SEQUENCE: 3
ccggtaccta cagttactca ctctgctact gcacaaaact ctgcaagggc tcccacaccg      60
ccccaggtgt gggatgctaa gtgtatggtg caggtacctc cgtgcacagc cacacgggct     120
gctctcaacc ccaataaaca tgtttaccac atgagcctca catgtggtaa acatttttt      180 tttttttttt tttttttga cacagggtct cattctgtcg cccaggctgg agtgcagtgg     240
cgtgatctcg gctcactgca gcctccacct ccagggctca gccatccttc acctcagcc     300 tcccgagtgg ctgggatcac aggcgcaggc caccacaccc agctaatttt tgtatttttt     360
```

-continued

```
atttaagagg cggggtttcg ccatgttgcc caggctggtc ccgaactcct gacctcaagt      420
gattcgcctg cctcagcctc ccaaagtgct gggattacag gagggaacca ccacgcccgc      480
caacttccca tgcttgaggg agaaatggaa gaaagttcat gtaatactca ggcaagtcca      540
attttttcga cgtctttcac ttgggccaca cacacaacta aagtaactag aagcgcaggc      600
tctaggaggc caccgttctg ttcacagtga agagggtgcg ctcaccgttg gtcgtgtccg      660
ctggaagccc cgcgtcaggc cgggagcggg acagagactc ttgctcaggg ccgttatccg      720
aactgatccg cttcccaccg cacccccaga gaaacccacc caaccccta aacctaagaa       780
acccagactg cgcaaacctg caggaacaga gccatttccc cctaatgtgt gcttcaaacc      840
caccgaagcc caactgtaag caagaccagc gtgcccgccc tgcacgatac tgcttctccc      900
cgcagcagcg gctgccgatc tgggcagcgg gtgggtattc ctggggctcc gtggacgttg      960
agccgccgcg cgaaaccggc gccggctgga cctgcaaatc gccgcccggc cggcagggga     1020
cgccgcggac gcgagggcga ggtcggtcgc ccaggagggg gcgcgcgagg ccgcaggggc     1080
ggggggcgcc gcctcacttg ccctgcgccc ctccccgcg cgccctcctg gcgcggcggc      1140
cggcgaggcc cctgtgggag aggggcggg gacgaaacgg ccccgaggct cggagcgccg      1200
cgcggcggcg gcgcgagccc gaggggggcgg ggaggcgcgg gcgggtgtgc gcgcgccggg     1260
cgtgggtgtg ggtggggta accggcgcgg gcgccgagat agcgccgggc agagggaccc      1320
ggctaccctg gacagcgcat cgcc                                             1344
```

```
<210> SEQ ID NO 4
<211> LENGTH: 846
<212> TYPE: DNA
<213> ORGANISM: human

<400> SEQUENCE: 4
```

```
atggccttca gtgatcttac atcgaggact gtgcatcttt atgataattg gatcaaagat       60
gctgatccaa gagttgaaga ttggctcctc atgtcctcgc ctctgccaca aaccatcctc      120
ctaggattct atgtctattt tgtcacttcc ttgggaccaa agctcatgga aaatcgcaag      180
ccctttgaac tcaagaaagc aatgataacg tacaattttt tcatagtact cttttctgtg      240
tatatgtgtt atgagtttgt gatgtctggc tggggtatag gttattcatt tcgatgtgac      300
attgttgact attcacggtc acccacagct ttgaggatgg cacgtacctg ctggctttat      360
tacttctcca aatttattga gctattagat acgatctttt tgttctgcg caagaaaaat       420
agccaagtga ctttccttca tgtattccat cataccatca tgccgtggac ctggtggttt      480
ggagtcaaat ttgctgcagg tggtttggga acattccatg cccttctaaa tacagctgta      540
catgtagtca tgtattccta ctatggactt tctgcattgg ggccagccta ccagaagtat      600
ttgtggtgga aaaaatattt gacatcatta cagcttgtcc agtttgttat tgtcgccatc      660
cacataagcc agttctttt catggaggat tgcaagtatc agtttccagt ctttgcgtgc      720
atcattatga gttacagttt catgtttctg ctgctctttc tccatttttg gtaccgtgct     780
tacaccaaag gtcagaggtt gcccaaaact gtgaaaaatg gaacttgcaa aaacaaagat      840
aattga                                                                 846
```

```
<210> SEQ ID NO 5
<211> LENGTH: 281
<212> TYPE: PRT
<213> ORGANISM: human

<400> SEQUENCE: 5
```

```
Met Ala Phe Ser Asp Leu Thr Ser Arg Thr Val His Leu Tyr Asp Asn
 1               5                  10                  15

Trp Ile Lys Asp Ala Asp Pro Arg Val Glu Asp Trp Leu Leu Met Ser
                20                  25                  30

Ser Pro Leu Pro Gln Thr Ile Leu Leu Gly Phe Tyr Val Tyr Phe Val
            35                  40                  45

Thr Ser Leu Gly Pro Lys Leu Met Glu Asn Arg Lys Pro Phe Glu Leu
        50                  55                  60

Lys Lys Ala Met Ile Thr Tyr Asn Phe Phe Ile Val Leu Phe Ser Val
 65                  70                  75                  80

Tyr Met Cys Tyr Glu Phe Val Met Ser Gly Trp Gly Ile Gly Tyr Ser
                85                  90                  95

Phe Arg Cys Asp Ile Val Asp Tyr Ser Arg Ser Pro Thr Ala Leu Arg
                100                 105                 110

Met Ala Arg Thr Cys Trp Leu Tyr Tyr Phe Ser Lys Phe Ile Glu Leu
                115                 120                 125

Leu Asp Thr Ile Phe Phe Val Leu Arg Lys Lys Asn Ser Gln Val Thr
        130                 135                 140

Phe Leu His Val Phe His His Thr Ile Met Pro Trp Thr Trp Trp Phe
145                 150                 155                 160

Gly Val Lys Phe Ala Ala Gly Gly Leu Gly Thr Phe His Ala Leu Leu
                165                 170                 175

Asn Thr Ala Val His Val Val Met Tyr Ser Tyr Tyr Gly Leu Ser Ala
                180                 185                 190

Leu Gly Pro Ala Tyr Gln Lys Tyr Leu Trp Trp Lys Lys Tyr Leu Thr
            195                 200                 205

Ser Leu Gln Leu Val Gln Phe Val Ile Val Ala Ile His Ile Ser Gln
        210                 215                 220

Phe Phe Phe Met Glu Asp Cys Lys Tyr Gln Phe Pro Val Phe Ala Cys
225                 230                 235                 240

Ile Ile Met Ser Tyr Ser Phe Met Phe Leu Leu Leu Phe Leu His Phe
                245                 250                 255

Trp Tyr Arg Ala Tyr Thr Lys Gly Gln Arg Leu Pro Lys Thr Val Lys
                260                 265                 270

Asn Gly Thr Cys Lys Asn Lys Asp Asn
            275                 280

<210> SEQ ID NO 6
<211> LENGTH: 2456
<212> TYPE: DNA
<213> ORGANISM: human

<400> SEQUENCE: 6
tgcgcctggc tgaacactac attttttta   cttctttatt catgtattgt ctgtcatctc     60
caactagaat gaacgtatag tccctgagaa cggggaattt gttatctatt gaaacttcag    120
ggcctggaac atagcagcac tccagtattt gttaaataaa tgaatccatt tgagcttctg    180
catatttgaa atttcataag tatatataaa tggtaaattg tgatagactc aaaggctagt    240
atcattaggc aattgtctcc cgttcccaaa agacttccta agtctactaa atgatctgtt    300
tttaatatga aagcaaagtt atctaaaaga aaggagaaat ctttagtttt tttgacttcg    360
agattctttg caatttaagc tttttttttt tttttttttt tttttttttg cttttctttc    420
aatggacact ttcgaagttt tacataaaaa cattaaaacc tcttgtttaa tgtagtggga    480
```

```
ttaagctgcc gaaggcaatc cctacatgtg aggaaaatat gcttccgaca ccccaatttt      540
tttttctcc  ctacccatcc tctctggtgg tcctgacgct cccagcccct ttttgtgttt      600
cttgattcca tgctgagaac tcgcaataca aactcaaagc ccacatttgt gaggtggttg      660
ggtcaggact gcaactaaaa atgattattg ttttttaggt ttctggacag ttcaacacca      720
gcctttggtt ttgcctcaga agcagggaac ttctctaggc ccctattttg cctttcagct      780
attgatgatc caaatcatac cagcgattag gaggatcatt accagacaca aggccaggta      840
cgtttaaaaa ataaataaac caagcgcagg tgcacactcc gaacgctcat ccccaccccc      900
actttccaat ccaacagtag gtaacgagaa atgaattttc tagacttttt ttcctgcagc      960
agttgctgtt accagaaaca aagttagatg atatacaatc taatcttcat tgctctaaaa     1020
gtcctctccc catgccccc  aggctgcctc aattctctag tttcttattc cttataagca     1080
ggggatggag ctgaaccaag tcggccttcc cctcccaggg ccttctcctc ttggtctggc     1140
ttccatttca gatgcgaatt aaccctccca atacccttc  agaagcaagg agtccccttt     1200
ttctccgcct ccagcctcag ctaggttttc ctcatttcgg attttttctac agctcattcc     1260
caaatgagtc acgcatgacg acaatttcca ctctgctatg tcagcctgga gatgtccccc     1320
aagtgatggc atctgctctc ggaaagaaag gtcatcggtg ccacgaccag cccgctaac      1380
ccagagcggc cggtgggccc cagtcccgag agtcagggcg cgcggcggag gcgaggccgg     1440
ggcggcctcc gccctcccgg ccgctccccc tcgcgccgcc ccggctcctc cctccggccc     1500
tcggcgggca cctggcggcg gcgggcaggg ggcggcgctg cgcgcgtcac gcggctgggt     1560
gggatagcgg gcaggtgaca cccggcggcc tcctcccctt tccaacccag tcggcggccg     1620
ggacagcagg ggccgctgtg aggagctccg cgctcgcgct gccagtcgcc gccctctctc     1680
ccgcgcgcgc ccggcgcttc ggctccgctc cctgtgcggt gagtgcgggg ttccaggccg     1740
gcgggcaggg gccaaacttt ccggcgcgcg ggaggagaag agactgggga gggaggcaga     1800
gccgagggga acggcgtcgg gagtggccgg atggaggaac ttgggcgcgg cgcgcgagaa     1860
gtgggacccg ggtgcggggg ccccgggagc ggggccaggc cctccctggg ctcgggaggc     1920
gcttgggaag ttctgtcccc gctgcctgcg cgtggggagg accgaggccc ttttcgccgg     1980
agcgcgggc  cgcggcgctc acctgcgcct tctcggagc  ccccacccgg cagcatcccg     2040
aagggaaggt cgggcccggt gggcgcgctg cggagcggag cctggactgg ggtcccgcgc     2100
ggcgctggcc ctgcggagcg gagcgggagg ggcagaggtg ctcgccggcg ggactgggag     2160
ggagaaggac ctgctcgacc ttggacgcgg aggtcatttt cccagctccg gggtctggcc     2220
tcgctagcca ccccccaaa  ttccggagcc cctttctttc tgtttccttc cttcccttt      2280
gggcgctttt tttgctcccg cggccagatg aacttgggc  gctgtccctt cggctccccg     2340
agccgcatcc tgtcttggtg gctgctgctg gccgggagga ggctgatgaa tacagagccg     2400
tggaacaggt cgtgccggag atggaaacag gaaagcctgt tgttttgtcg tcccag         2456
```

<210> SEQ ID NO 7
<211> LENGTH: 1411
<212> TYPE: DNA
<213> ORGANISM: human

<400> SEQUENCE: 7

```
gtgagccacc accgcggccg gtcccttcct cctttaaaaa tttttctccc agttcccact       60
ttttgtgggt tagaggcatc taaattgaat gaaagtaccc ttttggact  actggggagg      120
tgggggatg  ttctcagaag gggaattttc tttctggtcc taatatccac ctaatttta       180
```

-continued

```
aaagcagggc tccttattat tttgtaaagt ttacaattac atcattagat acttccatgt    240
ctcatatttc attttttccaa actcttgggg gaaatgagtg gagggatgga tggaatagaa   300
aatagttttt cctcttggag gctgagggcc cagtaggggt caacagtaca ttcagccctc    360
tcctcacata ttctgttcta cctacaagta cagcaagtaa agccaaattt ctcatgcatg    420
caaataaagt ttttgcattt ggccagtcgg tccagttctc ctgtcagctt ccttccccac    480
tctgcctctg ttcattaatc cccccttcc cggtacctaa accctccacc taacccagcc    540
ctttcttcca cttccggcta ctagcctctc tcgcctatcc actatcctca cactcagcat    600
cccctgtctg tacgagatta aggagctctg ccgtccgcag ggcctgggtt agcgtgaatc    660
taagccagag ctcccgggtg ggggtggggg taggggtggg ggtggtccca gaggtagggc    720
gaggaggtgg gaagcgtatt cccttcactg gtgatctcaa cgtagatttg cccggagttc    780
tcttgcaaga gagctggcag gttttactat ttcccaatcg tttactcgcc aagctctcgg    840
gtccacgcgc cgcggggatg cgccctgcaa gctgaaactt cattcaaagc aaggcggccc    900
acgaggttgg gcttagggga tctgatgac ctccaggcca cttcctttct ctctgcgccc     960
ttcccccact cttccaacca ccttcgctgt aaacaaaact gtcccccccg ggcggagaga   1020
ggtcgcgctc tttcgcacac tccctcgcca agggttaatt tctcaaatcg cacgaggggg   1080
aggagatttc cctgtagacg agtaaaaagg gtgatgaca aacgtgcggg cactaagacc    1140
gcaaggcatt catttcctcc tacggtggat gcggacgccg ggaggaggag agccccagag   1200
agaggagctg ggagcggagg cgcaggcaat gctcagccct ggatgtagct gagaggctgg    1260
gagaagagac gaccgctgga gaccgagcgg cgtggggaag acctaggggg gtgggtgggg    1320
gaagcagaca ggagaacact cgaaatcaag cgctttacag attatttat tttgtataga    1380 gaacacgtag cgactccgaa gatcagcccc a                                   1411
```

<210> SEQ ID NO 8
<211> LENGTH: 813
<212> TYPE: DNA
<213> ORGANISM: human

<400> SEQUENCE: 8

```
atggtcacag ccatgaatgt ctcacatgaa gtaaatcagc tgttccagcc ctataacttc    60
gagctgtcca aggacatgag gccctttttc gaggagtatt gggcaacctc attccccata   120
gccctgatct acctggttct catcgctgtg gggcagaact acatgaagga acgcaagggc    180
ttcaacctgc aagggcctct catcctctgg tccttctgcc ttgcaatctt cagtatcctg    240
ggggcagtga ggatgtgggg cattatgggg actgtgctac ttaccggggg cctaaagcaa    300
accgtgtgct tcatcaactt catcgataat tccacagtca aattctggtc ctgggtctttt  360 cttctcagca aggtcataga actcggagac acagccttca tcatcctgcg taagcggcca    420 ctcatctttta ttcactggta ccaccacagc acagtgctcg tgtacacaag ctttggatac    480
aagaacaaag tgcctgcagg aggctggttc gtcaccatga actttggtgt tcatgccatc   540
atgtacacct actacactct gaaggctgcc aacgtgaagc cccccaagat gctgcccatg   600
ctcatcacca gcctgcagat cttgcagatg tttgtaggag ccatcgtcag catcctcacg    660
tacatctgga ggcaggatca gggatgccac accacgatgg aacacttatt ctggtccttc    720
atcttgtata tgacctattt catcctcttt gcccacttct tctgccagac ctacatcagg    780
cccaaggtca aagccaagac caagagccag tga                                 813
```

<210> SEQ ID NO 9
<211> LENGTH: 270
<212> TYPE: PRT
<213> ORGANISM: human

<400> SEQUENCE: 9

```
Met Val Thr Ala Met Asn Val Ser His Glu Val Asn Gln Leu Phe Gln
  1               5                  10                  15

Pro Tyr Asn Phe Glu Leu Ser Lys Asp Met Arg Pro Phe Phe Glu Glu
             20                  25                  30

Tyr Trp Ala Thr Ser Phe Pro Ile Ala Leu Ile Tyr Leu Val Leu Ile
         35                  40                  45

Ala Val Gly Gln Asn Tyr Met Lys Glu Arg Lys Gly Phe Asn Leu Gln
     50                  55                  60

Gly Pro Leu Ile Leu Trp Ser Phe Cys Leu Ala Ile Phe Ser Ile Leu
 65                  70                  75                  80

Gly Ala Val Arg Met Trp Gly Ile Met Gly Thr Val Leu Leu Thr Gly
                 85                  90                  95

Gly Leu Lys Gln Thr Val Cys Phe Ile Asn Phe Ile Asp Asn Ser Thr
            100                 105                 110

Val Lys Phe Trp Ser Trp Val Phe Leu Leu Ser Lys Val Ile Glu Leu
        115                 120                 125

Gly Asp Thr Ala Phe Ile Ile Leu Arg Lys Arg Pro Leu Ile Phe Ile
130                 135                 140

His Trp Tyr His His Ser Thr Val Leu Val Tyr Thr Ser Phe Gly Tyr
145                 150                 155                 160

Lys Asn Lys Val Pro Ala Gly Gly Trp Phe Val Thr Met Asn Phe Gly
                165                 170                 175

Val His Ala Ile Met Tyr Thr Tyr Tyr Thr Leu Lys Ala Ala Asn Val
            180                 185                 190

Lys Pro Pro Lys Met Leu Pro Met Leu Ile Thr Ser Leu Gln Ile Leu
        195                 200                 205

Gln Met Phe Val Gly Ala Ile Val Ser Ile Leu Thr Tyr Ile Trp Arg
    210                 215                 220

Gln Asp Gln Gly Cys His Thr Thr Met Glu His Leu Phe Trp Ser Phe
225                 230                 235                 240

Ile Leu Tyr Met Thr Tyr Phe Ile Leu Phe Ala His Phe Phe Cys Gln
                245                 250                 255

Thr Tyr Ile Arg Pro Lys Val Lys Ala Lys Thr Lys Ser Gln
            260                 265                 270
```

<210> SEQ ID NO 10
<211> LENGTH: 1937
<212> TYPE: DNA
<213> ORGANISM: human

<400> SEQUENCE: 10

| | | |
|---|---|---|
| gattagctgt caggctatat atggagccat caggaaccac tgaaggtttt tttttttttt | 60 |
| ttttttttg agacggagtc tcactctgtc acccaggctg gagtgcagtg gcacgatctc | 120 |
| tgctcactgc aagctctgcc tcccaggttc acgccattct cctgcctcag cctcccgagt | 180 |
| agctgggact acaggcgcct gccaccacgc ccggctaatt ttttgtattt tttagtagag | 240 |
| acggggtttg acggtgttag ccaggatggt ctcgatctcc tgacctcatg atctgcccgc | 300 |
| ctcggcctcc caaggtgctg ggattacagg cgtgaaccac cgtgcccggc cgaaccactg | 360 |

```
aaggttttta agcaggaaag cagagctgtt ttctggatga gcaaacagaa agtagtggtt      420
ttccaagtac agtctgagac aacctatagg accagaatct ctgcagttga ggctcaggaa      480
tctggtaatc agccaggtat aggaactctt ttctgattgc aatgcagtga agagcagaag      540
cactgtatta gagaaagagg cagtgcaacc aggtaacgtg accaggtgag aagtgatgag      600
gtacagagac aaagagatgc acttttgagt cacttagatg gcactgatag gacttccact      660
acaccctcgc atagacagtg gctgaggttc aggaaataga gctggggttc ctacttggat      720
cctctggctc tagagcttta ctgcacatag ccatttatac ccacatcttg attttaatta      780
ttttatatct atgtttctta gcactttttg caaatttcca ccttatctca aactgccctc      840
aagccttgta tttctccttc gctttcataa aacctaggaa agaaataagg acagccaag       900 taaaactttt aaagttttta gaacatttat ttctttgggg ctggttacac aggcgagaaa      960
gaagtagatt tggttaggga gagaaaacaa caggccttgg ggagatacac tggctctccc     1020
cctccctaaa ccctaagagg cctccaggaa acctgaagac aataattcca gaagcccaga     1080
gggtgacccc atttcctctc tccatggtta ttactgtcag tctggagcag ttcaggaatt     1140
caggaaacta taaagaaacc acaacagcct caacaaccca aacatcaaca tcaacaacct     1200
caacaataaa actccttaaa attcatctcc ttccacccac tcacaaccgc agactcgaag     1260
ctaggaggtg gaagggacta cagaagctct gcgttgccca ggttagtatt tgctcatcac     1320
aggcctgggt ttcccaggat ctcagggagc ctggaaactg acgcctccat ttctgggtgg     1380
gagcaccaaa gcctaaggac accttttcctc tctcttcact gctaagcagg tcaagattaa     1440
agcaaaccga ggcaaaggcc acggttgaca gttccaaggg aacccgcaag gccgcacagg     1500
atggggtgga cgttttacgg gagaaaaggc tggggaagtg ggcgggcgat ggcctacgac     1560
gggacttggg gcggggtgtg cgaaacgcct ggcaggcggg cccttgagta tgaccaatca     1620
gaatgcggac tgcgtcccag gggcggagca gaggcgtatc ttggtcgaga ttggatagcg     1680
gcggggcgca ggaaagaggt cgcgccagcc cgggcaggca gctttgcaag tccgcgttat     1740
atatcgcagt ggctgcgccc gggatagctg gctgcgccgc cgcgcacatg cctaggttcg     1800
acgccctcct cccttttgccc aggagttcct tctgtcccgg ctctgttccg tctcgccccg     1860
aggttcacgc catcctcgga gccccagcct ttcacccagc gcctccaagc tttggacctt     1920
gacttctgca aaactag                                                    1937
```

<210> SEQ ID NO 11
<211> LENGTH: 945
<212> TYPE: DNA
<213> ORGANISM: human

<400> SEQUENCE: 11

```
atggggctcc tggactcgga gccgggtagt gtcctaaacg tagtgtccac ggcactcaac       60
gacacggtag agttctaccg ctggacctgg tccatcgcag ataagcgtgt ggaaaattgg      120
cctctgatgc agtctccttg gcctacacta agtataagca ctctttatct cctgtttgtg      180
tggctgggtc caaaatggat gaaggaccga gaaccttttc agatgcgtct agtgctcatt      240
atctataatt ttgggatggt tttgcttaac ctctttatct tcagagagtt attcatggga      300
tcatataatg cggatatag  ctatatttgc cagagtgtgg attattctaa taatgttcat      360
gaagtcagga tagctgctgc tctgtggtgg tactttgtat ctaaaggagt tgagtatttg      420
gacacagtgt tttttattct gagaaagaaa acaaccaag tttctttcct tcatgtgtat      480
catcactgta cgatgtttac cttgtggtgg attggaatta agtgggttgc aggaggacaa      540
```

```
gcattttttg gagcccagtt gaattccttt atccatgtga ttatgtactc atactatggg    600
ttaactgcat ttggcccatg gattcagaaa tatctttggt ggaaacgata cctgactatg    660
ttgcaactga ttcaattcca tgtgaccatt gggcacacgg cactgtctct ttacactgac    720
tgccccttcc ccaaatggat gcactgggct ctaattgcct atgcaatcag cttcatattt    780
ctctttctta acttctacat tcggacatac aaagagccta agaaaccaaa agctggaaaa    840
acagccatga atggtatttc agcaaatggt gtgagcaaat cagaaaaaca actcatgata    900
gaaaatggaa aaagcagaa aaatggaaaa gcaaaaggag attaa    945
```

<210> SEQ ID NO 12
<211> LENGTH: 314
<212> TYPE: PRT
<213> ORGANISM: human
<400> SEQUENCE: 12

```
Met Gly Leu Leu Asp Ser Glu Pro Gly Ser Val Leu Asn Val Val Ser
  1               5                  10                  15

Thr Ala Leu Asn Asp Thr Val Glu Phe Tyr Arg Trp Thr Trp Ser Ile
             20                  25                  30

Ala Asp Lys Arg Val Glu Asn Trp Pro Leu Met Gln Ser Pro Trp Pro
         35                  40                  45

Thr Leu Ser Ile Ser Thr Leu Tyr Leu Phe Val Trp Leu Gly Pro
     50                  55                  60

Lys Trp Met Lys Asp Arg Glu Pro Phe Gln Met Arg Leu Val Leu Ile
 65                  70                  75                  80

Ile Tyr Asn Phe Gly Met Val Leu Leu Asn Leu Phe Ile Phe Arg Glu
                 85                  90                  95

Leu Phe Met Gly Ser Tyr Asn Ala Gly Tyr Ser Tyr Ile Cys Gln Ser
            100                 105                 110

Val Asp Tyr Ser Asn Asn Val His Glu Val Arg Ile Ala Ala Ala Leu
        115                 120                 125

Trp Trp Tyr Phe Val Ser Lys Gly Val Glu Tyr Leu Asp Thr Val Phe
    130                 135                 140

Phe Ile Leu Arg Lys Lys Asn Asn Gln Val Ser Phe Leu His Val Tyr
145                 150                 155                 160

His His Cys Thr Met Phe Thr Leu Trp Trp Ile Gly Ile Lys Trp Val
                165                 170                 175

Ala Gly Gly Gln Ala Phe Phe Gly Ala Gln Leu Asn Ser Phe Ile His
            180                 185                 190

Val Ile Met Tyr Ser Tyr Tyr Gly Leu Thr Ala Phe Gly Pro Trp Ile
        195                 200                 205

Gln Lys Tyr Leu Trp Trp Lys Arg Tyr Leu Thr Met Leu Gln Leu Ile
    210                 215                 220

Gln Phe His Val Thr Ile Gly His Thr Ala Leu Ser Leu Tyr Thr Asp
225                 230                 235                 240

Cys Pro Phe Pro Lys Trp Met His Trp Ala Leu Ile Ala Tyr Ala Ile
                245                 250                 255

Ser Phe Ile Phe Leu Phe Leu Asn Phe Tyr Ile Arg Thr Tyr Lys Glu
            260                 265                 270

Pro Lys Lys Pro Lys Ala Gly Lys Thr Ala Met Asn Gly Ile Ser Ala
        275                 280                 285

Asn Gly Val Ser Lys Ser Glu Lys Gln Leu Met Ile Glu Asn Gly Lys
    290                 295                 300
```

Lys Gln Lys Asn Gly Lys Ala Lys Gly Asp
305 310

<210> SEQ ID NO 13
<211> LENGTH: 2000
<212> TYPE: DNA
<213> ORGANISM: human

<400> SEQUENCE: 13

| | | | | | |
|---|---|---|---|---|---|
| ggaaatacct | gaagctgttt | taacaatttc | tccttgtatt | aagtattatg | ctgcagtttt |   60 |
| gcgtgtgtga | atggaagtat | gggtagagat | ctgttctccc | taaaaactcc | aggattccac |  120 |
| aatatagaaa | tagtaatcaa | atttttaggt | gaagctcgaa | ctaatccgaa | ctttgttaga |  180 |
| tcatcactgt | aaatgaatgg | gtatttatcc | actccctaaa | tgaagagact | tgactggatt |  240 |
| tcttttttt | atatagctac | tagaatctgt | tacacataat | ttaggattga | acttgagaa |  300 |
| attgtcattc | caatccagaa | aactttagat | ttgcaaatat | atttgacaaa | ttaataaatt |  360 |
| aacattttat | ttggttaatt | tcaagaatag | ggcatttaaa | gaagtctgtg | tttgctttag |  420 |
| ttcggcaata | aagttcctgc | cactcacaat | aatccttatt | attctctgaa | agacatgtta |  480 |
| tattttttgtc | atcataaata | tttattaatt | actgtttata | gcactgggtt | aggtactcat |  540 |
| caagcaacca | aaaataattc | ttaccatcta | ggatgcttcc | aatataaaat | atagacaata |  600 |
| tataaccagg | tcaattggga | aatagatcat | ttcagtatga | taaaagatag | tattcacatt |  660 |
| aacagtgtga | aagggcagga | acaataagac | acttgactca | ctggtcttta | aaatgtagca |  720 |
| tccaaaatga | gcaagtggag | aaaaggttaa | acaagtaggt | gacacattta | aaaaacaagt |  780 |
| agatgaaagg | actattctca | aaaatcttgt | tttatgtgag | aaaccatcaa | attatgaatt |  840 |
| ccaagtactg | tattttttt | acttttcaag | ggtaggctct | cctataccct | atctaaacaa |  900 |
| tttttcaaaa | tagccacaat | tacttgtttt | tcctctctac | actaaattgc | cctttgcctc |  960 |
| ttgagcgatt | atcttttttca | gattcacctc | aacttcttca | ggttcaagcg | gacttcacct | 1020 |
| gtaagcccct | ctcggttctc | cctcttctct | gaactactaa | tggcctaatt | tagcacaatt | 1080 |
| atattgcttt | gttcattcca | tgtatagtaa | aagagtctac | aaaacacatg | caagcattca | 1140 |
| tgcaattata | tgttgatttg | ttcatgggtc | gacccccaaag | tctattctcc | atcgctgaag | 1200 |
| catggaagac | aaatacccctt | cacttcttca | gaggcataac | acatgcactt | ctcttgtcat | 1260 |
| ggtgacaggc | atgtgctggt | ggaggtcaaa | gaaacaggaa | cacaagtgaa | atcgaggtga | 1320 |
| gtgtcaggta | aggaccaaag | caccacgcct | acctcatctt | tgcccacaga | acacccattc | 1380 |
| ttcccgtgtc | ctgttcccca | ggacgtatcc | gggggcggata | agaaatcacc | cgtggggagg | 1440 |
| cggtgaactc | ctccgcaggg | gccgatgccc | gggacagggg | cggggaaggc | taatgaggcg | 1500 |
| acttgtgcgg | ggaggggcca | aggaggagcc | caggtgtccc | gctcccgctc | gacggcgcgc | 1560 |
| gcctgcgcga | gcccagttgg | cgtcgcaccc | ttgagcgcag | catccctacg | ccagcgagtc | 1620 |
| ccaatactag | ggagggaggg | agggaggagg | ggcggccggc | ccccgccccc | cgcgcgcggc | 1680 |
| cacgtgacgc | cggctgagga | gattggaggg | gcggctgcgc | gaggctgcag | actggtgcag | 1740 |
| cgcactgtgc | tggcggctgg | gcctcctcca | cctcctcgtc | tttctcccgg | gaaccttgac | 1800 |
| gacgccttcc | gcttggccct | gccttctgcc | gcatccccgc | cgccgcggcg | ccttgaggag | 1860 |
| caggagaaga | cgcagccggg | ccgccgccgt | tagagggggtt | cccggccgcc | gctcgccccg | 1920 |
| tcggccgcca | ccgcctccgg | ggtcagccct | ctctctgggt | ctccgctttc | tcctgccgcc | 1980 |
| agcgcccgct | catcgccgcg | | | | | 2000 |

```
<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 14
cacgcgggta ccaggatgga ggctgttgtg aac                              33

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence:Primer

<400> SEQUENCE: 15
atatcacgat gcggccgctc agttggcctt gaccttggc                        39

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence:Primer

<400> SEQUENCE: 16
atatcacgat gcggccgcca gttggccttg accttggc                         38

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 17
gtaacaggag tatgggaagg ca                                          22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 18
ttggactcac actgctgtct ct                                          22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 19
gtgtggcacc aaaataagag tg                                          22

<210> SEQ ID NO 20
<211> LENGTH: 37
<212> TYPE: DNA
<213> ORGANISM: Artificial Sequence
<220> FEATURE:
```

<223> OTHER INFORMATION: Description of Artificial Sequence:Primer

<400> SEQUENCE: 20
cacgcgggat cccaaatgga acatttgat gcatcac    37

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence:Primer

<400> SEQUENCE: 21
atatcacgat gcggccgctc aatccttccg cagcttcc    38

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence:Primer

<400> SEQUENCE: 22
atatcacgat gcggccgcca atccttccgc agcttcc    37

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 23
cacgcgggat ccatcatgga acatctaaag gcc    33

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence:Primer

<400> SEQUENCE: 24
atatcacgat gcggccgctt attgtgctttt cttgttcatc actcc    45

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence:Primer

<400> SEQUENCE: 25
atatcacgat gcggccgctt ttgtgctttc ttgttcatca ctcc    44

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 26
gccagcctac cagaagtatt tg    22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 27
gcgcaagaaa aatagccaag                                                  20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 28
aatgatgcac gcaaagactg                                                  20

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 29
cacgcgggat ccctgatgaa tacagagccg tgg                                   33

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence:Primer

<400> SEQUENCE: 30
atatcacgat gcggccgctc aattatcttt gttttttgcaa gttcc                      45

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence:Primer

<400> SEQUENCE: 31
cacgcgggat ccctgatgga aaagcccatt aatattc                               37

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence:Primer

<400> SEQUENCE: 32
atatcacgat gcggccgctc aattatcttt gttttttgcaa gttcc                      45

<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence:Primer

```
<400> SEQUENCE: 33
atatcacgat gcggccgcca attatctttg tttttgcaag ttcc            44

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence:Primer

<400> SEQUENCE: 34
cacgcgggat ccaaaaatga acatgtcagt gttgacttta caag            44

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence:Primer

<400> SEQUENCE: 35
atatcacgat gcggccgcct attcagcttt cgttgttttc ctc             43

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence:Primer

<400> SEQUENCE: 36
atatcacgat gcggccgcca ttcagctttc gttgttttcc tc              42

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence:Primer

<400> SEQUENCE: 37
cacgcgggat ccaaaaatgg tcacagccat gaatgtctc                  39

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence:Primer

<400> SEQUENCE: 38
atatcacgat gcggccgctc actggctctt ggtcttggc                  39

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence:Primer

<400> SEQUENCE: 39
atatcacgat gcggccgcca ctggctcttg gtcttggc                   38

<210> SEQ ID NO 40
<211> LENGTH: 38
```

<212> TYPE: DNA
<213> ORGANISM: Artificial Sequence
<220> FEATURE:
<223> OTHER INFORMATION: Description of Artificial Sequence:Primer

<400> SEQUENCE: 40
cacgcgggat ccaaaaatgg ggctcctgga ctcggagc                              38

<210> SEQ ID NO 41
<211> LENGTH: 49
<212> TYPE: DNA
<213> ORGANISM: Artificial Sequence
<220> FEATURE:
<223> OTHER INFORMATION: Description of Artificial Sequence:Primer

<400> SEQUENCE: 41
atatcacgat gcggccgctt aatctccttt tgcttttcca tttttctgc                  49

<210> SEQ ID NO 42
<211> LENGTH: 48
<212> TYPE: DNA
<213> ORGANISM: Artificial Sequence
<220> FEATURE:
<223> OTHER INFORMATION: Description of Artificial Sequence:Primer

<400> SEQUENCE: 42
atatcacgat gcggccgctt atctcctttt gcttttccat tttctgc                    48

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 43
ggaagatctt acaggctcgt gaggcttccc tcccg                                 35

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 44
ggaagatctc cggcaggagg gaccaaggct                                       30

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 45
ggaagatctc gagggtgggc ttctgccacc c                                     31

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 46
ggaagatctc ttttagccca aggggcggca gc                         32

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence:Primer

<400> SEQUENCE: 47
ggaagatctt tcgtgtgaat ttccttcaag tctc                       34

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 48
ggaagatctt gatccgcagc ggctgtg                               27

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 49
ggaagatctc cggtacctac agttactcac tctgc                      35

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 50
ggaagatctg gcgatgcgct gtccagggta                            30

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 51
cgacgcgttg cgcctggctg aacactac                              28

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 52
ggaagatctc tgggacaaac aacaggc                               27

<210> SEQ ID NO 53
<211> LENGTH: 28
<212> TYPE: DNA
<213> ORGANISM: Artificial Sequence

```
<220> FEATURE:
<223> OTHER INFORMATION: Description of Artificial Sequence:Primer

<400> SEQUENCE: 53
ccgctcgagg tgagccacca ccgcggcc                                    28

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 54
ccgctcgagt ggggctgatc ttcggagtcg c                                31

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence:Primer

<400> SEQUENCE: 55
ccgagctcga ttagctgtca ggctatatat ggagcc                           36

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 56
ccgagctcct agtttgcaga aggtccaaag c                                31

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 57
ccgagctcgg aaatacctga agctgtttta ac                               32

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 58
ccgagctccg cggcgatgag cgggc                                       25
```